United States Patent
Henard et al.

(10) Patent No.: US 10,889,821 B2
(45) Date of Patent: *Jan. 12, 2021

(54) ORGANIC ACID SYNTHESIS FROM C1 SUBSTRATES

(71) Applicant: Alliance for Sustainable Energy, LLC, Golden, CO (US)

(72) Inventors: Calvin A. Henard, Westminster, CO (US); Michael T. Guarnieri, Denver, CO (US)

(73) Assignee: Alliance for Sustainable Energy, LLC, Golden, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/548,971

(22) Filed: Aug. 23, 2019

(65) Prior Publication Data
US 2020/0071704 A1    Mar. 5, 2020

Related U.S. Application Data

(63) Continuation of application No. 15/252,648, filed on Aug. 31, 2016, now Pat. No. 10,435,693.

(60) Provisional application No. 62/212,264, filed on Aug. 31, 2015.

(51) Int. Cl.
| | | |
|---|---|---|
| C12P 7/44 | (2006.01) | |
| C12N 1/21 | (2006.01) | |
| C12N 9/88 | (2006.01) | |
| C12N 9/02 | (2006.01) | |
| C12N 9/10 | (2006.01) | |
| C12N 9/12 | (2006.01) | |
| C12N 15/53 | (2006.01) | |
| C12N 15/54 | (2006.01) | |
| C12N 15/60 | (2006.01) | |
| C12N 15/52 | (2006.01) | |

(52) U.S. Cl.
CPC .......... *C12N 15/52* (2013.01); *C12N 9/0069* (2013.01); *C12N 9/1022* (2013.01); *C12N 9/1294* (2013.01); *C12N 9/88* (2013.01); *C12P 7/44* (2013.01); *C12Y 113/11001* (2013.01); *C12Y 202/01001* (2013.01); *C12Y 207/09002* (2013.01); *C12Y 401/01059* (2013.01); *C12Y 401/01063* (2013.01); *C12Y 401/02009* (2013.01); *C12Y 402/01118* (2013.01)

(58) Field of Classification Search
None
See application file for complete search history.

(56) References Cited

U.S. PATENT DOCUMENTS 6,489,100 B1  12/2002  Liao

| 8,592,189 B2 | 11/2013 | Burgard et al. |
| 2009/0305364 A1 | 12/2009 | Burgard et al. |
| 2012/0156735 A1 | 6/2012 | Dauner et al. |
| 2017/0058280 A1 | 3/2017 | Henard et al. |
| 2017/0369913 A1 | 12/2017 | Suominen et al. |

FOREIGN PATENT DOCUMENTS

WO    2015/160848 A1    10/2015

OTHER PUBLICATIONS

Vartiainen et al., Evaluation of synthetic formaldehyde and methanol assimilation pathways in Yarrowia lipolytica, Fungal Biol. Biotechnol., 2019, 6, 27.*
Whitaker et al., Synthetic methylotrophy, Curr. Opin. Biotechnol. 33, 2015, 165-175.*
Niu et al., Benzene-free synthesis of adipic acid, Biotechnol. Prog. 18, 2002, 201-11.*
Ceregino et al., Production of recombinant proteins in ferementer cultures of the yeast Pichia pastoris, Curr. Opinion Biotechnol. 13, 2002, 329-32.*
Curran et al., Metabolic engineering of muconic acid production in *Saccharomyces cerevisiae*, Metabolic Eng. 15, 2013, 55-66.*
Rosenblueth et al., Klebsiella variicola, a novel species with clinical and plant-associated isolates, System. Appl. Microbiol. 27, 2004, 27-35.*
Uniprot, Accession No. A0A0B7G3X3, 2015, www.uniprot.org.*
Zhang et al., Engineering *Escherichia coli* coculture systems for the production of biochemical products, Proc. Natl. Acad. Sci. USA 11, 2015, 8266-71.*
Strong et al., Methane as a Resource, Environ. Sci. Technol. 49, 2015, 4001-18.*
Kalyuzhnaya et al., Metabolic engineering in methanotrophic bacteria, Metabolic Eng. 29, 2015, 142-52.*
Xie et al., Biotechnological production of muconic acid: current status and future prospects, Biotechnol. Adv. 32, 2014, 615-22.*
Uniprot, Accession No. A0A0B7G3X3, 2015, accessed at www.uniprot.org.
Uniprot, Accession No. A0A0B7G7Q8, 2015, accessed at www.uniprot.org.
Bogorad et al., "Synthetic Non-oxidative Glycolysis Enables Complete Carbon Conservation", Nature, Oct. 31, 2013, vol. 502, No. 7473, pp. 693-697.
Cereghino et al., "Production of Recombinant Proteins in Fermenter Cultures of the Yeast *Pichia pastoris*", Current Opinion in Biotechnology, 2002, vol. 13, pp. 329-332.
Curran et al., "Metabolic Engineering of Muconic Acid Production in Saccharomyces cerevisiae", Metabolic Engineering, 2013, vol. 15, pp. 55-66.
Heijstra et al., "Gas Fermentation: Cellular Engineering Possibilities and Scale Up", Microbial Cell Factories, 2017, vol. 16, No. 60, pp. 1-11.

(Continued)

*Primary Examiner* — Robert B Mondesi
*Assistant Examiner* — Todd M Epstein
(74) *Attorney, Agent, or Firm* — Alexandra M. Hall; Sam J. Barkley; John C. Stolpa

(57) ABSTRACT

Presented herein are biocatalysts and methods for converting C1-containing materials to organic acids such as muconic acid or adipic acid.

12 Claims, 21 Drawing Sheets

Specification includes a Sequence Listing.

(56) References Cited

OTHER PUBLICATIONS

Kalyuzhnaya et al., "Classification of halo(alkali)philic and halo(alkali)tolerant methanotrophs provisionally assigned to the genera *Methylomicrobium* and *Methylobacter* and emended description of the genus *Methylomicrobium*", International Journal of Systematic and Evolutionary Microbiology, 2008, vol. 58, pp. 591-596.

Kalyuzhnaya et al., "Metabolic Engineering in Methanotrophic Bacteria", Metabolic Engineering, 2015, vol. 29, pp. 142-152.

McDonald et al., "Molecular Ecology Techniques for the Study of Aerobic Methanotrophs", Applied and Environmental Microbiology, Mar. 2008, vol. 74, No. 5, pp. 1305-1315.

Neidle et al., "Cloning and Expression of Acinetobacter calcoaceticus Catechol 1,2-Dioxygenase Structural Gene catA in *Escherichia coli*", Journal of Bacteriology, Nov. 1986, vol. 168, No. 2, pp. 815-820.

Niu et al., "Benzene-Free Synthesis of Adipic Acid", Biotechnology Progress, 2002, vol. 18, pp. 201-211.

Ojala et al., "Genetic Systems for Moderately Halo (Alkali)philic Bacteria of the Genus *Methylomicrobium*", Methods in Enzymology, 2011, vol. 495, pp. 99-118.

Ochsner et al., "*Methylobacterium extorquens*: Methylotrophy and Biorechnological Applications", Applied Microbiology and Biotechnology, 2015, vol. 99, pp. 517-534.

Rosenblueth et al., "*Klebsiella variicola*, A Novel Species with Clinical and Plant-Associated Isolates", Systematic and Applied Microbiology, 2004, vol. 27, pp. 27-35.

Sun et al., "A Novel Muconic Acid Biosynthesis Approach by Shunting Tryptophan Biosynthesis via Anthranilate", Applied and Environmental Microbiology, Jul. 2013, vol., 79, No. 13, pp. 4024-4030.

Xie et al., "Biotechnological Production of Muconic Acid: Current Status and Furture Prospects", Biotechnology Advances, 2014, vol. 32, pp. 615-622.

Zhang et al., "Engineering *Escherichia coli* Coculture Systems for the Production of Biochemical Products", PNAS, Jul. 2015, vol. 112, No. 27, pp. 8266-8271.

\* cited by examiner

```
ATGCTGAGGTCGATCGCTACAGTCTCAATATCGGGCACCCTACCAGAAAAATTGCACGCG
ATAGCGGCTGCGGGATACCAGGGCGTCGAAATCTTCGAAAACGACTTGCTGTATTACACT
GGTACTCCAGCCGAGATCAGGCAGCTAGCGGCGGACCTAGGTCTTAAAATCACCTTGTTC
CAACCGTTCCGTGACTTCGAAGGTGCCTCGCGTGCCCAGTTCGCTGCGAACATGGCGAGG
CGCGACGCAAATTCGCGTTAATGCGTGAATTGGGTTGCGAAACTTTGCTTTTGTGTAGC
AATGTCCAACCTGACTGCAGCGCGGACTCGGAACTGCAAGTTGCTGATTTACGTGCCTTG
GCCACCTTGGCCGAAGAAGAAGGTATCGCGATTGGGTACGAAGCGCTGGCCTGGGGCACT
CATGTTAACCGTTGGCAACAAGCCTGGGAACGAGTGCGTAGGGTCGACTCCCCGGCGTTG
GGGCTGGTTTTGGACTCTTTCCACATACTGGCTCGCGGTGACACACTTGACGCGCTGCCT
TCAGTCCCGGTCGAAAAAATCACGTTTGTTCAATTAGCTGATGCCCCATATATGAAAATG
GACCTACTGGAATGGTCAAGGCATTTCCGGTGTTTCCCCGGTCAAGGAGAATTGCCACTG
GAAGCATTCGCCGAACAAATTACGCGGTGCGGGTATCGTGGCCCATGGAGCCTCGAGATC
TTCAATGACGGCTTCCGTGCCAGCCCCAATGGCGCGACGGCCAAAGACGGCTACCGTTCT
TTATTGTGGTTGGAAGAACAAACGCGCAGGCGTCTGCCTACGTGCGACGCGGACCTTTTC
TCTCCTCCTCCGCTTCCAGTCTACCATGGCTTGGAGTTCATCGAATTCGCGGCTTCAGCC
GCTGAAGCCCAACGCCTGGGCCAACACTTGCAAGCGTTGGGGTTCCAACATGAAGGCTCT
CATCGTAGCCGCCGAGTTACTCTCTGGCGCAACGGCGGTGCTCGCATCGTTATCAACCAT
CAACCGCATAGCTGGGCGGACCATTTCTACCAACGACATGGTGTCTCTTTGTGTGCGATG
GCTCTACGTGTTGAGCATTCGGCTTCTCTGGTTGCGCGCGCTCGAGCTCTGGGCTACGCG
ACGTGGCAAGGCGACGCGGGCCCTAACGAAACGCCAATACCGGCGATCTGCGCCCCGGAC
GGTTCTTTGATCTATTTAATTGATGCCGGCGAGGCTATATACGAACGAGACTTTCATCTA
CGTGACGGTGTTACTGTGCGTGAGGACTACCTTGGCATAGACCATTTAGCGTTGGGTATG
GAAGCTGACTCGCGCGATAACTGGGTTATGTTCTTCCGCACCGTGTTCGGTTTCTCGCTC
GAGCATGAGCAAACGTTGCCGGACCCATATGGGTTGGTTCGCTCGCTAGCCGTTCGCTCG
CCTCAGGGTGACATCCGTCTGGCGTTAAACATCAGTCAATCTCGAGCGACCCAAATCGCT
CGCTCGGTTGCCTGCTACCAAGGCGCTGGCTTGCAACATGCCGCTTTTGCCTGTCGGGAC
CTGCCTGCCGCCTGTGATCAACTGGCAGAAGTGGCTCGTCATACGTTGCCGATTCCAGCT
AACTACTACGACGATCTACTTGCGCGATTCGGCGGCGAACTGGACGTGGGGCAACTACAA
CGGCAACAGTTACTCTACGATCGCGACCCGCAAGGCGGCGACTTCCTGCATTTGTACACT
CGACCGTTCACTGCAGGCAGATTCTTCTTCGAATTGACTGAACGTCGAGCGGGCTACGCC
TTGTACGGTGCGGCGAACGCCGCCGTTCGTCTAGCGGCGATGCAGTACTGC
```

```
ATGAAGTACCATGACCTGCGGGACTTCTTGACGTTGCTGGAACAACAAGGTGAGTTGAAA
CGCATCACTCTGCCTGTCGATCCACATCTGGAGATCACGGAAATTGCCGATAGAACGCTG
CGTGCAGGGGGCCCGGCCCTTTTGTTCGAAAACCCGAAAGGTTACACCATGCCGGTGTTG
TGCAACCTATTCGGCACGCCGCGGCGCGTGGCCCTAGGCATGGGCCAAGAAGACGTCTCA
TCGCTACGTGAAGTGGGGAAATTGCTAGCGTTCTTGAAAGAACCGGAACCGCCGAAGGGC
TTCCGCGATCTGTTTGACAAATTGCCTCAATTCAAGCAAGTGCTTAATATGCCAACCAAA
CGTCTGCGCGGCGCGCCCTGCCAACAAAAAATTATCCAAGGTGACGACGTCGACCTTAAC
AAAATTCCGATCATGACTTGCTGGCCGGAAGACGCTGCGCCACTGATCACGTGGGGCCTG
ACCGTCACACGCGGCCCTCACAAAGAACGTCAAAACTTGGGGATCTATCGTCAGCAACTG
ATAGGCAAGAACAAACTGATCATGCGTTGGTTGTCGCATCGGGGTGGCGCGCTGGACTTT
CAAGAGTGGTGCGCGGCGCGGCCGGGCGAACGATTCCCTGTCTCCGTCGCTCTGGGCGCC
GACCCGGCTACCATCTTGGGAGCCGTTACCCCAGTCCCCGATACTTTGAGTGAGTATGCC
TTCGCGGGTCTCTTGCGTGGGACCAAAACCGAAGTTGTCAAATGCGTGTCCAACGACCTC
GAAGTGCCTGCCTCTGCTGAAATAGTGCTCGAAGGTTACATCGAGGCCGGAGAAATGGCT
CCCGAAGGTCCATACGGAGACCATACCGGATATTACAACGAAGTAGACCAATTCCCGGTC
TTCACTGTAACTCATATCACCCAACGTGAAGACGCCATCTACCATAGCACCTACACCGGC
CGCCCGCCTGACGAACCGGCTGTCTTAGGGGTGGCGTTGAACGAGGTATTCGTCCCGATC
TTGCAAAAACAGTTCCCTGAGATCGTGGACTTTTACTTGCCTCCGGAAGGGTGTTCGTAC
CGTCTTGCGGTTGTGACGATGAAAAAACAGTACGCCGGTCATGCTAAACGGGTTATGATG
GGCGTATGGTCGTTCTTGCGTCAATTCATGTACACCAAATTCGTAATTGTTTGCGACGAC
GACGTGAACGCGCGCGATTGGAACGATGTCATTTGGGCTATCACCACTCGTATGGACCCA
GCCCGCGATACCGTTCTGGTCGAAAACACCCCGATCGACTACCTCGACTTCGCCTCCCCG
GTTTCAGGCTTGGGCTCTAAAATGGGCTTGGACGCTACAAACAAATGGCCAGGTGAGACG
CAACGCGAATGGGGTCGTCCGATCAAGAAAGACCCGGCCGTGACTGCTAGGATCGATGCA
ATCTGGGACGAACTCGCCATATTTAAACAACAG
```

ATGGAAGTTAAAATCTTCAACACGCAGGACGTGCAAGACTTCTTGCGCGTGGCCTCAGGT
CTGGAGCAAGAAGGTGGTAACCCACGTGTTAAGCAAATCATCCATCGGGTATTGTCGGAC
CTGTACAAAGCCATCGAGGATTTGAACATCACCTCTGACGAGTACTGGGCGGGTGTTGCC
TACTTAAACCAGTTGGGCGCGAACCAGGAAGCCGGGCTGTTGTCACCTGGTCTTGGCTTC
GACCATTACTTGGATATGCGAATGGACGCGGAAGACGCGGCCCTAGGGATTGAAAACGCG
ACGCCCAGGACAATCGAAGGGCCGCTGTACGTTGCGGGCGCGCCTGAGAGTGTGGGGTAT
GCCCGTATGGACGACGGCTCTGACCCGAACGGCCATACCCTAATCCTGCACGGTACAATC
TTCGACGCCGACGGAAAACCTCTGCCCAATGCGAAGGTCGAAATTTGGCATGCTAATACG
AAAGGATTCTACTCACACTTCGACCCTACTGGTGAGCAGCAAGCCTTCAACATGCGCCGA
AGTATCATCACCGACGAAAACGGTCAATACAGGGTGCGCACCATCCTGCCCGCAGGTTAC
GGCTGCCCCCGGAAGGCCCAACGCAACAACTTTTGAACCAACTGGGCCGCCATGGCAAC
CGTCCCGCTCATATACATTACTTCGTTTCGGCGGACGGTCATCGCAAACTGACTACCCAA
ATCAACGTAGCCGGAGACCCGTACACGTACGACGACTTCGCGTACGCCACTCGCGAGGGC
TTGGTCGTTGACGCGGTGGAACATACGGACCCGGAAGCTATCAAAGCTAACGACGTCGAA
GGTCCTTTCGCGGAAATGGTCTTCGACTTGAAACTGACGCGGTTGGTCGACGGTGTTGAC
AACCAAGTCGTGGACCGTCCGCGCCTGGCCGTT

B.

MEVKIFNTQDVQDFLRVASGLEQEGGNPRVK
QIIHRVLSDLYKAIEDLNITSDEYWAGVAYL
NQLGANQEAGLLSPGLGFDHYLDMRMDAEDA
ALGIENATPRTIEGPLYVAGAPESVGYARMD
DGSDPNGHTLILHGTIFDADGKPLPNAKVEI
WHANTKGFYSHFDPTGEQQAFNMRRSIITDE
NGQYRVRTILPAGYGCPPEGPTQQLLNQLGR
HGNRPAHIHYFVSADGHRKLTTQINVAGDPY
TYDDFAYATREGLVVDAVEHTDPEAIKANDV
EGPFAEMVFDLKLTRLVDGVDNQVVDRPRLA
V

```
ATGAACTACCAAAACGACGACTTGAGGATCAAAGAAATCAAAGAATTGTTGCCGCCGGTC
GCGCTTTTGGAGAAATTCCCTGCCACCGAGAACGCTGCTAACACCGTGGCGCATGCGAGA
AAAGCTATTCATAAAATCCTGAAGGGCAACGATGACCGTTTGTTGGTAGTGATCGGGCCT
TGTAGTATCCATGACCCGGTCGCCGCCAAAGAATATGCGACCCGCTTGCTGGCTCTGCGT
GAGGAACTGAAAGACGAACTGGAAATCGTAATGAGAGTCTACTTCGAAAAGCCTCGCACT
ACCGTCGGTTGGAAAGGCCTTATAAACGACCCTCACATGGACAATTCTTTCCAAATCAAC
GACGGCTTGCGTATCGCGCGTAAACTGCTTCTAGACATTAACGACTCTGGCTTGCCTGCC
GCAGGTGAATTCTTAAACATGATAACTCCACAATACTTGGCCGACCTGATGAGTTGGGGT
GCCATTGGCGCCAGAACTACAGAATCCCAAGTGCACCGGGAATTGGCGAGCGGCCTATCT
TGTCCGGTGGGCTTCAAAAACGGCACCGACGGCACGATCAAGGTCGCCATTGATGCTATC
AACGCGGCCGGCGCCCCGCATTGTTTCCTGTCGGTTACGAAATGGGGCATAGCGCCATC
GTAAACACGTCAGGCAATGGGGACTGTCATATCATACTGCGGGGTGGCAAAGAACCGAAC
TACTCTGCTAAACATGTAGCTGAAGTCAAAGAGGGTTTGAACAAAGCTGGCCTACCGGCG
CAAGTCATGATCGATTTTAGCCATGCGAACTCGTCTAAGCAATTCAAAAAACAAATGGAC
GTTTGCGCGGACGTTTGCCAACAGATCGCCGGAGGAGAAAAAGCCATAATCGGCGTAATG
GTTGAATCGCACCTGGTTGAAGGAAACCAATCGCTGGAATCGGGTGAACCTCTGGCTTAC
GGTAAATCTATAACAGACGCGTGTATAGGCTGGGAGGACACAGACGCCCTGCTGCGTCAA
TTGGCGAATGCTGTCAAAGCCCGAAGGGGC
```

A.
ATGCAAACGCAAAAACCTACCTTGGAATTATTAACGTGCGAAGGTGCCTACCGCGACAAC
CCTACTGCCTTGTTCCATCAATTGTGCGGTGACCGTCCAGCCACTTTGCTACTAGAAAGG
GCAGACATCGACTCGAAGGATGATCTTAAATCGCTACTGTTAGTGGACTCAGCGTTGCGT
ATCACGGCTCTGGGTGACACTGTGACTATCCAAGCGTTGTCGGGTAACGGCGAAGCGCTG
TTAGCCCTCCTGGACAACGCTTTACCCGCCGGTGTCGAATCTGAACAATCGCCCAACTGC
AGAGTCTTGCGTTTCCCACCGGTCTCGCCGTTGCTGGACGAGGACGCTCGTCTGTGTTCG
TTGTCTGTTTTCGACGCCTTCAGGCTGTTGCAAAACCTCCTGAACGTCCCAAAAGAGGAA
CGAGAAGCGATGTTTTTCGGTGGCTTGTTCAGCTACGACTTGGTTGCGGGATTCGAAGAC
CTGCCCCAATTGTCTGCCGAAAACAATTGCCCGGACTTCTGCTTTTACTTGGCCGAAACC
CTAATGGTGATTGACCATCAGAAAAAGTCGACTCGCATACAAGCGTCTCTGTTCGCGCCT
AACGAAGAGGAAAAACAGCGTTTGACTGCACGGCTGAACGAATTACGCCAGCAGCTGACG
GAAGCGGCCCCACCATTGCCGGTCGTTTCGGTCCCACATATGCGGTGTGAATGTAACCAA
TCGGACGAAGAATTCGGCGGTGTTGTCCGTCTGCTGCAAAAAGCCATCCGCGCCGGGGAA
ATATTCCAAGTTGTCCCGTCAAGAAGATTTTCCCTCCCATGCCCTAGTCCTCTTGCTGCC
TACTACGTCCTCAAAAAATCTAACCCAAGCCCCTACATGTTCTTCATGCAAGACAACGAT
TTTACTCTGTTCGGGGCGTCGCCTGAATCGTCGCTGAAATACGACGCGACCTCGCGCCAG
ATCGAGATCTACCCTATAGCGGGCACGCGCCCACGTGGCCGTAGAGCCGACGGCTCGCTA
GATCGCGACCTGGATAGCCGCATCGAACTGGAAATGCGAACGGACCATAAGGAACTTAGT
GAGCATCTGATGTTGGTGGACCTCGCCCGTAATGACCTAGCGCGTATCTGCACGCCTGGT
TCGCGATATGTCGCCGACTTGACCAAAGTGGACCGTTACTCTTACGTCATGCATCTGGTC
TCTCGTGTGGTAGGAGAATTGCGCCACGACCTCGACGCTCTCCATGCGTACCGCGCTTGC
ATGAACATGGGCACGCTCTCGGGCGCCCAAAAGTCCGAGCTATGCAATTGATCGCGGAA
GCTGAAGGGCGCCGTCGTGGTTCCTACGGCGGGGCGGTTGGCTACTTCACTGCTCATGGC
GACCTAGACACCTGCATCGTGATACGTAGTGCTCTCGTCGAAAACGGCATCGCTACAGTG
CAAGCCGGAGCGGGTGTTGTCCTTGACTCTGTTCCGCAATCAGAAGCTGATGAAACTCGT
AATAAAGCGCGTGCGGTGCTGCGTGCTATCGCTACGGCTCACCATGCTCAAGAAACGTTC

ATGTCAGAAAAATTCAAGTACATCCGTTGGTTTGAGGAACTAACGATCGA
CGATATTCCCTTGGTTGGCGGCAAGAATGCCTCGCTGGGCGAAATGTACC
TCGAACTAGCCACCGAAGGCATCCGCGTGCCGAACGGCTTCGCGATTACT
GCGGAAGGTTACCGGCACATGCTCGATAAAGCGGATGCCTGGGAAGCCTT
ACATGAGGCGCTCGATACCTTGAATCCGGACGATGTGAACGACTTGGCTA
AGCGAGCCAGAAAAGCGCGAGATATCGTTTACGCGGCGCCGCTATCCGAA
GACTTGGAGCATGAAATTCTGATTGCTTTCGATCAACTGCAGCGACAATA
CGATGAGGAATTGACCGTTGCGGTTAGAAGTTCGGCGACGGCCGAGGATT
TGCCGACCGCGAGCTTTGCGGGTCAGCAGGACACCTATCTGAACGTGCAT
AGCGGACAGGCTCTGCTCGATGCGTGTAAACGCTGTTTCGCGAGCCTGTT
CACCGATCGGGCGATTCATTATCGGATCGATCAAGGTTTCGATCATTTCA
AGGTGTCGTTATCGATCGGCGTGATGAAAATGGTCCGTTCGGATTTGGCG
TCGAGCGGCGTAATGTTCTCGATCGATACCGAATCGGGCTTCAAAGATGC
GGTATTCATTACCGGTGCTTACGGCCTCGGTGAAAATGTCGTGCAGGGTT
CGGTCGACCCGGACGAGTTTTATGTGCATAAGCCTACCTTCGAGCAAGGT
CATCGTTGTGTGTTGCGACGGTCGCTGGGCGCGAAAAAATTAAGATGGT
CTATAGCGAAGGCCGTACGCGCGAGCAAACTTGTAATGTCGTGACGTCAG
CCGAGGAGCGTTCGCAATTTTGCTTGAGCGACGACGAGGTGCTGACTTTG
GCCGATTACGCGATCAAGATCGAGAAGCACTACAGCGCGAAGGCTGGCAT
GCCCAGGCCAATGGATATCGAATGGGCGAAGGACGGGCTGGACGGACAAC
TCTATATCGTACAGGCACGGCCCGAAACAGTCGCATCGCAGTTGAGCGGG
ACGACGCTCGAACAATACGAACTGAAACAAAAGGCCGAGGCGATTGTGAC
AGGACGAGCGGTCGGCAGCAAGATCGCGGTCGGTACCGCGCATGTGATCA
AAAATGTCAGCCAATTGAATACCTTCAAACCCGGCGAAGTGTTGATTACC
GACATGACCACACCGGATTGGGAACCGGTCATGAAAACGGCCGCAGCGAT
CGTGACCAATCGAGGTGGGCGCACCTGTCATGCCGCAATCATCGCTCGCG
AGCTGGGTGTTCCGGCCGTGATCGGCTGCGACAATGCGACCGAAACGATT
AAAACCGGTACGACTGTCACGGTATCCTGCGCCGAAGGCGATGCCGGCAA
GGTTTATGACGGCGAGTTGAGTTTCGATGTCAATAAGACCGATCTTTCCG
GATTGAAGCGACCGAAAACTAAAATTATGCTGAATTTGGGCAATCCGGAA
TTGGCATTCAAACTCAGCTTTTTGCCGAATGACGGCGTCGGATTGGCGCG
GATGGAATTCATCATTACCGAGTTTATCAAGGCTCATCCGATGGCGTTGA
TTCATCCTGAACGCATACAAGATGCCGAAGAAAAGCAAAGATTAAACGC
TTGACCCGCTATTATGCGCAGCCGGAGGATTTTTTCATCGAGCGTCTTGC
GGAGGGAGTCGGTACGATCGCTGCAGCGTTTTATCCGAAGCCGGTCGTGG
TCAGAATGTCCGACTTCAAGACTAATGAGTATGCAACCTTGCTCGGCGGT
CGCGGGTCGAGCGCGACGAGGCGAATCCGATGATCGGTTTCAGAGGCGC
TTCGCGTTATGTGCATCCCGATTATAAGGAAGGCTTCGCACTCGAATGCC
GAGCGATGAAGCGGGTTCGCGAAGACATGGGTTTGACCAACGTGATTCTT
ATGATTCCGTTTTGCCGCCGGGAGCAAGAAGCGGTGCGCGTTTTGGATTA
TATGGCCGAGCTCGGTTTGAAAAGAGGGGAGAACGGACTCGAAATTTATG
TGATGTGCGAAATTCCGAATAATGTGATTCGTATCGATGCGTTTTCGAAG
CTGTTCGACGGATTTTCGATCGGCTCGAACGATTTGACACAATTGACGCT
CGGCGTCGATAGGGATTCCGAAATACTTGCCGAAGATTTCGATGAGCGCG
ATCCGGGCGTTAAAGAAATGATTCGTATGGCTGTGGAAGGCGCGCGCCGT
AACGGCAAGCATTCCGGCTTGTGCGGGCAGGCGCCATCCGATTATCCGGA
AATGGCCGAATACCTAGTCGAAATTGGCATCGATTCGATGAGTTTGAATC
CGGATACGGTGTTGCAGACGACCCAGCGGATTTTGAAAATGGAAGAACAA
TTAAAAGGG

ATGCCTTCGCGCCGAGACTTAGCGAACGCCATACGCGCTTTGAGCATGGA
TGCCGTCCAAAAAGCCAACTCCGGACACCCGGGCGCACCGATGGGGATGG
CGGATATCGCCGAGGTGTTATGGAACGACTTCCTGCAGCATAACCCGACT
AACCCGAACTGGGCCAACCGAGACCGCTTCGTACTGTCTAACGGCCACGG
CTCGATGCTGCTGTACTCGTTACTGCATCTGACAGGTTACCAGCTGCCGA
TCGACGAACTGAAACAATTCCGTCAACTGCATTCAAAAACCCCGGGTCAT
CCGGAATACGGCTATGCGCCGGGCGTCGAAACGACGACCGGACCATTAGG
TCAAGGCATCACCAATGCCGTGGGCTTTGCGATAGCCGAACGCGCACTAG
CGGGTCAATTTAACCGTCCCGGACACGAAATCGTCGACCATTACACCTAC
GCCTTCCTGGGCGACGGCTGTTTAATGGAAGGCATCTCGCATGAAGCCTG
CTCATTGGCCGGCTCGATGAAACTGGGCAAACTGATTGCCGTCTACGACG
ACAACAACATCTCGATCGACGGCGAAGTCCGCGGTCACGGCGACACGCCG
GGCTGGTTCCTGGACGACACGCCGAAACGCTTCGAAGCCTACGGCTGGCA
CGTCATCCCGAAAGTAGACGGCCATAACCCTGAAGCCGTCAAAAAAGCCT
TGGAAGAAGCGCGTAGCGTCACTGATCGGCCGACCTTGATCTGCTGCCAA
ACCATCATTGGCTGGGGCTCGCCGAATAAAGAAGGCAAAGAAGAATGTCA
TGGAGCGGCATTAGGCGAAGCCGAAATCACGGCAACCCGCGAACGCATCG
GTTGGCCGCATGCACCTTTCGAAATCCCGGCGGATATTTACGCGGGTTGG
GATGCGAAAGACAAAGGCGCGCGTCAAGAAGCGGAGTGGAACGACAAATT
CGCGAAATACCAAGCAGCGCATCCGGAACTGGCGGCCGAATTCGAACGCC
GCATGAGCGGACAGCTGCCGAGCGACTGGTCGGAAAAAGCGAACGCCTTC
ATTGCTGCGGTCGACGCGAAAGGCGAAACCATCGCTAGCCGCAAAGCCTC
ACAAAACACCCTGAACGGATTCGGACCGTTACTGCCCGAACTGATGGGCG
GCTCGGCGGACTTGGCAGGCTCCAACTTGACCCTGTGGTCGGGTTGCAAA
GACGTCAACGCCCCGGGACATGACGGCAACTACGTCTACTACGGCGTCCG
TGAATTCGGCATGTCGGCGATCATGAACGGCATCACCCTGCATGGCGGCT
TCAAGCCGTACGGCGCGACCTTCCTGATGTTCTCCGAATATGCGCGGAAT
GCCTTGCGGATGGCGTCGTTGATGAAATCCCGACCATCTTCGTATACAC
GCACGACTCGATCGGCTTAGGCGAAGACGGCCCGACCCATCAACCGATCG
AACAAACCGCGACCTTGCGGATGATTCCAAACATGCAAGTGTGGCGTCCA
TGTGATGCTGTGGAATCGGCGGTGTCGTGGAAAGCGGCGATTGAACGAAA
CGATGGACCGAGTTGTCTGATCTTCTCACGGCAAAACCTAGCGCACATTG
CGCGGACGCCGGCGCAGATCGAAGCGATCAACAAAGGCGGCTACATTCTG
AAAGACAGCGAAGGTCAGCCGGACGTGATCCTGATTGCGACGGGCTCGGA
AGTCGAATTGGCGGTGAAAGCGGCAGACGAGTTGAGCGGCAAAGGCAAAA
AAGTGCGGGTCGTCTCGATGCCATCGACCAACGTATTCGATGCGCAGGAC
GAAGCCTACCGTGAGTCGGTGCTGCCGTCATCGGTGACAAAACGCGTCGT
AATTGAAGCGGGCGTGACCGACAGCTGGTGGAAATACGCGGGTACACAAG
GTTGCGTCATCGGAATGGATCGTTTCGGCGAATCGGCACCGGCCGGCGCG
CTGTTCAAAGAGTTCGGCTTCACCGTTGACAATGTCGTCAAACACGTCGA
AGCTCTGCTT

RuMP-EMP: $3CH_2O \rightarrow AcCoA + CO_2 + 2NADH + 2ATP$
RuMP-Pkt: $3CH_2O \rightarrow 1.5AcCOA$

FIGURE 18
A.
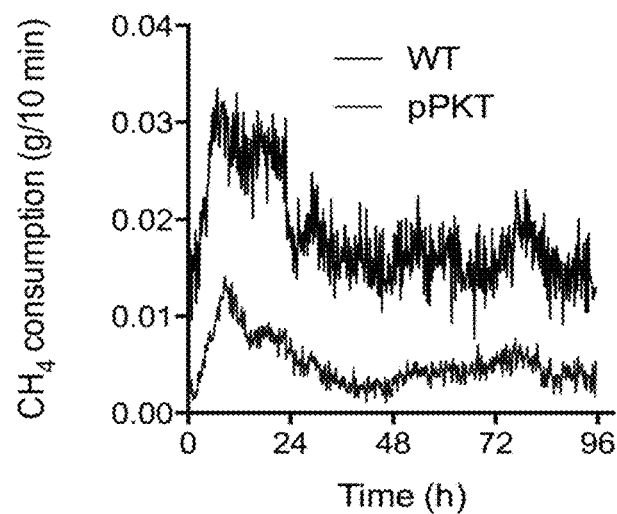
B.
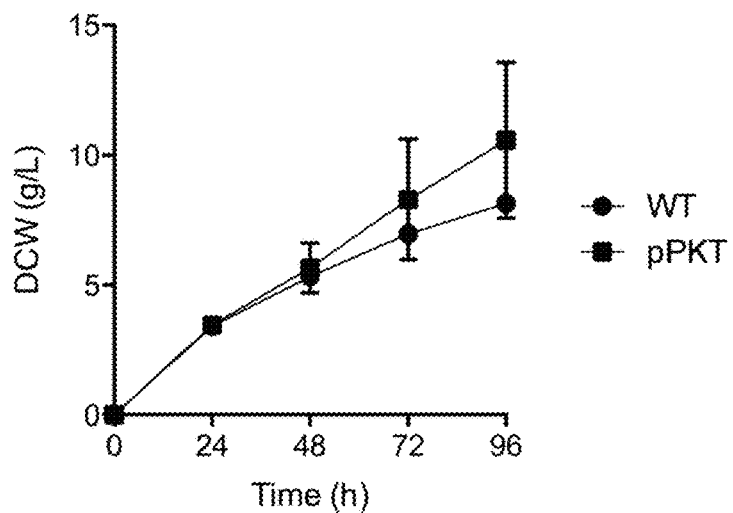
C.
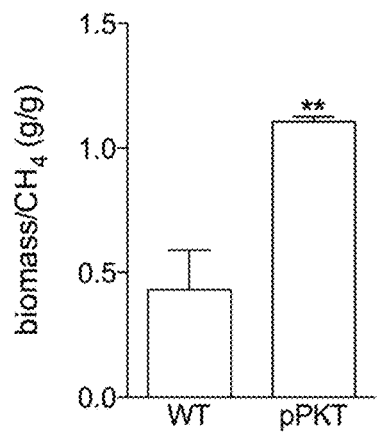

SEQUENCE LISTING

```
<160> NUMBER OF SEQ ID NOS: 40

<210> SEQ ID NO 1
<211> LENGTH: 1851
<212> TYPE: DNA
<213> ORGANISM: Podospora anserina
<220> FEATURE:
<221> NAME/KEY: CDS
<222> LOCATION: (1)..(1851)

<400> SEQUENCE: 1 atg ctg agg tcg atc gct aca gtc tca ata tcg ggc acc cta cca gaa        48
```

```
Met Leu Arg Ser Ile Ala Thr Val Ser Ile Ser Gly Thr Leu Pro Glu
1               5                   10                  15 aaa ttg cac gcg ata gcg gct gcg gga tac cag ggc gtc gaa atc ttc       96
Lys Leu His Ala Ile Ala Ala Ala Gly Tyr Gln Gly Val Glu Ile Phe
                20                  25                  30 gaa aac gac ttg ctg tat tac act ggt act cca gcc gag atc agg cag      144
Glu Asn Asp Leu Leu Tyr Tyr Thr Gly Thr Pro Ala Glu Ile Arg Gln
            35                  40                  45 cta gcg gcg gac cta ggt ctt aaa atc acc ttg ttc caa ccg ttc cgt      192
Leu Ala Ala Asp Leu Gly Leu Lys Ile Thr Leu Phe Gln Pro Phe Arg
50                  55                  60 gac ttc gaa ggt gcc tcg cgt gcc cag ttc gct gcg aac atg gcg agg      240
Asp Phe Glu Gly Ala Ser Arg Ala Gln Phe Ala Ala Asn Met Ala Arg
65                  70                  75                  80 gcg cga cgc aaa ttc gcg tta atg cgt gaa ttg ggt tgc gaa act ttg      288
Ala Arg Arg Lys Phe Ala Leu Met Arg Glu Leu Gly Cys Glu Thr Leu
                85                  90                  95 ctt ttg tgt agc aat gtc caa cct gac tgc agc gcg gac tcg gaa ctg      336
Leu Leu Cys Ser Asn Val Gln Pro Asp Cys Ser Ala Asp Ser Glu Leu
            100                 105                 110 caa gtt gct gat tta cgt gcc ttg gcc acc ttg gcc gaa gaa gaa ggt      384
Gln Val Ala Asp Leu Arg Ala Leu Ala Thr Leu Ala Glu Glu Glu Gly
        115                 120                 125 atc gcg att ggg tac gaa gcg ctg gcc tgg ggc act cat gtt aac cgt      432
Ile Ala Ile Gly Tyr Glu Ala Leu Ala Trp Gly Thr His Val Asn Arg
130                 135                 140 tgg caa caa gcc tgg gaa cga gtg cgt agg gtc gac tcc ccg gcg ttg      480
Trp Gln Gln Ala Trp Glu Arg Val Arg Arg Val Asp Ser Pro Ala Leu
145                 150                 155                 160 ggg ctg gtt ttg gac tct ttc cac ata ctg gct cgc ggt gac aca ctt      528
Gly Leu Val Leu Asp Ser Phe His Ile Leu Ala Arg Gly Asp Thr Leu
                165                 170                 175 gac gcg ctg cct tca gtc ccg gtc gaa aaa atc acg ttt gtt caa tta      576
Asp Ala Leu Pro Ser Val Pro Val Glu Lys Ile Thr Phe Val Gln Leu
            180                 185                 190 gct gat gcc cca tat atg aaa atg gac cta ctg gaa tgg tca agg cat      624
Ala Asp Ala Pro Tyr Met Lys Met Asp Leu Leu Glu Trp Ser Arg His
        195                 200                 205 ttc cgg tgt ttc ccc ggt caa gga gaa ttg cca ctg gaa gca ttc gcc      672
Phe Arg Cys Phe Pro Gly Gln Gly Glu Leu Pro Leu Glu Ala Phe Ala
210                 215                 220 gaa caa att acg cgg tgc ggg tat cgt ggc cca tgg agc ctc gag atc      720
Glu Gln Ile Thr Arg Cys Gly Tyr Arg Gly Pro Trp Ser Leu Glu Ile
225                 230                 235                 240 ttc aat gac ggc ttc cgt gcc agc ccc aat ggc gcg acg gcc aaa gac      768
Phe Asn Asp Gly Phe Arg Ala Ser Pro Asn Gly Ala Thr Ala Lys Asp
                245                 250                 255 ggc tac cgt tct tta ttg tgg ttg gaa gaa caa acg cgc agg cgt ctg      816
Gly Tyr Arg Ser Leu Leu Trp Leu Glu Glu Gln Thr Arg Arg Arg Leu
            260                 265                 270 cct acg tgc gac gcg gac ctt ttc tct cct cct ccg ctt cca gtc tac      864
Pro Thr Cys Asp Ala Asp Leu Phe Ser Pro Pro Pro Leu Pro Val Tyr
        275                 280                 285 cat ggc ttg gag ttc atc gaa ttc gcg gct tca gcc gct gaa gcc caa      912
His Gly Leu Glu Phe Ile Glu Phe Ala Ala Ser Ala Ala Glu Ala Gln
290                 295                 300 cgc ctg ggc caa cac ttg caa gcg ttg ggg ttc caa cat gaa ggc tct      960
Arg Leu Gly Gln His Leu Gln Ala Leu Gly Phe Gln His Glu Gly Ser
305                 310                 315                 320
```

```
cat cgt agc cgc cga gtt act ctc tgg cgc aac ggc ggt gct cgc atc      1008
His Arg Ser Arg Arg Val Thr Leu Trp Arg Asn Gly Gly Ala Arg Ile
            325                 330                 335 gtt atc aac cat caa ccg cat agc tgg gcg gac cat ttc tac caa cga      1056
Val Ile Asn His Gln Pro His Ser Trp Ala Asp His Phe Tyr Gln Arg
            340                 345                 350 cat ggt gtc tct ttg tgt gcg atg gct cta cgt gtt gag cat tcg gct      1104
His Gly Val Ser Leu Cys Ala Met Ala Leu Arg Val Glu His Ser Ala
            355                 360                 365 tct ctg gtt gcg cgc gct cga gct ctg ggc tac gcg acg tgg caa ggc      1152
Ser Leu Val Ala Arg Ala Arg Ala Leu Gly Tyr Ala Thr Trp Gln Gly
            370                 375                 380 gac gcg ggc cct aac gaa acg cca ata ccg gcg atc tgc gcc ccg gac      1200
Asp Ala Gly Pro Asn Glu Thr Pro Ile Pro Ala Ile Cys Ala Pro Asp
385                 390                 395                 400 ggt tct ttg atc tat tta att gat gcc ggc gag gct ata tac gaa cga      1248
Gly Ser Leu Ile Tyr Leu Ile Asp Ala Gly Glu Ala Ile Tyr Glu Arg
                405                 410                 415 gac ttt cat cta cgt gac ggt gtt act gtg cgt gag gac tac ctt ggc      1296
Asp Phe His Leu Arg Asp Gly Val Thr Val Arg Glu Asp Tyr Leu Gly
                420                 425                 430 ata gac cat tta gcg ttg ggt atg gaa gct gac tcg cgc gat aac tgg      1344
Ile Asp His Leu Ala Leu Gly Met Glu Ala Asp Ser Arg Asp Asn Trp
            435                 440                 445 gtt atg ttc ttc cgc acc gtg ttc ggt ttc tcg ctc gag cat gag caa      1392
Val Met Phe Phe Arg Thr Val Phe Gly Phe Ser Leu Glu His Glu Gln
    450                 455                 460 acg ttg ccg gac cca tat ggg ttg gtt cgc tcg cta gcc gtt cgc tcg      1440
Thr Leu Pro Asp Pro Tyr Gly Leu Val Arg Ser Leu Ala Val Arg Ser
465                 470                 475                 480 cct cag ggt gac atc cgt ctg gcg tta aac atc agt caa tct cga gcg      1488
Pro Gln Gly Asp Ile Arg Leu Ala Leu Asn Ile Ser Gln Ser Arg Ala
                485                 490                 495 acc caa atc gct cgc tcg gtt gcc tgc tac caa ggc gct ggc ttg caa      1536
Thr Gln Ile Ala Arg Ser Val Ala Cys Tyr Gln Gly Ala Gly Leu Gln
            500                 505                 510 cat gcc gct ttt gcc tgt cgg gac ctg cct gcc gcc tgt gat caa ctg      1584
His Ala Ala Phe Ala Cys Arg Asp Leu Pro Ala Ala Cys Asp Gln Leu
            515                 520                 525 gca gaa gtg gct cgt cat acg ttg ccg att cca gct aac tac tac gac      1632
Ala Glu Val Ala Arg His Thr Leu Pro Ile Pro Ala Asn Tyr Tyr Asp
    530                 535                 540 gat cta ctt gcg cga ttc ggc ggc gaa ctg gac gtg ggg caa cta caa      1680
Asp Leu Leu Ala Arg Phe Gly Gly Glu Leu Asp Val Gly Gln Leu Gln
545                 550                 555                 560 cgg caa cag tta ctc tac gat cgc gac ccg caa ggc ggc gac ttc ctg      1728
Arg Gln Gln Leu Leu Tyr Asp Arg Asp Pro Gln Gly Gly Asp Phe Leu
                565                 570                 575 cat ttg tac act cga ccg ttc act gca ggc aga ttc ttc gaa ttg          1776
His Leu Tyr Thr Arg Pro Phe Thr Ala Gly Arg Phe Phe Glu Leu
            580                 585                 590 act gaa cgt cga gcg ggc tac gcc ttg tac ggt gcg gcg aac gcc gcc      1824
Thr Glu Arg Arg Ala Gly Tyr Ala Leu Tyr Gly Ala Ala Asn Ala Ala
                595                 600                 605 gtt cgt cta gcg gcg atg cag tac tgc                                  1851
Val Arg Leu Ala Ala Met Gln Tyr Cys
        610                 615

<210> SEQ ID NO 2
<211> LENGTH: 617
```

<212> TYPE: PRT
<213> ORGANISM: Podospora anserina

<400> SEQUENCE: 2

```
Met Leu Arg Ser Ile Ala Thr Val Ser Ile Ser Gly Thr Leu Pro Glu
1               5                   10                  15

Lys Leu His Ala Ile Ala Ala Gly Tyr Gln Gly Val Glu Ile Phe
            20                  25                  30

Glu Asn Asp Leu Leu Tyr Tyr Thr Gly Thr Pro Ala Glu Ile Arg Gln
            35                  40                  45

Leu Ala Ala Asp Leu Gly Leu Lys Ile Thr Leu Phe Gln Pro Phe Arg
50                  55                  60

Asp Phe Glu Gly Ala Ser Arg Ala Gln Phe Ala Ala Asn Met Ala Arg
65                  70                  75                  80

Ala Arg Arg Lys Phe Ala Leu Met Arg Glu Leu Gly Cys Glu Thr Leu
                85                  90                  95

Leu Leu Cys Ser Asn Val Gln Pro Asp Cys Ser Ala Asp Ser Glu Leu
            100                 105                 110

Gln Val Ala Asp Leu Arg Ala Leu Ala Thr Leu Ala Glu Glu Glu Gly
            115                 120                 125

Ile Ala Ile Gly Tyr Glu Ala Leu Ala Trp Gly Thr His Val Asn Arg
130                 135                 140

Trp Gln Gln Ala Trp Glu Arg Val Arg Arg Val Asp Ser Pro Ala Leu
145                 150                 155                 160

Gly Leu Val Leu Asp Ser Phe His Ile Leu Ala Arg Gly Asp Thr Leu
                165                 170                 175

Asp Ala Leu Pro Ser Val Pro Val Glu Lys Ile Thr Phe Val Gln Leu
            180                 185                 190

Ala Asp Ala Pro Tyr Met Lys Met Asp Leu Leu Glu Trp Ser Arg His
            195                 200                 205

Phe Arg Cys Phe Pro Gly Gln Gly Glu Leu Pro Leu Glu Ala Phe Ala
210                 215                 220

Glu Gln Ile Thr Arg Cys Gly Tyr Arg Gly Pro Trp Ser Leu Glu Ile
225                 230                 235                 240

Phe Asn Asp Gly Phe Arg Ala Ser Pro Asn Gly Ala Thr Ala Lys Asp
                245                 250                 255

Gly Tyr Arg Ser Leu Leu Trp Leu Glu Glu Gln Thr Arg Arg Leu
            260                 265                 270

Pro Thr Cys Asp Ala Asp Leu Phe Ser Pro Pro Leu Pro Val Tyr
            275                 280                 285

His Gly Leu Glu Phe Ile Glu Phe Ala Ala Ser Ala Ala Glu Ala Gln
290                 295                 300

Arg Leu Gly Gln His Leu Gln Ala Leu Gly Phe Gln His Glu Gly Ser
305                 310                 315                 320

His Arg Ser Arg Arg Val Thr Leu Trp Arg Asn Gly Gly Ala Arg Ile
                325                 330                 335

Val Ile Asn His Gln Pro His Ser Trp Ala Asp His Phe Tyr Gln Arg
            340                 345                 350

His Gly Val Ser Leu Cys Ala Met Ala Leu Arg Val Glu His Ser Ala
            355                 360                 365

Ser Leu Val Ala Arg Ala Arg Ala Leu Gly Tyr Ala Thr Trp Gln Gly
370                 375                 380

Asp Ala Gly Pro Asn Glu Thr Pro Ile Pro Ala Ile Cys Ala Pro Asp
385                 390                 395                 400
```

```
Gly Ser Leu Ile Tyr Leu Ile Asp Ala Gly Glu Ala Ile Tyr Glu Arg
                405                 410                 415

Asp Phe His Leu Arg Asp Gly Val Thr Val Arg Glu Asp Tyr Leu Gly
                420                 425                 430

Ile Asp His Leu Ala Leu Gly Met Glu Ala Asp Ser Arg Asp Asn Trp
                435                 440                 445

Val Met Phe Phe Arg Thr Val Phe Gly Phe Ser Leu Glu His Glu Gln
    450                 455                 460

Thr Leu Pro Asp Pro Tyr Gly Leu Val Arg Ser Leu Ala Val Arg Ser
465                 470                 475                 480

Pro Gln Gly Asp Ile Arg Leu Ala Leu Asn Ile Ser Gln Ser Arg Ala
                485                 490                 495

Thr Gln Ile Ala Arg Ser Val Ala Cys Tyr Gln Gly Ala Gly Leu Gln
                500                 505                 510

His Ala Ala Phe Ala Cys Arg Asp Leu Pro Ala Ala Cys Asp Gln Leu
                515                 520                 525

Ala Glu Val Ala Arg His Thr Leu Pro Ile Pro Ala Asn Tyr Tyr Asp
    530                 535                 540

Asp Leu Leu Ala Arg Phe Gly Gly Glu Leu Asp Val Gly Gln Leu Gln
545                 550                 555                 560

Arg Gln Gln Leu Leu Tyr Asp Arg Asp Pro Gln Gly Gly Asp Phe Leu
                565                 570                 575

His Leu Tyr Thr Arg Pro Phe Thr Ala Gly Arg Phe Phe Phe Glu Leu
                580                 585                 590

Thr Glu Arg Arg Ala Gly Tyr Ala Leu Tyr Gly Ala Ala Asn Ala Ala
                595                 600                 605

Val Arg Leu Ala Ala Met Gln Tyr Cys
    610                 615

<210> SEQ ID NO 3
<211> LENGTH: 1851
<212> TYPE: DNA
<213> ORGANISM: Klebsiella variicola
<220> FEATURE:
<221> NAME/KEY: CDS
<222> LOCATION: (1)..(1851)

<400> SEQUENCE: 3 atg ctg cgc tct atc gcc acc gtt tcg att tcc ggc acc ctg cct gag      48
Met Leu Arg Ser Ile Ala Thr Val Ser Ile Ser Gly Thr Leu Pro Glu
1               5                   10                  15 aag ctg cac gct att gcg gcg gcg ggc tat cag ggt gtg gaa att ttc      96
Lys Leu His Ala Ile Ala Ala Ala Gly Tyr Gln Gly Val Glu Ile Phe
            20                  25                  30 gag aac gat ctg ctc tat tat acg ggg acg ccg gcg gaa atc cgc cag     144
Glu Asn Asp Leu Leu Tyr Tyr Thr Gly Thr Pro Ala Glu Ile Arg Gln
        35                  40                  45 ctt gcc gcc gat tta ggg tta aaa atc acg ctt ttt caa ccc ttt cgc     192
Leu Ala Ala Asp Leu Gly Leu Lys Ile Thr Leu Phe Gln Pro Phe Arg
    50                  55                  60 gat ttt gaa ggc gcc agc cgg gcg cag ttt gcg gcg aat ata gcc cgc     240
Asp Phe Glu Gly Ala Ser Arg Ala Gln Phe Ala Ala Asn Ile Ala Arg
65                  70                  75                  80 gct cgg cgc aag ttt gcc ctg atg cac gag ctg ggc tgc gac acg ctg     288
Ala Arg Arg Lys Phe Ala Leu Met His Glu Leu Gly Cys Asp Thr Leu
                85                  90                  95 ctg ctg tgc agc aat gtg cag ccg gac tgc tcg gcg gat agc gaa ttg     336
```

|     |     |     |     |     |     |     |     |     |     |     |     |     |     |
| --- | --- | --- | --- | --- | --- | --- | --- | --- | --- | --- | --- | --- | --- |
| Leu | Leu | Cys | Ser | Asn | Val | Gln | Pro | Asp | Cys | Ser | Ala | Asp | Ser | Glu | Leu |
|     |     |     | 100 |     |     |     | 105 |     |     |     | 110 |     |     |

```
cag gtc gcg gat ctg cgg gcg ctg gcc acg ctg gcg gaa gaa gag ggg     384
Gln Val Ala Asp Leu Arg Ala Leu Ala Thr Leu Ala Glu Glu Glu Gly
        115                 120                 125 atc acc atc ggc tat gag gcg ctg gcc tgg gga acc cat gtg aac cgc     432
Ile Thr Ile Gly Tyr Glu Ala Leu Ala Trp Gly Thr His Val Asn Arg
    130                 135                 140 tgg cag cag gcc tgg gag cgg gta cgg cgg gtg gac agc ccg gcg ctg     480
Trp Gln Gln Ala Trp Glu Arg Val Arg Arg Val Asp Ser Pro Ala Leu
145                 150                 155                 160 ggc ctg gtg ctc gac agc ttc cat att ctg gct cgc ggc gac acg ctg     528
Gly Leu Val Leu Asp Ser Phe His Ile Leu Ala Arg Gly Asp Thr Leu
                165                 170                 175 gac gcg cta ccg tcg gtg ccg gtg gag aaa atc acc ttt gtt cag ctc     576
Asp Ala Leu Pro Ser Val Pro Val Glu Lys Ile Thr Phe Val Gln Leu
            180                 185                 190 gcc gat gcg ccg tac atg aaa atg gat ctc ctg gaa tgg agt cgc cat     624
Ala Asp Ala Pro Tyr Met Lys Met Asp Leu Leu Glu Trp Ser Arg His
        195                 200                 205 ttc cgc tgc ttc ccc ggg cag ggc gag ctg ccg ctg gag ccg ttt gcc     672
Phe Arg Cys Phe Pro Gly Gln Gly Glu Leu Pro Leu Glu Pro Phe Ala
    210                 215                 220 gag cag gtc acc cgc tgc ggc tat cgc ggc ccc tgg tcg ctg gag atc     720
Glu Gln Val Thr Arg Cys Gly Tyr Arg Gly Pro Trp Ser Leu Glu Ile
225                 230                 235                 240 ttt aat gac ggt ttt cgc gcc tcg ccg aac ggc gcg acg gcc aaa gat     768
Phe Asn Asp Gly Phe Arg Ala Ser Pro Asn Gly Ala Thr Ala Lys Asp
                245                 250                 255 ggt tat cgt tcg ctg ctg tgg ctg gag gag caa acc cgc cgt cgg ctc     816
Gly Tyr Arg Ser Leu Leu Trp Leu Glu Glu Gln Thr Arg Arg Arg Leu
            260                 265                 270 ccg acg tgc gat gcc gat ctg ttt tca ccg ccg ccg ctg ccg gtc tat     864
Pro Thr Cys Asp Ala Asp Leu Phe Ser Pro Pro Pro Leu Pro Val Tyr
        275                 280                 285 cac ggg ctg gag ttt atc gag ttt gcc gcc agc gcc gcc gag gcg cag     912
His Gly Leu Glu Phe Ile Glu Phe Ala Ala Ser Ala Ala Glu Ala Gln
    290                 295                 300 cgc ctg ggg cag cat ctg cag gcg ctg ggt ttt cag cac gag gga agc     960
Arg Leu Gly Gln His Leu Gln Ala Leu Gly Phe Gln His Glu Gly Ser
305                 310                 315                 320 cac cgc tcc aaa cag gtg acg ctg tgg cgc aac ggg gcg cgg atc        1008
His Arg Ser Lys Gln Val Thr Leu Trp Arg Asn Gly Ala Arg Ile
                325                 330                 335 gtc atc aac cat cag ccc cac agc tgg gcc gat cat ttc tat caa cgc    1056
Val Ile Asn His Gln Pro His Ser Trp Ala Asp His Phe Tyr Gln Arg
            340                 345                 350 cac ggc gta tcg ctg tgc gcc atg gcg ctg cgg gtc gat cgc agt gcg    1104
His Gly Val Ser Leu Cys Ala Met Ala Leu Arg Val Asp Arg Ser Ala
        355                 360                 365 ccg att gtg gcc cgc gcc cgg gcg ctg ggg tat gcc acc tgg cag ggc    1152
Pro Ile Val Ala Arg Ala Arg Ala Leu Gly Tyr Ala Thr Trp Gln Gly
    370                 375                 380 gat gcc ggg cca aac gaa acg ccg atc ccg gcg atc tgc gcc ccg gac    1200
Asp Ala Gly Pro Asn Glu Thr Pro Ile Pro Ala Ile Cys Ala Pro Asp
385                 390                 395                 400 ggt agc ctt atc tat ctc atc gag gcc ggg gaa ggg atc tat gag cgc    1248
Gly Ser Leu Ile Tyr Leu Ile Glu Ala Gly Glu Gly Ile Tyr Glu Arg
                405                 410                 415
```

| | | | | | | | | | | | | | | | | |
|---|---|---|---|---|---|---|---|---|---|---|---|---|---|---|---|---|
| gat | ttt | cat | ctg | cgc | gac | gga | ctg | acg | gtg | cgc | gag | gat | tat | ctc | ggt | 1296 |
| Asp | Phe | His | Leu | Arg | Asp | Gly | Leu | Thr | Val | Arg | Glu | Asp | Tyr | Leu | Gly | |
| | | | 420 | | | | | 425 | | | | | 430 | | | |
| atc | gac | cat | ctg | gcg | ctg | ggg | atg | gag | gcc | gac | agc | cgc | gac | aac | tgg | 1344 |
| Ile | Asp | His | Leu | Ala | Leu | Gly | Met | Glu | Ala | Asp | Ser | Arg | Asp | Asn | Trp | |
| | | | 435 | | | | | 440 | | | | | 445 | | | |
| gtg | atg | ttc | ttc | cgc | acg | gtg | ttt | ggt | ttt | acc | ctt | gag | cat | gag | cag | 1392 |
| Val | Met | Phe | Phe | Arg | Thr | Val | Phe | Gly | Phe | Thr | Leu | Glu | His | Glu | Gln | |
| | | | | 450 | | | | | 455 | | | | | 460 | | |
| acg | ctg | ccg | gac | ccg | tat | gga | ctg | gtg | cgc | agt | ctg | gcg | gtg | cgc | agc | 1440 |
| Thr | Leu | Pro | Asp | Pro | Tyr | Gly | Leu | Val | Arg | Ser | Leu | Ala | Val | Arg | Ser | |
| 465 | | | | | 470 | | | | | 475 | | | | | 480 | |
| ccg | cag | ggc | gat | atc | cgt | ctg | gcg | ctg | aat | att | tcg | cag | agc | cgg | gcg | 1488 |
| Pro | Gln | Gly | Asp | Ile | Arg | Leu | Ala | Leu | Asn | Ile | Ser | Gln | Ser | Arg | Ala | |
| | | | | 485 | | | | | 490 | | | | | 495 | | |
| acg | cag | att | gcc | cgc | tcg | gtc | gcc | tgc | tac | cag | ggg | gca | ggg | ctg | cag | 1536 |
| Thr | Gln | Ile | Ala | Arg | Ser | Val | Ala | Cys | Tyr | Gln | Gly | Ala | Gly | Leu | Gln | |
| | | | | 500 | | | | | 505 | | | | | 510 | | |
| cat | gcg | gcc | ttt | gcc | tgc | cgc | gat | ctg | ccg | gcc | acc | tgc | gac | cag | ctt | 1584 |
| His | Ala | Ala | Phe | Ala | Cys | Arg | Asp | Leu | Pro | Ala | Thr | Cys | Asp | Gln | Leu | |
| | | | 515 | | | | | 520 | | | | | 525 | | | |
| gcc | gac | gtt | gcc | cgc | cat | gcg | ctg | ccg | atc | ccg | gcc | aat | tat | tat | gac | 1632 |
| Ala | Asp | Val | Ala | Arg | His | Ala | Leu | Pro | Ile | Pro | Ala | Asn | Tyr | Tyr | Asp | |
| | | | 530 | | | | | 535 | | | | | 540 | | | |
| gat | ctg | ctg | gcg | cgc | ttc | ggc | ggc | gag | ctg | gac | gtt | ggg | caa | ctg | cag | 1680 |
| Asp | Leu | Leu | Ala | Arg | Phe | Gly | Gly | Glu | Leu | Asp | Val | Gly | Gln | Leu | Gln | |
| 545 | | | | | 550 | | | | | 555 | | | | | 560 | |
| cgg | cgg | cag | ctc | ctc | tac | gac | cgc | gat | ccg | cag | ggc | ggg | gcc | ttc | ctg | 1728 |
| Arg | Arg | Gln | Leu | Leu | Tyr | Asp | Arg | Asp | Pro | Gln | Gly | Gly | Ala | Phe | Leu | |
| | | | | 565 | | | | | 570 | | | | | 575 | | |
| cat | ctt | tat | acc | cgc | ccc | ttt | acc | gcc | ggg | cgc | ttt | ttc | ttt | gag | tta | 1776 |
| His | Leu | Tyr | Thr | Arg | Pro | Phe | Thr | Ala | Gly | Arg | Phe | Phe | Phe | Glu | Leu | |
| | | | 580 | | | | | 585 | | | | | 590 | | | |
| acc | gaa | cga | cgg | gcc | ggt | tac | gcg | ctc | tat | ggc | gcg | gcg | aat | gcc | gcc | 1824 |
| Thr | Glu | Arg | Arg | Ala | Gly | Tyr | Ala | Leu | Tyr | Gly | Ala | Ala | Asn | Ala | Ala | |
| | | | 595 | | | | | 600 | | | | | 605 | | | |
| gtc | cgt | ctg | gcg | gcg | atg | cag | tat | tgt | | | | | | | | 1851 |
| Val | Arg | Leu | Ala | Ala | Met | Gln | Tyr | Cys | | | | | | | | |
| | | 610 | | | | | 615 | | | | | | | | | |

```
<210> SEQ ID NO 4
<211> LENGTH: 617
<212> TYPE: PRT
<213> ORGANISM: Klebsiella variicola

<400> SEQUENCE: 4
```

Met Leu Arg Ser Ile Ala Thr Val Ser Ile Ser Gly Thr Leu Pro Glu
1               5                   10                  15

Lys Leu His Ala Ile Ala Ala Ala Gly Tyr Gln Gly Val Glu Ile Phe
                20                  25                  30

Glu Asn Asp Leu Leu Tyr Tyr Thr Gly Thr Pro Ala Glu Ile Arg Gln
        35                  40                  45

Leu Ala Ala Asp Leu Gly Leu Lys Ile Thr Leu Phe Gln Pro Phe Arg
    50                  55                  60

Asp Phe Glu Gly Ala Ser Arg Ala Gln Phe Ala Ala Asn Ile Ala Arg
65                  70                  75                  80

Ala Arg Arg Lys Phe Ala Leu Met His Glu Leu Gly Cys Asp Thr Leu
                85                  90                  95

Leu Leu Cys Ser Asn Val Gln Pro Asp Cys Ser Ala Asp Ser Glu Leu

```
            100                 105                 110
Gln Val Ala Asp Leu Arg Ala Leu Ala Thr Leu Ala Glu Glu Gly
            115                 120                 125

Ile Thr Ile Gly Tyr Glu Ala Leu Ala Trp Gly Thr His Val Asn Arg
            130                 135                 140

Trp Gln Gln Ala Trp Glu Arg Val Arg Val Asp Ser Pro Ala Leu
145             150                 155                 160

Gly Leu Val Leu Asp Ser Phe His Ile Leu Ala Arg Gly Asp Thr Leu
            165                 170                 175

Asp Ala Leu Pro Ser Val Pro Val Glu Lys Ile Thr Phe Val Gln Leu
            180                 185                 190

Ala Asp Ala Pro Tyr Met Lys Met Asp Leu Leu Glu Trp Ser Arg His
            195                 200                 205

Phe Arg Cys Phe Pro Gly Gln Gly Glu Leu Pro Leu Glu Pro Phe Ala
            210                 215                 220

Glu Gln Val Thr Arg Cys Gly Tyr Arg Gly Pro Trp Ser Leu Glu Ile
225                 230                 235                 240

Phe Asn Asp Gly Phe Arg Ala Ser Pro Asn Gly Ala Thr Ala Lys Asp
                245                 250                 255

Gly Tyr Arg Ser Leu Leu Trp Leu Glu Glu Gln Thr Arg Arg Leu
                260                 265                 270

Pro Thr Cys Asp Ala Asp Leu Phe Ser Pro Pro Leu Pro Val Tyr
                275                 280                 285

His Gly Leu Glu Phe Ile Glu Phe Ala Ala Ser Ala Ala Glu Ala Gln
            290                 295                 300

Arg Leu Gly Gln His Leu Gln Ala Leu Gly Phe Gln His Glu Gly Ser
305                 310                 315                 320

His Arg Ser Lys Gln Val Thr Leu Trp Arg Asn Gly Gly Ala Arg Ile
                325                 330                 335

Val Ile Asn His Gln Pro His Ser Trp Ala Asp His Phe Tyr Gln Arg
                340                 345                 350

His Gly Val Ser Leu Cys Ala Met Ala Leu Arg Val Asp Arg Ser Ala
                355                 360                 365

Pro Ile Val Ala Arg Ala Arg Ala Leu Gly Tyr Ala Thr Trp Gln Gly
            370                 375                 380

Asp Ala Gly Pro Asn Glu Thr Pro Ile Pro Ala Ile Cys Ala Pro Asp
385                 390                 395                 400

Gly Ser Leu Ile Tyr Leu Ile Glu Ala Gly Glu Gly Ile Tyr Glu Arg
                405                 410                 415

Asp Phe His Leu Arg Asp Gly Leu Thr Val Arg Glu Asp Tyr Leu Gly
                420                 425                 430

Ile Asp His Leu Ala Leu Gly Met Glu Ala Asp Ser Arg Asp Asn Trp
            435                 440                 445

Val Met Phe Phe Arg Thr Val Phe Gly Phe Thr Leu Glu His Glu Gln
            450                 455                 460

Thr Leu Pro Asp Pro Tyr Gly Leu Val Arg Ser Leu Ala Val Arg Ser
465                 470                 475                 480

Pro Gln Gly Asp Ile Arg Leu Ala Leu Asn Ile Ser Gln Ser Arg Ala
                485                 490                 495

Thr Gln Ile Ala Arg Ser Val Ala Cys Tyr Gln Gly Ala Gly Leu Gln
                500                 505                 510

His Ala Ala Phe Ala Cys Arg Asp Leu Pro Ala Thr Cys Asp Gln Leu
            515                 520                 525
```

-continued

```
Ala Asp Val Ala Arg His Ala Leu Pro Ile Pro Ala Asn Tyr Tyr Asp
    530                 535                 540
Asp Leu Leu Ala Arg Phe Gly Gly Glu Leu Asp Val Gly Gln Leu Gln
545                 550                 555                 560
Arg Arg Gln Leu Leu Tyr Asp Arg Asp Pro Gln Gly Gly Ala Phe Leu
                565                 570                 575
His Leu Tyr Thr Arg Pro Phe Thr Ala Gly Arg Phe Phe Glu Leu
                580                 585                 590
Thr Glu Arg Arg Ala Gly Tyr Ala Leu Tyr Gly Ala Ala Asn Ala Ala
                595                 600                 605
Val Arg Leu Ala Ala Met Gln Tyr Cys
    610                 615

<210> SEQ ID NO 5
<211> LENGTH: 840
<212> TYPE: DNA
<213> ORGANISM: Bacillus thuringiensis
<220> FEATURE:
<221> NAME/KEY: CDS
<222> LOCATION: (1)..(840)

<400> SEQUENCE: 5 atg aaa tat tca cta tgt acc att tca ttt cgc cat caa tta att tca      48
Met Lys Tyr Ser Leu Cys Thr Ile Ser Phe Arg His Gln Leu Ile Ser
1               5                   10                  15 ttt act gat att gtt caa ttt gca tat gaa aac ggt ttt gaa ggc att      96
Phe Thr Asp Ile Val Gln Phe Ala Tyr Glu Asn Gly Phe Glu Gly Ile
                20                  25                  30 gaa tta tgg ggg act cat gcg caa aat ttg tat atg cag gag tat gaa     144
Glu Leu Trp Gly Thr His Ala Gln Asn Leu Tyr Met Gln Glu Tyr Glu
            35                  40                  45 acg aca gaa cga gaa ttg aat tgt tta aag gat aaa acc ttg gaa att     192
Thr Thr Glu Arg Glu Leu Asn Cys Leu Lys Asp Lys Thr Leu Glu Ile
        50                  55                  60 acg atg ata agt gat tac tta gac ata tca tta tcg gca gat ttt gaa     240
Thr Met Ile Ser Asp Tyr Leu Asp Ile Ser Leu Ser Ala Asp Phe Glu
65                  70                  75                  80 aaa acg ata gag aaa tgt gaa caa ctt gca ata cta gct aat tgg ttt     288
Lys Thr Ile Glu Lys Cys Glu Gln Leu Ala Ile Leu Ala Asn Trp Phe
                85                  90                  95 aaa acg aac aaa att cgt acg ttt gct gga caa aaa ggt agt gca gat     336
Lys Thr Asn Lys Ile Arg Thr Phe Ala Gly Gln Lys Gly Ser Ala Asp
                100                 105                 110 ttt tcg caa caa gag aga caa gag tat gtg aat cgt att cgc atg att     384
Phe Ser Gln Gln Glu Arg Gln Glu Tyr Val Asn Arg Ile Arg Met Ile
            115                 120                 125 tgt gaa tta ttt gct cag cat aat atg tat gta ctt tta gaa aca cac     432
Cys Glu Leu Phe Ala Gln His Asn Met Tyr Val Leu Leu Glu Thr His
        130                 135                 140 cca aat acg tta acg gat acg ttg cct tct act ttg gaa tta tta ggc     480
Pro Asn Thr Leu Thr Asp Thr Leu Pro Ser Thr Leu Glu Leu Leu Gly
145                 150                 155                 160 gaa gta gat cat ccg aat ttg aaa ata aat ctt gat ttt ctt cat ata     528
Glu Val Asp His Pro Asn Leu Lys Ile Asn Leu Asp Phe Leu His Ile
                165                 170                 175 tgg gag tct ggt gca gat cca gtt gac agc ttc cag caa cta aga ccg     576
Trp Glu Ser Gly Ala Asp Pro Val Asp Ser Phe Gln Gln Leu Arg Pro
            180                 185                 190 tgg ata caa cat tac cat ttt aag aat ata tct tca gca gat tat tta     624
```

```
Trp Ile Gln His Tyr His Phe Lys Asn Ile Ser Ser Ala Asp Tyr Leu
            195                 200                 205 cat gtg ttc gaa ccg aat aat gta tat gca gca gcg gga aat cgt act        672
His Val Phe Glu Pro Asn Asn Val Tyr Ala Ala Ala Gly Asn Arg Thr
        210                 215                 220 ggt atg gtt cca tta ttt gaa ggc att gta aat tat gat gag att att        720
Gly Met Val Pro Leu Phe Glu Gly Ile Val Asn Tyr Asp Glu Ile Ile
225                 230                 235                 240 cag gaa gtg aga gat act gat cat ttc gct tca ctc gaa tgg ttt gga        768
Gln Glu Val Arg Asp Thr Asp His Phe Ala Ser Leu Glu Trp Phe Gly
                245                 250                 255 cat aat gcg aaa gat ata tta aaa gca gaa atg aaa gta cta aca aat        816
His Asn Ala Lys Asp Ile Leu Lys Ala Glu Met Lys Val Leu Thr Asn
            260                 265                 270 aga aat tta gaa gta gta act tct                                        840
Arg Asn Leu Glu Val Val Thr Ser
        275                 280

<210> SEQ ID NO 6
<211> LENGTH: 280
<212> TYPE: PRT
<213> ORGANISM: Bacillus thuringiensis

<400> SEQUENCE: 6

Met Lys Tyr Ser Leu Cys Thr Ile Ser Phe Arg His Gln Leu Ile Ser
1               5                   10                  15

Phe Thr Asp Ile Val Gln Phe Ala Tyr Glu Asn Gly Phe Glu Gly Ile
            20                  25                  30

Glu Leu Trp Gly Thr His Ala Gln Asn Leu Tyr Met Gln Glu Tyr Glu
        35                  40                  45

Thr Thr Glu Arg Glu Leu Asn Cys Leu Lys Asp Lys Thr Leu Glu Ile
    50                  55                  60

Thr Met Ile Ser Asp Tyr Leu Asp Ile Ser Leu Ser Ala Asp Phe Glu
65                  70                  75                  80

Lys Thr Ile Glu Lys Cys Glu Gln Leu Ala Ile Leu Ala Asn Trp Phe
                85                  90                  95

Lys Thr Asn Lys Ile Arg Thr Phe Ala Gly Gln Lys Gly Ser Ala Asp
            100                 105                 110

Phe Ser Gln Gln Glu Arg Gln Glu Tyr Val Asn Arg Ile Arg Met Ile
        115                 120                 125

Cys Glu Leu Phe Ala Gln His Asn Met Tyr Val Leu Leu Glu Thr His
    130                 135                 140

Pro Asn Thr Leu Thr Asp Thr Leu Pro Ser Thr Leu Glu Leu Leu Gly
145                 150                 155                 160

Glu Val Asp His Pro Asn Leu Lys Ile Asn Leu Asp Phe Leu His Ile
                165                 170                 175

Trp Glu Ser Gly Ala Asp Pro Val Asp Ser Phe Gln Gln Leu Arg Pro
            180                 185                 190

Trp Ile Gln His Tyr His Phe Lys Asn Ile Ser Ser Ala Asp Tyr Leu
        195                 200                 205

His Val Phe Glu Pro Asn Asn Val Tyr Ala Ala Ala Gly Asn Arg Thr
    210                 215                 220

Gly Met Val Pro Leu Phe Glu Gly Ile Val Asn Tyr Asp Glu Ile Ile
225                 230                 235                 240

Gln Glu Val Arg Asp Thr Asp His Phe Ala Ser Leu Glu Trp Phe Gly
                245                 250                 255
```

```
His Asn Ala Lys Asp Ile Leu Lys Ala Glu Met Lys Val Leu Thr Asn
            260                 265                 270

Arg Asn Leu Glu Val Val Thr Ser
        275                 280

<210> SEQ ID NO 7
<211> LENGTH: 1848
<212> TYPE: DNA
<213> ORGANISM: Enterobacter aerogenes
<220> FEATURE:
<221> NAME/KEY: CDS
<222> LOCATION: (1)..(1848)

<400> SEQUENCE: 7 atg ttg cgt tcc atc gct acc gtc tcg ata tcc ggt act tta ccc gaa      48
Met Leu Arg Ser Ile Ala Thr Val Ser Ile Ser Gly Thr Leu Pro Glu
1               5                  10                  15 aag ctg cac gct atc gcc gcg gcc ggt tat cag ggc gtt gaa atc ttt      96
Lys Leu His Ala Ile Ala Ala Ala Gly Tyr Gln Gly Val Glu Ile Phe
            20                  25                  30 gaa aac gat ctg ctc tat tat acg ggc acg ccg cgc gat att cgc aac     144
Glu Asn Asp Leu Leu Tyr Tyr Thr Gly Thr Pro Arg Asp Ile Arg Asn
        35                  40                  45 ctt gcc gct gaa tta ggg cta aaa atc acc ctt ttt caa ccc ttt cgc     192
Leu Ala Ala Glu Leu Gly Leu Lys Ile Thr Leu Phe Gln Pro Phe Arg
    50                  55                  60 gat ttt gag ggc gcc agc cgc gcg cag ttt gcc gct aac cta cag cgg     240
Asp Phe Glu Gly Ala Ser Arg Ala Gln Phe Ala Ala Asn Leu Gln Arg
65                  70                  75                  80 gcg aag cgg aaa ttc gcc ctg atg cat gaa ctg ggt tgc gac acc atg     288
Ala Lys Arg Lys Phe Ala Leu Met His Glu Leu Gly Cys Asp Thr Met
                85                  90                  95 ctg ctc tgt agc aac gtc cag ccg gac tgt tcg gcc gat atc gaa ctg     336
Leu Leu Cys Ser Asn Val Gln Pro Asp Cys Ser Ala Asp Ile Glu Leu
            100                 105                 110 cag gtc gcc gac ctg cgc gcg ctg gcc gat ctc gcc gag cag gag ggg     384
Gln Val Ala Asp Leu Arg Ala Leu Ala Asp Leu Ala Glu Gln Glu Gly
        115                 120                 125 gtt gtc att ggc tac gaa gcg ctg gcg tgg ggt act cac gtt aac cac     432
Val Val Ile Gly Tyr Glu Ala Leu Ala Trp Gly Thr His Val Asn His
    130                 135                 140 tgg cgt cag gca tgg gaa cgg gtg cag cgg gtt aac agc ccg gcg atg     480
Trp Arg Gln Ala Trp Glu Arg Val Gln Arg Val Asn Ser Pro Ala Met
145                 150                 155                 160 ggc atc gtt ctt gat agt ttc cat att ctg tcg ctc ggt gat gat cta     528
Gly Ile Val Leu Asp Ser Phe His Ile Leu Ser Leu Gly Asp Asp Leu
                165                 170                 175 caa ggc ctt gcc gag gtg ccg gtt gag aaa atc acc ttc ctg cag ctg     576
Gln Gly Leu Ala Glu Val Pro Val Glu Lys Ile Thr Phe Leu Gln Leu
            180                 185                 190 gcc gac gcg ccg ttg atg aag atg gat gtc ctc gaa tgg agc cgt cat     624
Ala Asp Ala Pro Leu Met Lys Met Asp Val Leu Glu Trp Ser Arg His
        195                 200                 205 ttc cgc tgc ttc ccg ggc cag ggg caa ctg ccg ctg gtg gat ttc gcc     672
Phe Arg Cys Phe Pro Gly Gln Gly Gln Leu Pro Leu Val Asp Phe Ala
    210                 215                 220 tgt gaa ctg acg cgc tgc ggc tat cgc ggc ccc tgg tcg ctg gag att     720
Cys Glu Leu Thr Arg Cys Gly Tyr Arg Gly Pro Trp Ser Leu Glu Ile
225                 230                 235                 240 ttc aat gac ggc ttt cgc gcc tca ccc aac ggc gcc acg gca aaa gat     768
Phe Asn Asp Gly Phe Arg Ala Ser Pro Asn Gly Ala Thr Ala Lys Asp
```

|  |  |
|---|---:|
|                    245                        250                       255 | |
| ggc tac cgt tca ttg ctg tgg ctc gaa gag cag acc cgt cgg cag ctt<br>Gly Tyr Arg Ser Leu Leu Trp Leu Glu Glu Gln Thr Arg Arg Gln Leu<br>            260                        265                        270 | 816 |
| gcg gat agc gac gcg gcg tta ttt tcg cca cct gcg cta ccg cac tat<br>Ala Asp Ser Asp Ala Ala Leu Phe Ser Pro Pro Ala Leu Pro His Tyr<br>        275                        280                        285 | 864 |
| gac ggc ctg gag ttt att gag ttc gcc gcc agt ccg gcg gag tct acc<br>Asp Gly Leu Glu Phe Ile Glu Phe Ala Ala Ser Pro Ala Glu Ser Thr<br>290                        295                        300 | 912 |
| gcg cta ggc cag cgc ctg acg cag ttg ggc ttt aag ctt cag ggc aag<br>Ala Leu Gly Gln Arg Leu Thr Gln Leu Gly Phe Lys Leu Gln Gly Lys<br>305                      310                      315                      320 | 960 |
| cat cgt tcc aag cag gtt gca ctc tgg cgt aat ggc gag gcg cgg gtg<br>His Arg Ser Lys Gln Val Ala Leu Trp Arg Asn Gly Glu Ala Arg Val<br>                  325                        330                        335 | 1008 |
| att gtt aac gcg cag ccg cac agc tgg gcc gac cat ttt cat cag cgc<br>Ile Val Asn Ala Gln Pro His Ser Trp Ala Asp His Phe His Gln Arg<br>            340                        345                        350 | 1056 |
| cac ggc atc tcg ttg tgc gca atg gcg ctg cgg gtg agc cac agc gca<br>His Gly Ile Ser Leu Cys Ala Met Ala Leu Arg Val Ser His Ser Ala<br>        355                        360                        365 | 1104 |
| ccg gtt gtg gag cgc gcc cgc gcc tac ggt tat gcc acc tgg cag ggg<br>Pro Val Val Glu Arg Ala Arg Ala Tyr Gly Tyr Ala Thr Trp Gln Gly<br>370                        375                        380 | 1152 |
| gat gcc ggt cct aat gag agt tcg atc ccg gcg gtt tgc gcc ccg gat<br>Asp Ala Gly Pro Asn Glu Ser Ser Ile Pro Ala Val Cys Ala Pro Asp<br>385                      390                      395                      400 | 1200 |
| ggc agc ctg atc tac ctg gtt gaa acc ggt gac gac atc tac gcc cgc<br>Gly Ser Leu Ile Tyr Leu Val Glu Thr Gly Asp Asp Ile Tyr Ala Arg<br>                  405                        410                        415 | 1248 |
| gat ttt cat ttg cag gca gac gcg ccg cgc gag gac tac tgc ggt att<br>Asp Phe His Leu Gln Ala Asp Ala Pro Arg Glu Asp Tyr Cys Gly Ile<br>            420                        425                        430 | 1296 |
| gac cat ctg gcg tta ggc atg gag gcc gat agc cgc gac aac tgg att<br>Asp His Leu Ala Leu Gly Met Glu Ala Asp Ser Arg Asp Asn Trp Ile<br>        435                        440                        445 | 1344 |
| atc ttt ttc cgt acg gtt ttc ggc ttc agt ctc gaa cac gaa cag acg<br>Ile Phe Phe Arg Thr Val Phe Gly Phe Ser Leu Glu His Glu Gln Thr<br>450                        455                        460 | 1392 |
| ttg ccc gac cca tac ggc ctg gtg cgc agc ctg gcg gtt cat agc ccg<br>Leu Pro Asp Pro Tyr Gly Leu Val Arg Ser Leu Ala Val His Ser Pro<br>465                        470                      475                      480 | 1440 |
| cag ggc gat atc cgt ctg gcg ctg aat att tcg caa agt cga gcc acg<br>Gln Gly Asp Ile Arg Leu Ala Leu Asn Ile Ser Gln Ser Arg Ala Thr<br>                  485                        490                        495 | 1488 |
| cag ata gcg cgt tcg gtc gcc tgt tat cag ggc gcc ggg cta cag cac<br>Gln Ile Ala Arg Ser Val Ala Cys Tyr Gln Gly Ala Gly Leu Gln His<br>            500                        505                        510 | 1536 |
| gcc gct ttt gcc tgt cgc gat tta ccc gca acg ctc gaa aat ctg ccg<br>Ala Ala Phe Ala Cys Arg Asp Leu Pro Ala Thr Leu Glu Asn Leu Pro<br>        515                        520                        525 | 1584 |
| cag gcc gcg ctg aac gcg cta ccg atc ccg gcg aat tac tat gag gat<br>Gln Ala Ala Leu Asn Ala Leu Pro Ile Pro Ala Asn Tyr Tyr Glu Asp<br>530                        535                      540 | 1632 |
| ctg ctg gcg cgc ttc ggt gga gag tcg cag gta gag acg ctg caa cgc<br>Leu Leu Ala Arg Phe Gly Gly Glu Ser Gln Val Glu Thr Leu Gln Arg<br>545                      550                      555                      560 | 1680 |
| ctg caa att ctc tac gac cgt gat acc cgc ggc ggc gaa ttc ctc cat | 1728 |

```
                Leu Gln Ile Leu Tyr Asp Arg Asp Thr Arg Gly Gly Glu Phe Leu His
                            565                 570                 575 ctt tat acc cgt cca ttc gcg gcg ggg cgt ttc ttc ttc gaa ttg acc            1776
Leu Tyr Thr Arg Pro Phe Ala Ala Gly Arg Phe Phe Phe Glu Leu Thr
            580                 585                 590 gaa cgg cgc gac ggt tac gcc cag tac ggc gcg gta aat gcc gcc gtc            1824
Glu Arg Arg Asp Gly Tyr Ala Gln Tyr Gly Ala Val Asn Ala Ala Val
            595                 600                 605 cgc ctt tcg gcg atg cag tac agt                                            1848
Arg Leu Ser Ala Met Gln Tyr Ser
            610             615

<210> SEQ ID NO 8
<211> LENGTH: 616
<212> TYPE: PRT
<213> ORGANISM: Enterobacter aerogenes

<400> SEQUENCE: 8

Met Leu Arg Ser Ile Ala Thr Val Ser Ile Ser Gly Thr Leu Pro Glu
 1               5                  10                  15

Lys Leu His Ala Ile Ala Ala Gly Tyr Gln Gly Val Glu Ile Phe
             20                  25                  30

Glu Asn Asp Leu Leu Tyr Tyr Thr Gly Thr Pro Arg Asp Ile Arg Asn
         35                  40                  45

Leu Ala Ala Glu Leu Gly Leu Lys Ile Thr Leu Phe Gln Pro Phe Arg
     50                  55                  60

Asp Phe Glu Gly Ala Ser Arg Ala Gln Phe Ala Ala Asn Leu Gln Arg
 65                  70                  75                  80

Ala Lys Arg Lys Phe Ala Leu Met His Glu Leu Gly Cys Asp Thr Met
                 85                  90                  95

Leu Leu Cys Ser Asn Val Gln Pro Asp Cys Ser Ala Asp Ile Glu Leu
            100                 105                 110

Gln Val Ala Asp Leu Arg Ala Leu Ala Asp Leu Ala Glu Gln Glu Gly
        115                 120                 125

Val Val Ile Gly Tyr Glu Ala Leu Ala Trp Gly Thr His Val Asn His
    130                 135                 140

Trp Arg Gln Ala Trp Glu Arg Val Gln Arg Val Asn Ser Pro Ala Met
145                 150                 155                 160

Gly Ile Val Leu Asp Ser Phe His Ile Leu Ser Leu Gly Asp Asp Leu
                165                 170                 175

Gln Gly Leu Ala Glu Val Pro Val Glu Lys Ile Thr Phe Leu Gln Leu
            180                 185                 190

Ala Asp Ala Pro Leu Met Lys Met Asp Val Leu Glu Trp Ser Arg His
        195                 200                 205

Phe Arg Cys Phe Pro Gly Gln Gly Gln Leu Pro Leu Val Asp Phe Ala
    210                 215                 220

Cys Glu Leu Thr Arg Cys Gly Tyr Arg Gly Pro Trp Ser Leu Glu Ile
225                 230                 235                 240

Phe Asn Asp Gly Phe Arg Ala Ser Pro Asn Gly Ala Thr Ala Lys Asp
                245                 250                 255

Gly Tyr Arg Ser Leu Leu Trp Leu Glu Glu Gln Thr Arg Arg Gln Leu
            260                 265                 270

Ala Asp Ser Asp Ala Ala Leu Phe Ser Pro Pro Ala Leu Pro His Tyr
        275                 280                 285

Asp Gly Leu Glu Phe Ile Glu Phe Ala Ala Ser Pro Ala Glu Ser Thr
        290                 295                 300
```

```
Ala Leu Gly Gln Arg Leu Thr Gln Leu Gly Phe Lys Leu Gln Gly Lys
305                 310                 315                 320

His Arg Ser Lys Gln Val Ala Leu Trp Arg Asn Gly Glu Ala Arg Val
            325                 330                 335

Ile Val Asn Ala Gln Pro His Ser Trp Ala Asp His Phe His Gln Arg
        340                 345                 350

His Gly Ile Ser Leu Cys Ala Met Ala Leu Arg Val Ser His Ser Ala
    355                 360                 365

Pro Val Val Glu Arg Ala Arg Ala Tyr Gly Tyr Ala Thr Trp Gln Gly
370                 375                 380

Asp Ala Gly Pro Asn Glu Ser Ser Ile Pro Ala Val Cys Ala Pro Asp
385                 390                 395                 400

Gly Ser Leu Ile Tyr Leu Val Glu Thr Gly Asp Asp Ile Tyr Ala Arg
            405                 410                 415

Asp Phe His Leu Gln Ala Asp Ala Pro Arg Glu Asp Tyr Cys Gly Ile
        420                 425                 430

Asp His Leu Ala Leu Gly Met Glu Ala Asp Ser Arg Asp Asn Trp Ile
    435                 440                 445

Ile Phe Phe Arg Thr Val Phe Gly Phe Ser Leu Glu His Glu Gln Thr
450                 455                 460

Leu Pro Asp Pro Tyr Gly Leu Val Arg Ser Leu Ala Val His Ser Pro
465                 470                 475                 480

Gln Gly Asp Ile Arg Leu Ala Leu Asn Ile Ser Gln Ser Arg Ala Thr
            485                 490                 495

Gln Ile Ala Arg Ser Val Ala Cys Tyr Gln Gly Ala Gly Leu Gln His
        500                 505                 510

Ala Ala Phe Ala Cys Arg Asp Leu Pro Ala Thr Leu Glu Asn Leu Pro
    515                 520                 525

Gln Ala Ala Leu Asn Ala Leu Pro Ile Pro Ala Asn Tyr Tyr Glu Asp
530                 535                 540

Leu Leu Ala Arg Phe Gly Gly Glu Ser Gln Val Glu Thr Leu Gln Arg
545                 550                 555                 560

Leu Gln Ile Leu Tyr Asp Arg Asp Thr Arg Gly Gly Glu Phe Leu His
            565                 570                 575

Leu Tyr Thr Arg Pro Phe Ala Ala Gly Arg Phe Phe Phe Glu Leu Thr
        580                 585                 590

Glu Arg Arg Asp Gly Tyr Ala Gln Tyr Gly Ala Val Asn Ala Ala Val
    595                 600                 605

Arg Leu Ser Ala Met Gln Tyr Ser
    610                 615

<210> SEQ ID NO 9
<211> LENGTH: 1458
<212> TYPE: DNA
<213> ORGANISM: Acinetobacter baylyi
<220> FEATURE:
<221> NAME/KEY: CDS
<222> LOCATION: (1)..(1458)

<400> SEQUENCE: 9 atg aaa tta act tct tta cgc gta tct tta ttg gcg ctg ggc ttg gta      48
Met Lys Leu Thr Ser Leu Arg Val Ser Leu Leu Ala Leu Gly Leu Val
1               5                   10                  15 aca tca ggt ttt gct gcg gca gaa act tat act gta gat cgt tat cag     96
Thr Ser Gly Phe Ala Ala Ala Glu Thr Tyr Thr Val Asp Arg Tyr Gln
            20                  25                  30
```

-continued

| | | |
|---|---|---|
| gat gat agt gaa aaa ggc tct ttg cgt tgg gca att gaa caa tct aat<br>Asp Asp Ser Glu Lys Gly Ser Leu Arg Trp Ala Ile Glu Gln Ser Asn<br>            35                    40                      45 | | 144 |
| gca aat agc gca caa gag aat cag att ctg att cag gct gtt ggt aag<br>Ala Asn Ser Ala Gln Glu Asn Gln Ile Leu Ile Gln Ala Val Gly Lys<br>50                    55                    60 | | 192 |
| gca cct tat gtg atc aag gtg gat aaa ccg tta cca ccg att aaa tca<br>Ala Pro Tyr Val Ile Lys Val Asp Lys Pro Leu Pro Pro Ile Lys Ser<br>65                    70                    75                    80 | | 240 |
| tct gta aaa att att ggt aca gaa tgg gat aaa acg ggc gaa ttt att<br>Ser Val Lys Ile Ile Gly Thr Glu Trp Asp Lys Thr Gly Glu Phe Ile<br>                    85                    90                    95 | | 288 |
| gcg att gat ggt tca aac tat atc aag ggc gaa ggc gaa aaa gca tgt<br>Ala Ile Asp Gly Ser Asn Tyr Ile Lys Gly Glu Gly Glu Lys Ala Cys<br>                  100                  105                110 | | 336 |
| cca ggt gca aat cca gga caa tat ggt acc aat gtt cgt acc atg act<br>Pro Gly Ala Asn Pro Gly Gln Tyr Gly Thr Asn Val Arg Thr Met Thr<br>                  115                  120                125 | | 384 |
| tta cca ggt ttg gtt cta caa gat gtc aat ggt gtg acc ctg aaa ggt<br>Leu Pro Gly Leu Val Leu Gln Asp Val Asn Gly Val Thr Leu Lys Gly<br>130                    135                  140 | | 432 |
| ctt gat gtt cat cgc ttc tgt att ggt gta ctg gta aat cgt tca agc<br>Leu Asp Val His Arg Phe Cys Ile Gly Val Leu Val Asn Arg Ser Ser<br>145                    150                  155                160 | | 480 |
| aat aat ttg att cag cat aac cgt att tca aat aat tac ggt ggc gct<br>Asn Asn Leu Ile Gln His Asn Arg Ile Ser Asn Asn Tyr Gly Gly Ala<br>                  165                  170                175 | | 528 |
| ggt gtc atg atc acg ggt gat gat ggt aaa ggt aac cca acg tct acc<br>Gly Val Met Ile Thr Gly Asp Asp Gly Lys Gly Asn Pro Thr Ser Thr<br>                  180                  185                190 | | 576 |
| acc acc aat aac aac aaa gta ttg gat aat gtg ttt att gac aat ggc<br>Thr Thr Asn Asn Asn Lys Val Leu Asp Asn Val Phe Ile Asp Asn Gly<br>                  195                  200                205 | | 624 |
| gat ggt ctt gaa ctg acg cgt gga gca gca ttc aac ctg att gct aac<br>Asp Gly Leu Glu Leu Thr Arg Gly Ala Ala Phe Asn Leu Ile Ala Asn<br>210                    215                  220 | | 672 |
| aat ctg ttt aca tcg acc aaa gcc aat cca gag ccg tct caa ggc att<br>Asn Leu Phe Thr Ser Thr Lys Ala Asn Pro Glu Pro Ser Gln Gly Ile<br>225                    230                  235                240 | | 720 |
| gaa att ctt tgg ggg aat gac aat gca gtg gtg ggt aac aaa ttt gaa<br>Glu Ile Leu Trp Gly Asn Asp Asn Ala Val Val Gly Asn Lys Phe Glu<br>                  245                  250                255 | | 768 |
| aac tat tca gat ggt cta caa atc aac tgg ggt aaa cgt aat tac atc<br>Asn Tyr Ser Asp Gly Leu Gln Ile Asn Trp Gly Lys Arg Asn Tyr Ile<br>                  260                  265                270 | | 816 |
| gct tat aac gaa ttg acc aat aac tct ttg ggt ttc aat ctt aca ggt<br>Ala Tyr Asn Glu Leu Thr Asn Asn Ser Leu Gly Phe Asn Leu Thr Gly<br>                  275                  280                285 | | 864 |
| gat gga aac atc ttc gat agt aac aaa gtg cat ggc aat cgt att ggt<br>Asp Gly Asn Ile Phe Asp Ser Asn Lys Val His Gly Asn Arg Ile Gly<br>290                    295                  300 | | 912 |
| atc gca att cgt tct gaa aaa gat gca aat gca cgt atc aca ctt acc<br>Ile Ala Ile Arg Ser Glu Lys Asp Ala Asn Ala Arg Ile Thr Leu Thr<br>305                    310                  315                320 | | 960 |
| aaa aat cag att tgg gat aat ggt aaa gat atc aaa cgc tgt gag gct<br>Lys Asn Gln Ile Trp Asp Asn Gly Lys Asp Ile Lys Arg Cys Glu Ala<br>                  325                  330                335 | | 1008 |
| ggt ggt tca tgt gtt cca aac caa cgt tta ggc gca att gta ttt ggt<br>Gly Gly Ser Cys Val Pro Asn Gln Arg Leu Gly Ala Ile Val Phe Gly | | 1056 |

```
                    340                 345                 350
gtt cct gcg ctt gag cat gaa ggt ttt gta ggc tct cgt ggt ggc ggt        1104
Val Pro Ala Leu Glu His Glu Gly Phe Val Gly Ser Arg Gly Gly Gly
        355                 360                 365 gta gtc att gaa cct gca aaa tta caa aaa aca tgt aca cag cca aat        1152
Val Val Ile Glu Pro Ala Lys Leu Gln Lys Thr Cys Thr Gln Pro Asn
370                 375                 380 caa caa aac tgt aat gcc att ccg aac caa ggt att cag gca cct aaa        1200
Gln Gln Asn Cys Asn Ala Ile Pro Asn Gln Gly Ile Gln Ala Pro Lys
385                 390                 395                 400 ctg act gtc agt aaa aaa caa ctt aca gtt gaa gtt aaa gga aca cca        1248
Leu Thr Val Ser Lys Lys Gln Leu Thr Val Glu Val Lys Gly Thr Pro
            405                 410                 415 aac cag cgt tac aac gta gaa ttt ttt gga aat cgt aat gca tct tct        1296
Asn Gln Arg Tyr Asn Val Glu Phe Phe Gly Asn Arg Asn Ala Ser Ser
                420                 425                 430 tcc gaa gct gag caa tat tta ggt tca att gtt gta gtg aca gat cat        1344
Ser Glu Ala Glu Gln Tyr Leu Gly Ser Ile Val Val Val Thr Asp His
                    435                 440                 445 caa ggt ctt gca aaa gca aac tgg gca cca aaa gtc agc atg cca tct        1392
Gln Gly Leu Ala Lys Ala Asn Trp Ala Pro Lys Val Ser Met Pro Ser
450                 455                 460 gtt act gcg aat gta act gat cac ttg ggc gcc act tca gag tta agt        1440
Val Thr Ala Asn Val Thr Asp His Leu Gly Ala Thr Ser Glu Leu Ser
465                 470                 475                 480 tct gca gtg aaa atg aga                                                1458
Ser Ala Val Lys Met Arg
                485

<210> SEQ ID NO 10
<211> LENGTH: 486
<212> TYPE: PRT
<213> ORGANISM: Acinetobacter baylyi

<400> SEQUENCE: 10

Met Lys Leu Thr Ser Leu Arg Val Ser Leu Leu Ala Leu Gly Leu Val
1               5                   10                  15

Thr Ser Gly Phe Ala Ala Ala Glu Thr Tyr Thr Val Asp Arg Tyr Gln
                20                  25                  30

Asp Asp Ser Glu Lys Gly Ser Leu Arg Trp Ala Ile Glu Gln Ser Asn
            35                  40                  45

Ala Asn Ser Ala Gln Glu Asn Gln Ile Leu Ile Gln Ala Val Gly Lys
        50                  55                  60

Ala Pro Tyr Val Ile Lys Val Asp Lys Pro Leu Pro Ile Lys Ser
65                  70                  75                  80

Ser Val Lys Ile Ile Gly Thr Glu Trp Asp Lys Thr Gly Glu Phe Ile
                85                  90                  95

Ala Ile Asp Gly Ser Asn Tyr Ile Lys Gly Glu Gly Lys Ala Cys
            100                 105                 110

Pro Gly Ala Asn Pro Gly Gln Tyr Gly Thr Asn Val Arg Thr Met Thr
        115                 120                 125

Leu Pro Gly Leu Val Leu Gln Asp Val Asn Gly Val Thr Leu Lys Gly
    130                 135                 140

Leu Asp Val His Arg Phe Cys Ile Gly Val Leu Val Asn Arg Ser Ser
145                 150                 155                 160

Asn Asn Leu Ile Gln His Asn Arg Ile Ser Asn Asn Tyr Gly Gly Ala
                165                 170                 175
```

```
Gly Val Met Ile Thr Gly Asp Asp Gly Lys Gly Asn Pro Thr Ser Thr
                180                 185                 190

Thr Thr Asn Asn Lys Val Leu Asp Asn Val Phe Ile Asp Asn Gly
            195                 200                 205

Asp Gly Leu Glu Leu Thr Arg Gly Ala Ala Phe Asn Leu Ile Ala Asn
    210                 215                 220

Asn Leu Phe Thr Ser Thr Lys Ala Asn Pro Glu Pro Ser Gln Gly Ile
225                 230                 235                 240

Glu Ile Leu Trp Gly Asn Asp Asn Ala Val Gly Asn Lys Phe Glu
                245                 250                 255

Asn Tyr Ser Asp Gly Leu Gln Ile Asn Trp Gly Lys Arg Asn Tyr Ile
            260                 265                 270

Ala Tyr Asn Glu Leu Thr Asn Asn Ser Leu Gly Phe Asn Leu Thr Gly
        275                 280                 285

Asp Gly Asn Ile Phe Asp Ser Asn Lys Val His Gly Asn Arg Ile Gly
    290                 295                 300

Ile Ala Ile Arg Ser Glu Lys Asp Ala Asn Ala Arg Ile Thr Leu Thr
305                 310                 315                 320

Lys Asn Gln Ile Trp Asp Asn Gly Lys Asp Ile Lys Arg Cys Glu Ala
                325                 330                 335

Gly Gly Ser Cys Val Pro Asn Gln Arg Leu Gly Ala Ile Val Phe Gly
            340                 345                 350

Val Pro Ala Leu Glu His Glu Gly Phe Val Gly Ser Arg Gly Gly Gly
        355                 360                 365

Val Val Ile Glu Pro Ala Lys Leu Gln Lys Thr Cys Thr Gln Pro Asn
    370                 375                 380

Gln Gln Asn Cys Asn Ala Ile Pro Asn Gln Gly Ile Gln Ala Pro Lys
385                 390                 395                 400

Leu Thr Val Ser Lys Lys Gln Leu Thr Val Glu Val Lys Gly Thr Pro
                405                 410                 415

Asn Gln Arg Tyr Asn Val Glu Phe Phe Gly Asn Arg Asn Ala Ser Ser
            420                 425                 430

Ser Glu Ala Glu Gln Tyr Leu Gly Ser Ile Val Val Val Thr Asp His
        435                 440                 445

Gln Gly Leu Ala Lys Ala Asn Trp Ala Pro Lys Val Ser Met Pro Ser
    450                 455                 460

Val Thr Ala Asn Val Thr Asp His Leu Gly Ala Thr Ser Glu Leu Ser
465                 470                 475                 480

Ser Ala Val Lys Met Arg
                485

<210> SEQ ID NO 11
<211> LENGTH: 1473
<212> TYPE: DNA
<213> ORGANISM: Enterobacter cloacae
<220> FEATURE:
<221> NAME/KEY: CDS
<222> LOCATION: (1)..(1473)

<400> SEQUENCE: 11 atg aag tac cat gac ctg cgg gac ttc ttg acg ttg ctg gaa caa caa        48
Met Lys Tyr His Asp Leu Arg Asp Phe Leu Thr Leu Leu Glu Gln Gln
1               5                   10                  15 ggt gag ttg aaa cgc atc act ctg cct gtc gat cca cat ctg gag atc       96
Gly Glu Leu Lys Arg Ile Thr Leu Pro Val Asp Pro His Leu Glu Ile
            20                  25                  30
```

```
acg gaa att gcc gat aga acg ctg cgt gca ggg ggc ccg gcc ctt ttg      144
Thr Glu Ile Ala Asp Arg Thr Leu Arg Ala Gly Gly Pro Ala Leu Leu
         35                  40                  45 ttc gaa aac ccg aaa ggt tac acc atg ccg gtg ttg tgc aac cta ttc      192
Phe Glu Asn Pro Lys Gly Tyr Thr Met Pro Val Leu Cys Asn Leu Phe
 50                  55                  60 ggc acg ccg cgg cgt gtg gcc cta ggc atg ggc caa gaa gac gtc tca      240
Gly Thr Pro Arg Arg Val Ala Leu Gly Met Gly Gln Glu Asp Val Ser
 65                  70                  75                  80 tcg cta cgt gaa gtg ggg aaa ttg cta gcg ttc ttg aaa gaa ccg gaa      288
Ser Leu Arg Glu Val Gly Lys Leu Leu Ala Phe Leu Lys Glu Pro Glu
                 85                  90                  95 ccg ccg aag ggc ttc cgc gat ctg ttt gac aaa ttg cct caa ttc aag      336
Pro Pro Lys Gly Phe Arg Asp Leu Phe Asp Lys Leu Pro Gln Phe Lys
             100                 105                 110 caa gtg ctt aat atg cca acc aaa cgt ctg cgc ggc gcg ccc tgc caa      384
Gln Val Leu Asn Met Pro Thr Lys Arg Leu Arg Gly Ala Pro Cys Gln
         115                 120                 125 caa aaa att atc caa ggt gac gac gtc gac ctt aac aaa att ccg atc      432
Gln Lys Ile Ile Gln Gly Asp Asp Val Asp Leu Asn Lys Ile Pro Ile
 130                 135                 140 atg act tgc tgg ccg gaa gac gct gcg cca ctg atc acg tgg ggc ctg      480
Met Thr Cys Trp Pro Glu Asp Ala Ala Pro Leu Ile Thr Trp Gly Leu
145                 150                 155                 160 acc gtc aca cgc ggc cct cac aaa gaa cgt caa aac ttg ggg atc tat      528
Thr Val Thr Arg Gly Pro His Lys Glu Arg Gln Asn Leu Gly Ile Tyr
                165                 170                 175 cgt cag caa ctg ata ggc aag aac aaa ctg atc atg cgt tgg ttg tcg      576
Arg Gln Gln Leu Ile Gly Lys Asn Lys Leu Ile Met Arg Trp Leu Ser
            180                 185                 190 cat cgg ggt ggc gcg ctg gac ttt caa gag tgg tgc gcg gcg cgg ccg      624
His Arg Gly Gly Ala Leu Asp Phe Gln Glu Trp Cys Ala Ala Arg Pro
        195                 200                 205 ggc gaa cga ttc cct gtc tcc gtc gct ctg ggc gcc gac ccg gct acc      672
Gly Glu Arg Phe Pro Val Ser Val Ala Leu Gly Ala Asp Pro Ala Thr
    210                 215                 220 atc ttg gga gcc gtt acc cca gtc ccc gat act ttg agt gag tat gcc      720
Ile Leu Gly Ala Val Thr Pro Val Pro Asp Thr Leu Ser Glu Tyr Ala
225                 230                 235                 240 ttc gcg ggt ctc ttg cgt ggg acc aaa acc gaa gtt gtc aaa tgc gtg      768
Phe Ala Gly Leu Leu Arg Gly Thr Lys Thr Glu Val Val Lys Cys Val
                245                 250                 255 tcc aac gac ctc gaa gtg cct gcc tct gct gaa ata gtg ctc gaa ggt      816
Ser Asn Asp Leu Glu Val Pro Ala Ser Ala Glu Ile Val Leu Glu Gly
            260                 265                 270 tac atc gag gcc gga gaa atg gct ccc gaa ggt cca tac gga gac cat      864
Tyr Ile Glu Ala Gly Glu Met Ala Pro Glu Gly Pro Tyr Gly Asp His
        275                 280                 285 acc gga tat tac aac gaa gta gac caa ttc ccg gtc ttc act gta act      912
Thr Gly Tyr Tyr Asn Glu Val Asp Gln Phe Pro Val Phe Thr Val Thr
    290                 295                 300 cat atc acc caa cgt gaa gac gcc atc tac cat agc acc tac acc ggc      960
His Ile Thr Gln Arg Glu Asp Ala Ile Tyr His Ser Thr Tyr Thr Gly
305                 310                 315                 320 cgc ccg cct gac gaa ccg gct gtc tta ggg gtg gcg ttg aac gag gta     1008
Arg Pro Pro Asp Glu Pro Ala Val Leu Gly Val Ala Leu Asn Glu Val
                325                 330                 335 ttc gtc ccg atc ttg caa aaa cag ttc cct gag atc gtg gac ttt tac     1056
Phe Val Pro Ile Leu Gln Lys Gln Phe Pro Glu Ile Val Asp Phe Tyr
            340                 345                 350
```

```
ttg cct ccg gaa ggg tgt tcg tac cgt ctt gcg gtt gtg acg atg aaa    1104
Leu Pro Pro Glu Gly Cys Ser Tyr Arg Leu Ala Val Val Thr Met Lys
        355                 360                 365 aaa cag tac gcc ggt cat gct aaa cgg gtt atg atg ggc gta tgg tcg    1152
Lys Gln Tyr Ala Gly His Ala Lys Arg Val Met Met Gly Val Trp Ser
370                 375                 380 ttc ttg cgt caa ttc atg tac acc aaa ttc gta att gtt tgc gac gac    1200
Phe Leu Arg Gln Phe Met Tyr Thr Lys Phe Val Ile Val Cys Asp Asp
385                 390                 395                 400 gac gtg aac gcg cgc gat tgg aac gat gtc att tgg gct atc acc act    1248
Asp Val Asn Ala Arg Asp Trp Asn Asp Val Ile Trp Ala Ile Thr Thr
                405                 410                 415 cgt atg gac cca gcc cgc gat acc gtt ctg gtc gaa aac acc ccg atc    1296
Arg Met Asp Pro Ala Arg Asp Thr Val Leu Val Glu Asn Thr Pro Ile
        420                 425                 430 gac tac ctc gac ttc gcc tcc ccg gtt tca ggc ttg ggc tct aaa atg    1344
Asp Tyr Leu Asp Phe Ala Ser Pro Val Ser Gly Leu Gly Ser Lys Met
    435                 440                 445 ggc ttg gac gct aca aac aaa tgg cca ggt gag acg caa cgc gaa tgg    1392
Gly Leu Asp Ala Thr Asn Lys Trp Pro Gly Glu Thr Gln Arg Glu Trp
450                 455                 460 ggt cgt ccg atc aag aaa gac ccg gcc gtg act gct agg atc gat gca    1440
Gly Arg Pro Ile Lys Lys Asp Pro Ala Val Thr Ala Arg Ile Asp Ala
465                 470                 475                 480 atc tgg gac gaa ctc gcc ata ttt aaa caa cag                        1473
Ile Trp Asp Glu Leu Ala Ile Phe Lys Gln Gln
                485                 490

<210> SEQ ID NO 12
<211> LENGTH: 491
<212> TYPE: PRT
<213> ORGANISM: Enterobacter cloacae

<400> SEQUENCE: 12

Met Lys Tyr His Asp Leu Arg Asp Phe Leu Thr Leu Leu Glu Gln Gln
1               5                   10                  15

Gly Glu Leu Lys Arg Ile Thr Leu Pro Val Asp Pro His Leu Glu Ile
            20                  25                  30

Thr Glu Ile Ala Asp Arg Thr Leu Arg Ala Gly Gly Pro Ala Leu Leu
        35                  40                  45

Phe Glu Asn Pro Lys Gly Tyr Thr Met Pro Val Leu Cys Asn Leu Phe
    50                  55                  60

Gly Thr Pro Arg Arg Val Ala Leu Gly Met Gly Gln Glu Asp Val Ser
65                  70                  75                  80

Ser Leu Arg Glu Val Gly Lys Leu Leu Ala Phe Leu Lys Glu Pro Glu
                85                  90                  95

Pro Pro Lys Gly Phe Arg Asp Leu Phe Asp Lys Leu Pro Gln Phe Lys
            100                 105                 110

Gln Val Leu Asn Met Pro Thr Lys Arg Leu Arg Gly Ala Pro Cys Gln
        115                 120                 125

Gln Lys Ile Ile Gln Gly Asp Asp Val Asp Leu Asn Lys Ile Pro Ile
    130                 135                 140

Met Thr Cys Trp Pro Glu Asp Ala Ala Pro Leu Ile Thr Trp Gly Leu
145                 150                 155                 160

Thr Val Thr Arg Gly Pro His Lys Glu Arg Gln Asn Leu Gly Ile Tyr
                165                 170                 175

Arg Gln Gln Leu Ile Gly Lys Asn Lys Leu Ile Met Arg Trp Leu Ser
```

His Arg Gly Gly Ala Leu Asp Phe Gln Glu Trp Cys Ala Ala Arg Pro
            180                 185                 190
Gly Glu Arg Phe Pro Val Ser Val Ala Leu Gly Ala Asp Pro Ala Thr
        195                 200                 205
Ile Leu Gly Ala Val Thr Pro Val Pro Asp Thr Leu Ser Glu Tyr Ala
225                 230                 235                 240
Phe Ala Gly Leu Leu Arg Gly Thr Lys Thr Glu Val Val Lys Cys Val
                245                 250                 255
Ser Asn Asp Leu Glu Val Pro Ala Ser Ala Glu Ile Val Leu Glu Gly
            260                 265                 270
Tyr Ile Glu Ala Gly Glu Met Ala Pro Glu Gly Pro Tyr Gly Asp His
        275                 280                 285
Thr Gly Tyr Tyr Asn Glu Val Asp Gln Phe Pro Val Phe Thr Val Thr
    290                 295                 300
His Ile Thr Gln Arg Glu Asp Ala Ile Tyr His Ser Thr Tyr Thr Gly
305                 310                 315                 320
Arg Pro Pro Asp Glu Pro Ala Val Leu Gly Val Ala Leu Asn Glu Val
                325                 330                 335
Phe Val Pro Ile Leu Gln Lys Gln Phe Pro Glu Ile Val Asp Phe Tyr
            340                 345                 350
Leu Pro Pro Glu Gly Cys Ser Tyr Arg Leu Ala Val Val Thr Met Lys
        355                 360                 365
Lys Gln Tyr Ala Gly His Ala Lys Arg Val Met Met Gly Val Trp Ser
    370                 375                 380
Phe Leu Arg Gln Phe Met Tyr Thr Lys Phe Val Ile Val Cys Asp Asp
385                 390                 395                 400
Asp Val Asn Ala Arg Asp Trp Asn Asp Val Ile Trp Ala Ile Thr Thr
                405                 410                 415
Arg Met Asp Pro Ala Arg Asp Thr Val Leu Val Glu Asn Thr Pro Ile
            420                 425                 430
Asp Tyr Leu Asp Phe Ala Ser Pro Val Ser Gly Leu Gly Ser Lys Met
        435                 440                 445
Gly Leu Asp Ala Thr Asn Lys Trp Pro Gly Glu Thr Gln Arg Glu Trp
    450                 455                 460
Gly Arg Pro Ile Lys Lys Asp Pro Ala Val Thr Ala Arg Ile Asp Ala
465                 470                 475                 480
Ile Trp Asp Glu Leu Ala Ile Phe Lys Gln Gln
                485                 490

<210> SEQ ID NO 13
<211> LENGTH: 1500
<212> TYPE: DNA
<213> ORGANISM: Klebsiella variicola
<220> FEATURE:
<221> NAME/KEY: CDS
<222> LOCATION: (1)..(1500)

<400> SEQUENCE: 13 atg acc gca ccg att cag gat ctg cgc gac gct atc gcg ctg cta caa    48
Met Thr Ala Pro Ile Gln Asp Leu Arg Asp Ala Ile Ala Leu Leu Gln
1               5                   10                  15 cag cat gac aat cag tac ctc gaa acc gat cat ccg gtt gac cct aac    96
Gln His Asp Asn Gln Tyr Leu Glu Thr Asp His Pro Val Asp Pro Asn
            20                  25                  30 gct gag ctg gcc ggc gtc tat cgc cac atc ggc gcg ggc ggc acc gtg   144

```
                Ala Glu Leu Ala Gly Val Tyr Arg His Ile Gly Ala Gly Gly Thr Val
                            35                  40                  45 aag cgc ccc acc cgc atc ggc ccg gcg atg atg ttt aac aat att aag        192
Lys Arg Pro Thr Arg Ile Gly Pro Ala Met Met Phe Asn Asn Ile Lys
 50                  55                  60 ggc tat ccg cac tcg cgc att ctg gtg ggc atg cac gcc agc cgc cag        240
Gly Tyr Pro His Ser Arg Ile Leu Val Gly Met His Ala Ser Arg Gln
 65                  70                  75                  80 cgg gcc gca ctg ctg ctg ggc tgc gaa gcc tca cag ctg gcg ctg gag        288
Arg Ala Ala Leu Leu Leu Gly Cys Glu Ala Ser Gln Leu Ala Leu Glu
                     85                  90                  95 gta ggc aaa gcg gtg aaa aaa ccg gtc gcg ccg gtg gtc gtt ccg gcc        336
Val Gly Lys Ala Val Lys Lys Pro Val Ala Pro Val Val Val Pro Ala
            100                 105                 110 agc agc gcc ccc tgt cag gaa cag gtc ttt ctg gcc gac gat ccg gat        384
Ser Ser Ala Pro Cys Gln Glu Gln Val Phe Leu Ala Asp Asp Pro Asp
            115                 120                 125 ttt gat ttg cgc acc ctg ctc ccg gcg ccc acc aac acc ccg atc gac        432
Phe Asp Leu Arg Thr Leu Leu Pro Ala Pro Thr Asn Thr Pro Ile Asp
    130                 135                 140 gcc ggt ccc ttc ttc tgc ctg ggc ctg gcg ctg gcc agc gat ccc gac        480
Ala Gly Pro Phe Phe Cys Leu Gly Leu Ala Leu Ala Ser Asp Pro Asp
145                 150                 155                 160 gac gcc tcg ctc acc gac gtc acc atc cac cgc ttg tgc gtc cag ggc        528
Asp Ala Ser Leu Thr Asp Val Thr Ile His Arg Leu Cys Val Gln Gly
                165                 170                 175 cgg gat gag ctg tcg atg ttt ctc gcc gct ggc cgc cat atc gaa gtg        576
Arg Asp Glu Leu Ser Met Phe Leu Ala Ala Gly Arg His Ile Glu Val
            180                 185                 190 ttt cgc cag aaa gcc gag gcc gcc ggc aaa ccg ctg ccg ata acc atc        624
Phe Arg Gln Lys Ala Glu Ala Ala Gly Lys Pro Leu Pro Ile Thr Ile
            195                 200                 205 aat atg gga ctc gat ccg gct atc tat atc ggc gcc tgc ttt gaa gcg        672
Asn Met Gly Leu Asp Pro Ala Ile Tyr Ile Gly Ala Cys Phe Glu Ala
    210                 215                 220 cca acc aca ccg ttt ggc tat aac gaa ctg ggc gtc gcc ggt gcg ctg        720
Pro Thr Thr Pro Phe Gly Tyr Asn Glu Leu Gly Val Ala Gly Ala Leu
225                 230                 235                 240 cgt cag cgt ccg gta gag ctg gta cag ggc gtc agc gtc ccg gag aaa        768
Arg Gln Arg Pro Val Glu Leu Val Gln Gly Val Ser Val Pro Glu Lys
                245                 250                 255 gcc atc gct cgc gcc gag atc gtt atc gaa ggg gaa ctg ctg ccg ggg        816
Ala Ile Ala Arg Ala Glu Ile Val Ile Glu Gly Glu Leu Leu Pro Gly
            260                 265                 270 gta cgc gtc aga gaa gat cag cac acc aac agc ggc cat gcg atg ccg        864
Val Arg Val Arg Glu Asp Gln His Thr Asn Ser Gly His Ala Met Pro
            275                 280                 285 gaa ttt cct ggt tac tgc ggc ggc gcc aat cca tcg ctg ccg gtg ata        912
Glu Phe Pro Gly Tyr Cys Gly Gly Ala Asn Pro Ser Leu Pro Val Ile
    290                 295                 300 aaa gtc aaa gcg gtg acc atg cga aac aat gcg att ctg cag acg ctg        960
Lys Val Lys Ala Val Thr Met Arg Asn Asn Ala Ile Leu Gln Thr Leu
305                 310                 315                 320 gta ggg ccg ggc gaa gag cat acc acc ctc gcc ggg ctg cca acg gaa       1008
Val Gly Pro Gly Glu Glu His Thr Thr Leu Ala Gly Leu Pro Thr Glu
                325                 330                 335 gcc agt atc tgg aat gcc gtt gaa gcc gct atc ccg ggc ttt tta caa       1056
Ala Ser Ile Trp Asn Ala Val Glu Ala Ala Ile Pro Gly Phe Leu Gln
            340                 345                 350
```

| | | | | | | | | | | | | | | | | |
|---|---|---|---|---|---|---|---|---|---|---|---|---|---|---|---|---|
| aat | gtc | tac | gcc | cac | acc | gcg | ggc | ggc | ggt | aaa | ttc | ctc | ggg | atc | ctg | 1104 |
| Asn | Val | Tyr | Ala | His | Thr | Ala | Gly | Gly | Gly | Lys | Phe | Leu | Gly | Ile | Leu | |
| | 355 | | | | 360 | | | | | 365 | | | | | | |
| cag | gtg | aaa | aaa | cgc | cag | ccc | gcc | gac | gaa | ggg | cgt | cag | ggg | cag | gcc | 1152 |
| Gln | Val | Lys | Lys | Arg | Gln | Pro | Ala | Asp | Glu | Gly | Arg | Gln | Gly | Gln | Ala | |
| | 370 | | | | 375 | | | | | 380 | | | | | | |
| gcg | ctg | gta | gcg | ctg | gcg | acc | tat | tcc | gag | ctg | aaa | aat | atc | att | ctg | 1200 |
| Ala | Leu | Val | Ala | Leu | Ala | Thr | Tyr | Ser | Glu | Leu | Lys | Asn | Ile | Ile | Leu | |
| 385 | | | | | 390 | | | | | 395 | | | | | 400 | |
| gtc | gat | gaa | gat | gtc | gat | atc | ttt | gac | agc | gac | gat | atc | ctg | tgg | gcc | 1248 |
| Val | Asp | Glu | Asp | Val | Asp | Ile | Phe | Asp | Ser | Asp | Asp | Ile | Leu | Trp | Ala | |
| | | | | 405 | | | | | 410 | | | | | 415 | | |
| atg | acc | acc | cgt | atg | cag | ggg | gat | gtc | agc | atc | acg | acg | atc | ccc | ggc | 1296 |
| Met | Thr | Thr | Arg | Met | Gln | Gly | Asp | Val | Ser | Ile | Thr | Thr | Ile | Pro | Gly | |
| | | | 420 | | | | | 425 | | | | | 430 | | | |
| atc | cgt | ggt | cac | cag | ctg | gat | cct | tcc | cag | acc | ccg | gca | tac | agc | ccg | 1344 |
| Ile | Arg | Gly | His | Gln | Leu | Asp | Pro | Ser | Gln | Thr | Pro | Ala | Tyr | Ser | Pro | |
| | | 435 | | | | | 440 | | | | | 445 | | | | |
| tcg | atc | cgc | gga | gag | ggt | atc | agt | tgc | aag | acg | att | ttc | gat | tgc | acg | 1392 |
| Ser | Ile | Arg | Gly | Glu | Gly | Ile | Ser | Cys | Lys | Thr | Ile | Phe | Asp | Cys | Thr | |
| 450 | | | | | 455 | | | | | 460 | | | | | | |
| gtg | ccg | tgg | gcg | cta | aaa | tca | cac | ttc | gaa | cgc | gca | ccg | ttt | gcc | gat | 1440 |
| Val | Pro | Trp | Ala | Leu | Lys | Ser | His | Phe | Glu | Arg | Ala | Pro | Phe | Ala | Asp | |
| 465 | | | | | 470 | | | | | 475 | | | | | 480 | |
| gtc | gat | ccg | cgt | ccg | ttt | gcg | ccg | gag | tat | ttt | gcc | cgg | ctg | gaa | aaa | 1488 |
| Val | Asp | Pro | Arg | Pro | Phe | Ala | Pro | Glu | Tyr | Phe | Ala | Arg | Leu | Glu | Lys | |
| | | | | 485 | | | | | 490 | | | | | 495 | | |
| aac | cac | ggt | cag | | | | | | | | | | | | | 1500 |
| Asn | His | Gly | Gln | | | | | | | | | | | | | |
| | | | 500 | | | | | | | | | | | | | |

<210> SEQ ID NO 14
<211> LENGTH: 500
<212> TYPE: PRT
<213> ORGANISM: Klebsiella variicola

<400> SEQUENCE: 14

```
Met Thr Ala Pro Ile Gln Asp Leu Arg Asp Ala Ile Ala Leu Leu Gln
1               5                   10                  15

Gln His Asp Asn Gln Tyr Leu Glu Thr Asp His Pro Val Asp Pro Asn
                20                  25                  30

Ala Glu Leu Ala Gly Val Tyr Arg His Ile Gly Ala Gly Gly Thr Val
            35                  40                  45

Lys Arg Pro Thr Arg Ile Gly Pro Ala Met Met Phe Asn Asn Ile Lys
    50                  55                  60

Gly Tyr Pro His Ser Arg Ile Leu Val Gly Met His Ala Ser Arg Gln
65                  70                  75                  80

Arg Ala Ala Leu Leu Leu Gly Cys Glu Ala Ser Gln Leu Ala Leu Glu
                85                  90                  95

Val Gly Lys Ala Val Lys Lys Pro Val Ala Pro Val Val Pro Ala
                100                 105                 110

Ser Ser Ala Pro Cys Gln Glu Gln Val Phe Leu Ala Asp Asp Pro Asp
            115                 120                 125

Phe Asp Leu Arg Thr Leu Leu Pro Ala Pro Thr Asn Thr Pro Ile Asp
    130                 135                 140

Ala Gly Pro Phe Phe Cys Leu Gly Leu Ala Leu Ala Ser Asp Pro Asp
145                 150                 155                 160

Asp Ala Ser Leu Thr Asp Val Thr Ile His Arg Leu Cys Val Gln Gly
```

```
                     165                 170                 175
Arg Asp Glu Leu Ser Met Phe Leu Ala Ala Gly Arg His Ile Glu Val
        180                 185                 190

Phe Arg Gln Lys Ala Glu Ala Ala Gly Lys Pro Leu Pro Ile Thr Ile
    195                 200                 205

Asn Met Gly Leu Asp Pro Ala Ile Tyr Ile Gly Ala Cys Phe Glu Ala
210                 215                 220

Pro Thr Thr Pro Phe Gly Tyr Asn Glu Leu Gly Val Ala Gly Ala Leu
225                 230                 235                 240

Arg Gln Arg Pro Val Glu Leu Val Gln Gly Val Ser Val Pro Glu Lys
                245                 250                 255

Ala Ile Ala Arg Ala Glu Ile Val Ile Glu Gly Glu Leu Leu Pro Gly
            260                 265                 270

Val Arg Val Arg Glu Asp Gln His Thr Asn Ser Gly His Ala Met Pro
        275                 280                 285

Glu Phe Pro Gly Tyr Cys Gly Gly Ala Asn Pro Ser Leu Pro Val Ile
    290                 295                 300

Lys Val Lys Ala Val Thr Met Arg Asn Asn Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Trp Asn Ala Val Glu Ala Ala Ile Pro Gly Phe Leu Gln
            340                 345                 350

Asn Val Tyr Ala His Thr Ala Gly Gly Gly Lys Phe Leu Gly Ile Leu
        355                 360                 365

Gln Val Lys Lys Arg Gln Pro Ala Asp Glu Gly Arg Gln Gly Gln Ala
    370                 375                 380

Ala Leu Val Ala Leu Ala Thr Tyr Ser Glu Leu Lys Asn Ile Ile Leu
385                 390                 395                 400

Val Asp Glu Asp Val Asp Ile Phe Asp Ser Asp Ile Leu Trp Ala
                405                 410                 415

Met Thr Thr Arg Met Gln Gly Asp Val Ser Ile Thr Thr Ile Pro Gly
            420                 425                 430

Ile Arg Gly His Gln Leu Asp Pro Ser Gln Thr Pro Ala Tyr Ser Pro
        435                 440                 445

Ser Ile Arg Gly Glu Gly Ile Ser Cys Lys Thr Ile Phe Asp Cys Thr
    450                 455                 460

Val Pro Trp Ala Leu Lys Ser His Phe Glu Arg Ala Pro Phe Ala Asp
465                 470                 475                 480

Val Asp Pro Arg Pro Phe Ala Pro Glu Tyr Phe Ala Arg Leu Glu Lys
                485                 490                 495

Asn His Gly Gln
            500

<210> SEQ ID NO 15
<211> LENGTH: 933
<212> TYPE: DNA
<213> ORGANISM: Candida albicans
<220> FEATURE:
<221> NAME/KEY: CDS
<222> LOCATION: (1)..(933)

<400> SEQUENCE: 15 atg gaa gtt aaa atc ttc aac acg cag gac gtg caa gac ttc ttg cgc      48
Met Glu Val Lys Ile Phe Asn Thr Gln Asp Val Gln Asp Phe Leu Arg
1               5                  10                  15
```

```
gtg gcc tca ggt ctg gag caa gaa ggt ggt aac cca cgt gtt aag caa      96
Val Ala Ser Gly Leu Glu Gln Glu Gly Gly Asn Pro Arg Val Lys Gln
         20                  25                  30 atc atc cat cgg gta ttg tcg gac ctg tac aaa gcc atc gag gat ttg     144
Ile Ile His Arg Val Leu Ser Asp Leu Tyr Lys Ala Ile Glu Asp Leu
     35                  40                  45 aac atc acc tct gac gag tac tgg gcg ggt gtt gcc tac tta aac cag     192
Asn Ile Thr Ser Asp Glu Tyr Trp Ala Gly Val Ala Tyr Leu Asn Gln
 50                  55                  60 ttg ggc gcg aac cag gaa gcc ggg ctg ttg tca cct ggt ctt ggc ttc     240
Leu Gly Ala Asn Gln Glu Ala Gly Leu Leu Ser Pro Gly Leu Gly Phe
 65                  70                  75                  80 gac cat tac ttg gat atg cga atg gac gcg gaa gac gcg gcc cta ggg     288
Asp His Tyr Leu Asp Met Arg Met Asp Ala Glu Asp Ala Ala Leu Gly
                 85                  90                  95 att gaa aac gcg acg ccc agg aca atc gaa ggg ccg ctg tac gtt gcg     336
Ile Glu Asn Ala Thr Pro Arg Thr Ile Glu Gly Pro Leu Tyr Val Ala
            100                 105                 110 ggc gcg cct gag agt gtg ggg tat gcc cgt atg gac gac ggc tct gac     384
Gly Ala Pro Glu Ser Val Gly Tyr Ala Arg Met Asp Asp Gly Ser Asp
        115                 120                 125 ccg aac ggc cat acc cta atc ctg cac ggt aca atc ttc gac gcc gac     432
Pro Asn Gly His Thr Leu Ile Leu His Gly Thr Ile Phe Asp Ala Asp
    130                 135                 140 gga aaa cct ctg ccc aat gcg aag gtc gaa att tgg cat gct aat acg     480
Gly Lys Pro Leu Pro Asn Ala Lys Val Glu Ile Trp His Ala Asn Thr
145                 150                 155                 160 aaa gga ttc tac tca cac ttc gac cct act ggt gag cag caa gcc ttc     528
Lys Gly Phe Tyr Ser His Phe Asp Pro Thr Gly Glu Gln Gln Ala Phe
                165                 170                 175 aac atg cgc cga agt atc atc acc gac gaa aac ggt caa tac agg gtg     576
Asn Met Arg Arg Ser Ile Ile Thr Asp Glu Asn Gly Gln Tyr Arg Val
            180                 185                 190 cgc acc atc ctg ccc gca ggt tac ggc tgc ccc ccg gaa ggc cca acg     624
Arg Thr Ile Leu Pro Ala Gly Tyr Gly Cys Pro Pro Glu Gly Pro Thr
        195                 200                 205 caa caa ctt ttg aac caa ctg ggc cgc cat ggc aac cgt ccc gct cat     672
Gln Gln Leu Leu Asn Gln Leu Gly Arg His Gly Asn Arg Pro Ala His
    210                 215                 220 ata cat tac ttc gtt tcg gcg gac ggt cat cgc aaa ctg act acc caa     720
Ile His Tyr Phe Val Ser Ala Asp Gly His Arg Lys Leu Thr Thr Gln
225                 230                 235                 240 atc aac gta gcc gga gac ccg tac acg tac gac gac ttc gcg tac gcc     768
Ile Asn Val Ala Gly Asp Pro Tyr Thr Tyr Asp Asp Phe Ala Tyr Ala
                245                 250                 255 act cgc gag ggc ttg gtc gtt gac gcg gtg gaa cat acg gac ccg gaa     816
Thr Arg Glu Gly Leu Val Val Asp Ala Val Glu His Thr Asp Pro Glu
            260                 265                 270 gct atc aaa gct aac gac gtc gaa ggt cct ttc gcg gaa atg gtc ttc     864
Ala Ile Lys Ala Asn Asp Val Glu Gly Pro Phe Ala Glu Met Val Phe
        275                 280                 285 gac ttg aaa ctg acg cgg ttg gtc gac ggt gtt gac aac caa gtc gtg     912
Asp Leu Lys Leu Thr Arg Leu Val Asp Gly Val Asp Asn Gln Val Val
    290                 295                 300 gac cgt ccg cgc ctg gcc gtt                                         933
Asp Arg Pro Arg Leu Ala Val
305                 310

<210> SEQ ID NO 16
```

```
<211> LENGTH: 311
<212> TYPE: PRT
<213> ORGANISM: Candida albicans

<400> SEQUENCE: 16

Met Glu Val Lys Ile Phe Asn Thr Gln Asp Val Gln Asp Phe Leu Arg
1               5                   10                  15

Val Ala Ser Gly Leu Glu Gln Glu Gly Gly Asn Pro Arg Val Lys Gln
            20                  25                  30

Ile Ile His Arg Val Leu Ser Asp Leu Tyr Lys Ala Ile Glu Asp Leu
        35                  40                  45

Asn Ile Thr Ser Asp Glu Tyr Trp Ala Gly Val Ala Tyr Leu Asn Gln
50                  55                  60

Leu Gly Ala Asn Gln Glu Ala Gly Leu Leu Ser Pro Gly Leu Gly Phe
65                  70                  75                  80

Asp His Tyr Leu Asp Met Arg Met Asp Ala Glu Asp Ala Ala Leu Gly
                85                  90                  95

Ile Glu Asn Ala Thr Pro Arg Thr Ile Glu Gly Pro Leu Tyr Val Ala
            100                 105                 110

Gly Ala Pro Glu Ser Val Gly Tyr Ala Arg Met Asp Asp Gly Ser Asp
        115                 120                 125

Pro Asn Gly His Thr Leu Ile Leu His Gly Thr Ile Phe Asp Ala Asp
130                 135                 140

Gly Lys Pro Leu Pro Asn Ala Lys Val Glu Ile Trp His Ala Asn Thr
145                 150                 155                 160

Lys Gly Phe Tyr Ser His Phe Asp Pro Thr Gly Glu Gln Gln Ala Phe
                165                 170                 175

Asn Met Arg Arg Ser Ile Ile Thr Asp Glu Asn Gly Gln Tyr Arg Val
            180                 185                 190

Arg Thr Ile Leu Pro Ala Gly Tyr Gly Cys Pro Pro Glu Gly Pro Thr
        195                 200                 205

Gln Gln Leu Leu Asn Gln Leu Gly Arg His Gly Asn Arg Pro Ala His
210                 215                 220

Ile His Tyr Phe Val Ser Ala Asp Gly His Arg Lys Leu Thr Thr Gln
225                 230                 235                 240

Ile Asn Val Ala Gly Asp Pro Tyr Thr Tyr Asp Asp Phe Ala Tyr Ala
                245                 250                 255

Thr Arg Glu Gly Leu Val Val Asp Ala Val Glu His Thr Asp Pro Glu
            260                 265                 270

Ala Ile Lys Ala Asn Asp Val Glu Gly Pro Phe Ala Glu Met Val Phe
        275                 280                 285

Asp Leu Lys Leu Thr Arg Leu Val Asp Gly Val Asp Asn Gln Val Val
290                 295                 300

Asp Arg Pro Arg Leu Ala Val
305                 310

<210> SEQ ID NO 17
<211> LENGTH: 933
<212> TYPE: DNA
<213> ORGANISM: Acinetobacter spp.
<220> FEATURE:
<221> NAME/KEY: CDS
<222> LOCATION: (1)..(933)

<400> SEQUENCE: 17 atg gaa gtt aaa ata ttc aat act cag gat gtg caa gat ttt tta cgt      48
Met Glu Val Lys Ile Phe Asn Thr Gln Asp Val Gln Asp Phe Leu Arg
```

-continued

```
 1                   5                   10                  15 gtt gca agc gga ctt gag caa gaa ggt ggc aat ccg cgt gta aag cag         96
Val Ala Ser Gly Leu Glu Gln Glu Gly Gly Asn Pro Arg Val Lys Gln
            20                  25                  30 atc atc cat cgt gtg ctt tca gat tta tat aaa gcc att gaa gat ttg        144
Ile Ile His Arg Val Leu Ser Asp Leu Tyr Lys Ala Ile Glu Asp Leu
                35                  40                  45 aat atc act tca gat gaa tac tgg gca ggt gtg gca tat tta aat cag        192
Asn Ile Thr Ser Asp Glu Tyr Trp Ala Gly Val Ala Tyr Leu Asn Gln
 50                  55                  60 cta ggt gcc aat caa gaa gct ggt tta ctc tcg gca ggc ttg ggt ttt        240
Leu Gly Ala Asn Gln Glu Ala Gly Leu Leu Ser Ala Gly Leu Gly Phe
 65                  70                  75                  80 gac cat tac ctc gat atg cgt atg gat gcc gaa gat gcc gca cta ggt        288
Asp His Tyr Leu Asp Met Arg Met Asp Ala Glu Asp Ala Ala Leu Gly
                85                  90                  95 att gaa aat gcg aca cca cgt acc att gaa ggc cca cta tac gtg gca        336
Ile Glu Asn Ala Thr Pro Arg Thr Ile Glu Gly Pro Leu Tyr Val Ala
                100                 105                 110 ggt gcg cct gaa tcg gta ggt tat gcg cgc atg gat gac gga agt gat        384
Gly Ala Pro Glu Ser Val Gly Tyr Ala Arg Met Asp Asp Gly Ser Asp
                115                 120                 125 cca aat ggt cat acc ctg att cta cat ggc acg atc ttt gat gca gat        432
Pro Asn Gly His Thr Leu Ile Leu His Gly Thr Ile Phe Asp Ala Asp
 130                 135                 140 gga aaa cct tta ccc aat gcc aaa gtt gaa atc tgg cat gcc aat acc        480
Gly Lys Pro Leu Pro Asn Ala Lys Val Glu Ile Trp His Ala Asn Thr
145                 150                 155                 160 aaa ggc ttt tat tca cac ttc gac cca aca ggc gag cag cag gcg ttc        528
Lys Gly Phe Tyr Ser His Phe Asp Pro Thr Gly Glu Gln Gln Ala Phe
                165                 170                 175 aat atg cgc cgt agt att att acc gat gaa aac ggt cag tat cgc gtt        576
Asn Met Arg Arg Ser Ile Ile Thr Asp Glu Asn Gly Gln Tyr Arg Val
                180                 185                 190 cgt acc att ttg cct gcg ggt tat ggt tgc cca cca gaa ggt cca acg        624
Arg Thr Ile Leu Pro Ala Gly Tyr Gly Cys Pro Pro Glu Gly Pro Thr
                195                 200                 205 caa cag ttg ctg aat cag ttg ggc cgt cat ggt aac cgc cct gcg cac        672
Gln Gln Leu Leu Asn Gln Leu Gly Arg His Gly Asn Arg Pro Ala His
 210                 215                 220 att cac tat ttt gtt tct gcc gat gga cac cgc aaa cta act acg caa        720
Ile His Tyr Phe Val Ser Ala Asp Gly His Arg Lys Leu Thr Thr Gln
225                 230                 235                 240 att aat gtg gct ggc gat ccg tac acc tat gac gac ttt gct tat gca        768
Ile Asn Val Ala Gly Asp Pro Tyr Thr Tyr Asp Asp Phe Ala Tyr Ala
                245                 250                 255 acc cgt gaa ggc ttg gtg gtt gat gca gtg gaa cac acc gat cct gaa        816
Thr Arg Glu Gly Leu Val Val Asp Ala Val Glu His Thr Asp Pro Glu
                260                 265                 270 gcc att aag gcc aat gat gtt gaa ggc cca ttc gct gaa atg gtt ttc        864
Ala Ile Lys Ala Asn Asp Val Glu Gly Pro Phe Ala Glu Met Val Phe
                275                 280                 285 gat cta aaa ttg acg cgt ttg gtt gat ggt gta gat aac caa gtt gtt        912
Asp Leu Lys Leu Thr Arg Leu Val Asp Gly Val Asp Asn Gln Val Val
                290                 295                 300 gat cgt cca cgt cta gcg gtg                                            933
Asp Arg Pro Arg Leu Ala Val
305                 310
```

<210> SEQ ID NO 18
<211> LENGTH: 311
<212> TYPE: PRT
<213> ORGANISM: Acinetobacter spp.

<400> SEQUENCE: 18

Met Glu Val Lys Ile Phe Asn Thr Gln Asp Val Gln Asp Phe Leu Arg
1               5                   10                  15

Val Ala Ser Gly Leu Glu Gln Glu Gly Asn Pro Arg Val Lys Gln
            20                  25                  30

Ile Ile His Arg Val Leu Ser Asp Leu Tyr Lys Ala Ile Glu Asp Leu
        35                  40                  45

Asn Ile Thr Ser Asp Glu Tyr Trp Ala Gly Val Ala Tyr Leu Asn Gln
    50                  55                  60

Leu Gly Ala Asn Gln Glu Ala Gly Leu Leu Ser Ala Gly Leu Gly Phe
65                  70                  75                  80

Asp His Tyr Leu Asp Met Arg Met Asp Ala Glu Asp Ala Ala Leu Gly
                85                  90                  95

Ile Glu Asn Ala Thr Pro Arg Thr Ile Glu Gly Pro Leu Tyr Val Ala
            100                 105                 110

Gly Ala Pro Glu Ser Val Gly Tyr Ala Arg Met Asp Asp Gly Ser Asp
        115                 120                 125

Pro Asn Gly His Thr Leu Ile Leu His Gly Thr Ile Phe Asp Ala Asp
    130                 135                 140

Gly Lys Pro Leu Pro Asn Ala Lys Val Glu Ile Trp His Ala Asn Thr
145                 150                 155                 160

Lys Gly Phe Tyr Ser His Phe Asp Pro Thr Gly Glu Gln Gln Ala Phe
                165                 170                 175

Asn Met Arg Arg Ser Ile Ile Thr Asp Glu Asn Gly Gln Tyr Arg Val
            180                 185                 190

Arg Thr Ile Leu Pro Ala Gly Tyr Gly Cys Pro Pro Glu Gly Pro Thr
        195                 200                 205

Gln Gln Leu Leu Asn Gln Leu Gly Arg His Gly Asn Arg Pro Ala His
    210                 215                 220

Ile His Tyr Phe Val Ser Ala Asp Gly His Arg Lys Leu Thr Thr Gln
225                 230                 235                 240

Ile Asn Val Ala Gly Asp Pro Tyr Thr Tyr Asp Asp Phe Ala Tyr Ala
                245                 250                 255

Thr Arg Glu Gly Leu Val Val Asp Ala Val Glu His Thr Asp Pro Glu
            260                 265                 270

Ala Ile Lys Ala Asn Asp Val Glu Gly Pro Phe Ala Glu Met Val Phe
        275                 280                 285

Asp Leu Lys Leu Thr Arg Leu Val Asp Gly Val Asp Asn Gln Val Val
    290                 295                 300

Asp Arg Pro Arg Leu Ala Val
305                 310

<210> SEQ ID NO 19
<211> LENGTH: 933
<212> TYPE: DNA
<213> ORGANISM: Pseudomonas putida
<220> FEATURE:
<221> NAME/KEY: CDS
<222> LOCATION: (1)..(933)

<400> SEQUENCE: 19 atg acc gtg aaa att tcc cac act gcc gac att caa gcc ttc ttc aac    48

```
Met Thr Val Lys Ile Ser His Thr Ala Asp Ile Gln Ala Phe Phe Asn
1               5                   10                  15 cgg gta gct ggc ctg gac cat gcc gaa gga aac ccg cgc ttc aag cag        96
Arg Val Ala Gly Leu Asp His Ala Glu Gly Asn Pro Arg Phe Lys Gln
                20                  25                  30 atc att ctg cgc gtg ctg caa gac acc gcc cgc ctg atc gaa gac ctg        144
Ile Ile Leu Arg Val Leu Gln Asp Thr Ala Arg Leu Ile Glu Asp Leu
                35                  40                  45 gag att acc gag gac gag ttc tgg cac gcc gtc gac tac ctc aac cgc        192
Glu Ile Thr Glu Asp Glu Phe Trp His Ala Val Asp Tyr Leu Asn Arg
        50                  55                  60 ctg ggc ggc cgt aac gag gca ggc ctg ctg gct gct ggc ctg ggt atc        240
Leu Gly Gly Arg Asn Glu Ala Gly Leu Leu Ala Ala Gly Leu Gly Ile
65                  70                  75                  80 gag cac ttc ctc gac ctg ctg cag gat gcc aag gat gcc gaa gcc ggc        288
Glu His Phe Leu Asp Leu Leu Gln Asp Ala Lys Asp Ala Glu Ala Gly
                85                  90                  95 ctt ggc ggc ggc acc ccg cgc acc atc gaa ggc ccg ttg tac gtt gcc        336
Leu Gly Gly Gly Thr Pro Arg Thr Ile Glu Gly Pro Leu Tyr Val Ala
                100                 105                 110 ggg gcg ccg ctg gcc cag ggc gaa gcg cgc atg gac gac ggc act gac        384
Gly Ala Pro Leu Ala Gln Gly Glu Ala Arg Met Asp Asp Gly Thr Asp
            115                 120                 125 cca ggc gtg gtg atg ttc ctt cag ggc cag gtg ttc gat gcc gac ggc        432
Pro Gly Val Val Met Phe Leu Gln Gly Gln Val Phe Asp Ala Asp Gly
        130                 135                 140 aag ccg ttg gcc ggt gcc acc gtc gac ctg tgg cac gcc aat acc cag        480
Lys Pro Leu Ala Gly Ala Thr Val Asp Leu Trp His Ala Asn Thr Gln
145                 150                 155                 160 ggc acc tat tcg tac ttc gat tcg acc cag tcc gag ttc aac ctg cgt        528
Gly Thr Tyr Ser Tyr Phe Asp Ser Thr Gln Ser Glu Phe Asn Leu Arg
                165                 170                 175 cgg cgt atc atc acc gat gcc gag ggc cgc tac cgc gcg cgc tcg atc        576
Arg Arg Ile Ile Thr Asp Ala Glu Gly Arg Tyr Arg Ala Arg Ser Ile
                180                 185                 190 gtg ccg tcc ggg tat ggc tgc gac ccg cag ggc cca acc cag gaa tgc        624
Val Pro Ser Gly Tyr Gly Cys Asp Pro Gln Gly Pro Thr Gln Glu Cys
            195                 200                 205 ctg gac ctg ctc ggc cgc cac ggc cag cgc ccg gcg cac gtg cac ttc        672
Leu Asp Leu Leu Gly Arg His Gly Gln Arg Pro Ala His Val His Phe
        210                 215                 220 ttc atc tcg gca ccg ggg cac cgc cac ctg acc acg cag atc aac ttt        720
Phe Ile Ser Ala Pro Gly His Arg His Leu Thr Thr Gln Ile Asn Phe
225                 230                 235                 240 gct ggc gac aag tac ctg tgg gac gac ttt gcc tat gcc acc cgc gac        768
Ala Gly Asp Lys Tyr Leu Trp Asp Asp Phe Ala Tyr Ala Thr Arg Asp
                245                 250                 255 ggg ctg atc ggc gaa ctg cgt ttt gtc gag gat gcg gcg gcg gcg cgc        816
Gly Leu Ile Gly Glu Leu Arg Phe Val Glu Asp Ala Ala Ala Ala Arg
                260                 265                 270 gac cgc ggt gtg caa ggc gag cgc ttt gcc gag ctg tca ttc gac ttc        864
Asp Arg Gly Val Gln Gly Glu Arg Phe Ala Glu Leu Ser Phe Asp Phe
            275                 280                 285 cgc ttg cag ggt gcc aag tcg cct gac gcc gag gcg cga agc cat cgg        912
Arg Leu Gln Gly Ala Lys Ser Pro Asp Ala Glu Ala Arg Ser His Arg
        290                 295                 300 ccg cgg gcg ttg cag gag ggc                                            933
Pro Arg Ala Leu Gln Glu Gly
305                 310
```

<210> SEQ ID NO 20
<211> LENGTH: 311
<212> TYPE: PRT
<213> ORGANISM: Pseudomonas putida

<400> SEQUENCE: 20

| Met | Thr | Val | Lys | Ile | Ser | His | Thr | Ala | Asp | Ile | Gln | Ala | Phe | Phe | Asn |
|---|---|---|---|---|---|---|---|---|---|---|---|---|---|---|---|
| 1 | | | | 5 | | | | | 10 | | | | | 15 | |

| Arg | Val | Ala | Gly | Leu | Asp | His | Ala | Glu | Gly | Asn | Pro | Arg | Phe | Lys | Gln |
|---|---|---|---|---|---|---|---|---|---|---|---|---|---|---|---|
| | | | 20 | | | | | 25 | | | | | 30 | | |

| Ile | Ile | Leu | Arg | Val | Leu | Gln | Asp | Thr | Ala | Arg | Leu | Ile | Glu | Asp | Leu |
|---|---|---|---|---|---|---|---|---|---|---|---|---|---|---|---|
| | | 35 | | | | | 40 | | | | | 45 | | | |

| Glu | Ile | Thr | Glu | Asp | Glu | Phe | Trp | His | Ala | Val | Asp | Tyr | Leu | Asn | Arg |
|---|---|---|---|---|---|---|---|---|---|---|---|---|---|---|---|
| 50 | | | | | 55 | | | | | 60 | | | | | |

| Leu | Gly | Gly | Arg | Asn | Glu | Ala | Gly | Leu | Leu | Ala | Ala | Gly | Leu | Gly | Ile |
|---|---|---|---|---|---|---|---|---|---|---|---|---|---|---|---|
| 65 | | | | | 70 | | | | | 75 | | | | | 80 |

| Glu | His | Phe | Leu | Asp | Leu | Leu | Gln | Asp | Ala | Lys | Asp | Ala | Glu | Ala | Gly |
|---|---|---|---|---|---|---|---|---|---|---|---|---|---|---|---|
| | | | | 85 | | | | | 90 | | | | | 95 | |

| Leu | Gly | Gly | Gly | Thr | Pro | Arg | Thr | Ile | Glu | Gly | Pro | Leu | Tyr | Val | Ala |
|---|---|---|---|---|---|---|---|---|---|---|---|---|---|---|---|
| | | | 100 | | | | | 105 | | | | | 110 | | |

| Gly | Ala | Pro | Leu | Ala | Gln | Gly | Glu | Ala | Arg | Met | Asp | Asp | Gly | Thr | Asp |
|---|---|---|---|---|---|---|---|---|---|---|---|---|---|---|---|
| | | 115 | | | | | 120 | | | | | 125 | | | |

| Pro | Gly | Val | Val | Met | Phe | Leu | Gln | Gly | Gln | Val | Phe | Asp | Ala | Asp | Gly |
|---|---|---|---|---|---|---|---|---|---|---|---|---|---|---|---|
| 130 | | | | | 135 | | | | | 140 | | | | | |

| Lys | Pro | Leu | Ala | Gly | Ala | Thr | Val | Asp | Leu | Trp | His | Ala | Asn | Thr | Gln |
|---|---|---|---|---|---|---|---|---|---|---|---|---|---|---|---|
| 145 | | | | | 150 | | | | | 155 | | | | | 160 |

| Gly | Thr | Tyr | Ser | Tyr | Phe | Asp | Ser | Thr | Gln | Ser | Glu | Phe | Asn | Leu | Arg |
|---|---|---|---|---|---|---|---|---|---|---|---|---|---|---|---|
| | | | | 165 | | | | | 170 | | | | | 175 | |

| Arg | Arg | Ile | Ile | Thr | Asp | Ala | Glu | Gly | Arg | Tyr | Arg | Ala | Arg | Ser | Ile |
|---|---|---|---|---|---|---|---|---|---|---|---|---|---|---|---|
| | | | 180 | | | | | 185 | | | | | 190 | | |

| Val | Pro | Ser | Gly | Tyr | Gly | Cys | Asp | Pro | Gln | Gly | Pro | Thr | Gln | Glu | Cys |
|---|---|---|---|---|---|---|---|---|---|---|---|---|---|---|---|
| | | 195 | | | | | 200 | | | | | 205 | | | |

| Leu | Asp | Leu | Leu | Gly | Arg | His | Gly | Gln | Arg | Pro | Ala | His | Val | His | Phe |
|---|---|---|---|---|---|---|---|---|---|---|---|---|---|---|---|
| 210 | | | | | 215 | | | | | 220 | | | | | |

| Phe | Ile | Ser | Ala | Pro | Gly | His | Arg | His | Leu | Thr | Thr | Gln | Ile | Asn | Phe |
|---|---|---|---|---|---|---|---|---|---|---|---|---|---|---|---|
| 225 | | | | | 230 | | | | | 235 | | | | | 240 |

| Ala | Gly | Asp | Lys | Tyr | Leu | Trp | Asp | Asp | Phe | Ala | Tyr | Ala | Thr | Arg | Asp |
|---|---|---|---|---|---|---|---|---|---|---|---|---|---|---|---|
| | | | | 245 | | | | | 250 | | | | | 255 | |

| Gly | Leu | Ile | Gly | Glu | Leu | Arg | Phe | Val | Glu | Asp | Ala | Ala | Ala | Ala | Arg |
|---|---|---|---|---|---|---|---|---|---|---|---|---|---|---|---|
| | | | 260 | | | | | 265 | | | | | 270 | | |

| Asp | Arg | Gly | Val | Gln | Gly | Glu | Arg | Phe | Ala | Glu | Leu | Ser | Phe | Asp | Phe |
|---|---|---|---|---|---|---|---|---|---|---|---|---|---|---|---|
| | | 275 | | | | | 280 | | | | | 285 | | | |

| Arg | Leu | Gln | Gly | Ala | Lys | Ser | Pro | Asp | Ala | Glu | Ala | Arg | Ser | His | Arg |
|---|---|---|---|---|---|---|---|---|---|---|---|---|---|---|---|
| | 290 | | | | | 295 | | | | | 300 | | | | |

| Pro | Arg | Ala | Leu | Gln | Glu | Gly |
|---|---|---|---|---|---|---|
| 305 | | | | 310 | | |

<210> SEQ ID NO 21
<211> LENGTH: 2349
<212> TYPE: DNA
<213> ORGANISM: Methylomicrobium buryatense
<220> FEATURE:
<221> NAME/KEY: CDS
<222> LOCATION: (1)..(2349)

<400> SEQUENCE: 21

```
atg aat aca caa act ctg aat cct gaa ttg ctg agg aaa att gac gcc    48
Met Asn Thr Gln Thr Leu Asn Pro Glu Leu Leu Arg Lys Ile Asp Ala
1               5                   10                  15 tat tgg cgt gca gca aac tat cta tcg gtt ggt cag att tat ctc tat    96
Tyr Trp Arg Ala Ala Asn Tyr Leu Ser Val Gly Gln Ile Tyr Leu Tyr
                20                  25                  30 gac aat ccg ctg ttg aag aag ccg ctc aag cag gcg cac atc aaa ccg    144
Asp Asn Pro Leu Leu Lys Lys Pro Leu Lys Gln Ala His Ile Lys Pro
            35                  40                  45 cgc ctg ctt ggg cac tgg ggc acg acg ccg ggg cta aac ttt gcc tac    192
Arg Leu Leu Gly His Trp Gly Thr Thr Pro Gly Leu Asn Phe Ala Tyr
        50                  55                  60 gtc cac ttg aac cgt gtt atc aag atg cat gat cta aac gta atc tac    240
Val His Leu Asn Arg Val Ile Lys Met His Asp Leu Asn Val Ile Tyr
65                  70                  75                  80 att acc ggg ccg ggg cat ggc gga ccc gcg ctg gtg gcg aat gcc tat    288
Ile Thr Gly Pro Gly His Gly Gly Pro Ala Leu Val Ala Asn Ala Tyr
                85                  90                  95 cta gag ggt acc tac agc gag gtg tat ccc aat atc gcc caa aat gag    336
Leu Glu Gly Thr Tyr Ser Glu Val Tyr Pro Asn Ile Ala Gln Asn Glu
            100                 105                 110 tcg ggg atg aaa cgg ctg ttc aaa cag ttt tcc ttc ccc ggc ggc ata    384
Ser Gly Met Lys Arg Leu Phe Lys Gln Phe Ser Phe Pro Gly Gly Ile
        115                 120                 125 ccg agt cac gtt gca cct gaa aca ccg ggc tcg att cac gag gga ggc    432
Pro Ser His Val Ala Pro Glu Thr Pro Gly Ser Ile His Glu Gly Gly
    130                 135                 140 gag ctg ggt tat tcg ctg tcg cat gcc tac ggg gca gcg ttc gac aat    480
Glu Leu Gly Tyr Ser Leu Ser His Ala Tyr Gly Ala Ala Phe Asp Asn
145                 150                 155                 160 ccc gat ctg atc gtt gct tgt gtc gtc ggc gat ggt gaa gca gag acc    528
Pro Asp Leu Ile Val Ala Cys Val Val Gly Asp Gly Glu Ala Glu Thr
                165                 170                 175 ggt cct ctg gct gcc agt tgg cat tcg aat aaa ttt ctc aat ccg gtc    576
Gly Pro Leu Ala Ala Ser Trp His Ser Asn Lys Phe Leu Asn Pro Val
            180                 185                 190 cac gac ggt gcc gtg ttg ccc atc ctg cat ttg aat ggc tat aaa att    624
His Asp Gly Ala Val Leu Pro Ile Leu His Leu Asn Gly Tyr Lys Ile
        195                 200                 205 gcc ggc ccc acg gtt ttg gcg cgc att ccg cat gac gaa ctg gac gcg    672
Ala Gly Pro Thr Val Leu Ala Arg Ile Pro His Asp Glu Leu Asp Ala
    210                 215                 220 atg ttt cgt ggc ctc ggt tac acg ccg tat ttc gtc gaa ggc gag gat    720
Met Phe Arg Gly Leu Gly Tyr Thr Pro Tyr Phe Val Glu Gly Glu Asp
225                 230                 235                 240 ccg atg gcg atg cat cag ctg atg gcg gct acg ctg gac act gtg gtc    768
Pro Met Ala Met His Gln Leu Met Ala Ala Thr Leu Asp Thr Val Val
                245                 250                 255 ggc gag atc caa cgc atc caa act gaa gcc cgc gcc aac gga ttc aag    816
Gly Glu Ile Gln Arg Ile Gln Thr Glu Ala Arg Ala Asn Gly Phe Lys
            260                 265                 270 aaa cgt ccg aat tgg cct atg atc atc ttg cgc tca ccg aaa ggc tgg    864
Lys Arg Pro Asn Trp Pro Met Ile Ile Leu Arg Ser Pro Lys Gly Trp
        275                 280                 285 acc ggc cct aag gaa gtc gat gac aaa cct acc gag gga aca ttt cga    912
Thr Gly Pro Lys Glu Val Asp Asp Lys Pro Thr Glu Gly Thr Phe Arg
    290                 295                 300 tcg cat cag gtt ccg atg ggc gac atg agt gaa gcg ggg cat gtg aag    960
Ser His Gln Val Pro Met Gly Asp Met Ser Glu Ala Gly His Val Lys
305                 310                 315                 320
```

```
att ctg gaa aag tgg ttg aaa agc tac cat ccg aag caa ttg ttc gac      1008
Ile Leu Glu Lys Trp Leu Lys Ser Tyr His Pro Lys Gln Leu Phe Asp
            325                 330                 335 aag acc ggg aaa ttg gtt gcc gaa ttg gct gaa ttg gcg ccg gcc ggt      1056
Lys Thr Gly Lys Leu Val Ala Glu Leu Ala Glu Leu Ala Pro Ala Gly
        340                 345                 350 gag cgg cgc atg agc gcc aat cca cac gcc aac gga ggg ctc ttg tta      1104
Glu Arg Arg Met Ser Ala Asn Pro His Ala Asn Gly Gly Leu Leu Leu
    355                 360                 365 cag caa ctg cat ctg cct gat ttt cac gac tac gag gtt aag gtg tcc      1152
Gln Gln Leu His Leu Pro Asp Phe His Asp Tyr Glu Val Lys Val Ser
370                 375                 380 aag ccg gga aac gtg gag gcc gaa tcc acc cga gtg caa ggg gaa ttt      1200
Lys Pro Gly Asn Val Glu Ala Glu Ser Thr Arg Val Gln Gly Glu Phe
385                 390                 395                 400 atc cgc gac gtg atc aaa cgg aac cct gaa aac ttc cgt atc ttt agt      1248
Ile Arg Asp Val Ile Lys Arg Asn Pro Glu Asn Phe Arg Ile Phe Ser
                405                 410                 415 ccg gac gaa acg aat tca aac cgc tgg ggc gct gtg ttc gaa gtg acg      1296
Pro Asp Glu Thr Asn Ser Asn Arg Trp Gly Ala Val Phe Glu Val Thr
            420                 425                 430 aac cgt tgt tcg acc gcg gaa att gtg ccc ggc gac gat cat gtt gcc      1344
Asn Arg Cys Ser Thr Ala Glu Ile Val Pro Gly Asp Asp His Val Ala
        435                 440                 445 cct gat ggc cgg gtg atg gag ata ttg agc gag cat cag tgc gag ggt      1392
Pro Asp Gly Arg Val Met Glu Ile Leu Ser Glu His Gln Cys Glu Gly
    450                 455                 460 tgg ctc gaa ggt tac ctg ctg act ggg cgt cac gga ttt ttc tcc tgc      1440
Trp Leu Glu Gly Tyr Leu Leu Thr Gly Arg His Gly Phe Phe Ser Cys
465                 470                 475                 480 tac gaa gcg ttt atc cac atc att gat tcg atg ttc aac cag cat gcc      1488
Tyr Glu Ala Phe Ile His Ile Ile Asp Ser Met Phe Asn Gln His Ala
                485                 490                 495 aaa tgg ctc aag gtc tcg aat cag att cca tgg cgc cgc ccg att gca      1536
Lys Trp Leu Lys Val Ser Asn Gln Ile Pro Trp Arg Arg Pro Ile Ala
            500                 505                 510 tct ttg aac tat ctg ctt tct tcg cac gtc tgg cga cag gat cat aac      1584
Ser Leu Asn Tyr Leu Leu Ser Ser His Val Trp Arg Gln Asp His Asn
        515                 520                 525 ggt ttt agt cat cag gat cca ggc ttc atg gac cat gtc gtg aac aaa      1632
Gly Phe Ser His Gln Asp Pro Gly Phe Met Asp His Val Val Asn Lys
    530                 535                 540 aag gcg gaa gtc att cgt gtc ttt ctg ccg ccc gac gcg aat acg ctg      1680
Lys Ala Glu Val Ile Arg Val Phe Leu Pro Pro Asp Ala Asn Thr Leu
545                 550                 555                 560 ctc tcg gta acg gat cat tgc ctg cgt agc cgc aac tat gtc aac gtt      1728
Leu Ser Val Thr Asp His Cys Leu Arg Ser Arg Asn Tyr Val Asn Val
                565                 570                 575 atc gtt gcc ggc aag caa ccc tct ctg cag tgg tta gac atg gat gag      1776
Ile Val Ala Gly Lys Gln Pro Ser Leu Gln Trp Leu Asp Met Asp Glu
            580                 585                 590 gca att aaa cac tgt acc gct ggt ttg ggt att tgg ccg tgg gcc agc      1824
Ala Ile Lys His Cys Thr Ala Gly Leu Gly Ile Trp Pro Trp Ala Ser
        595                 600                 605 aac gat cag gat ggc gaa ccg gat gtt gtc atg gca tgc tgc ggc gac      1872
Asn Asp Gln Asp Gly Glu Pro Asp Val Val Met Ala Cys Cys Gly Asp
    610                 615                 620 gta ccg acg cta gaa acc ttg gcc gcc gtc gag ttg ttg cgg gaa tat      1920
Val Pro Thr Leu Glu Thr Leu Ala Ala Val Glu Leu Leu Arg Glu Tyr
```

```
                     625                 630                 635                 640
ttc cca gag ctg aag gtt agg gtg att aat gta gtt gat ttg atg aaa          1968
Phe Pro Glu Leu Lys Val Arg Val Ile Asn Val Val Asp Leu Met Lys
                    645                 650                 655 ctc cag acc caa agc gaa cat ccg aat ggt ctg agc gac aaa gat ttc          2016
Leu Gln Thr Gln Ser Glu His Pro Asn Gly Leu Ser Asp Lys Asp Phe
            660                 665                 670 gat tta ctt ttt acc aag gat aag ccg atc atc ttc gcc ttc cac ggt          2064
Asp Leu Leu Phe Thr Lys Asp Lys Pro Ile Ile Phe Ala Phe His Gly
            675                 680                 685 tat cca ttg ctc att cat cgg ttg acc tat cgt cgc agt aac cac tcg          2112
Tyr Pro Leu Leu Ile His Arg Leu Thr Tyr Arg Arg Ser Asn His Ser
        690                 695                 700 aac ctg cat gtg cgc ggt ttc aaa gaa gaa ggc acc acc act acg ccc          2160
Asn Leu His Val Arg Gly Phe Lys Glu Glu Gly Thr Thr Thr Thr Pro
705                 710                 715                 720 ttc gac atg acg gta ttg aac gac ctg gac cgg ttt cat ttg ttt ggc          2208
Phe Asp Met Thr Val Leu Asn Asp Leu Asp Arg Phe His Leu Phe Gly
                725                 730                 735 gat gcc att gac cgc ctc ccg caa ttg gga gct cgg gct gcc tac gcc          2256
Asp Ala Ile Asp Arg Leu Pro Gln Leu Gly Ala Arg Ala Ala Tyr Ala
            740                 745                 750 aag caa gcc atg cga gac aag ctc atc gaa cac aaa caa tac atc agg          2304
Lys Gln Ala Met Arg Asp Lys Leu Ile Glu His Lys Gln Tyr Ile Arg
        755                 760                 765 aag cat ggc gag gat atg ccg gaa att cgt cac tgg aaa tgg aaa              2349
Lys His Gly Glu Asp Met Pro Glu Ile Arg His Trp Lys Trp Lys
        770                 775                 780

<210> SEQ ID NO 22
<211> LENGTH: 783
<212> TYPE: PRT
<213> ORGANISM: Methylomicrobium buryatense

<400> SEQUENCE: 22

Met Asn Thr Gln Thr Leu Asn Pro Glu Leu Leu Arg Lys Ile Asp Ala
1               5                   10                  15

Tyr Trp Arg Ala Ala Asn Tyr Leu Ser Val Gly Gln Ile Tyr Leu Tyr
            20                  25                  30

Asp Asn Pro Leu Leu Lys Lys Pro Leu Lys Gln Ala His Ile Lys Pro
        35                  40                  45

Arg Leu Leu Gly His Trp Gly Thr Thr Pro Gly Leu Asn Phe Ala Tyr
    50                  55                  60

Val His Leu Asn Arg Val Ile Lys Met His Asp Leu Asn Val Ile Tyr
65                  70                  75                  80

Ile Thr Gly Pro Gly His Gly Gly Pro Ala Leu Val Ala Asn Ala Tyr
                85                  90                  95

Leu Glu Gly Thr Tyr Ser Glu Val Tyr Pro Asn Ile Ala Gln Asn Glu
            100                 105                 110

Ser Gly Met Lys Arg Leu Phe Lys Gln Phe Ser Phe Pro Gly Gly Ile
        115                 120                 125

Pro Ser His Val Ala Pro Glu Thr Pro Gly Ser Ile His Glu Gly Gly
    130                 135                 140

Glu Leu Gly Tyr Ser Leu Ser His Ala Tyr Gly Ala Ala Phe Asp Asn
145                 150                 155                 160

Pro Asp Leu Ile Val Ala Cys Val Val Gly Asp Gly Glu Ala Glu Thr
                165                 170                 175
```

```
Gly Pro Leu Ala Ala Ser Trp His Ser Asn Lys Phe Leu Asn Pro Val
            180                 185                 190
His Asp Gly Ala Val Leu Pro Ile Leu His Leu Asn Gly Tyr Lys Ile
        195                 200                 205
Ala Gly Pro Thr Val Leu Ala Arg Ile Pro His Asp Glu Leu Asp Ala
    210                 215                 220
Met Phe Arg Gly Leu Gly Tyr Thr Pro Tyr Phe Val Glu Gly Glu Asp
225                 230                 235                 240
Pro Met Ala Met His Gln Leu Met Ala Ala Thr Leu Asp Thr Val Val
                245                 250                 255
Gly Glu Ile Gln Arg Ile Gln Thr Glu Ala Arg Ala Asn Gly Phe Lys
            260                 265                 270
Lys Arg Pro Asn Trp Pro Met Ile Ile Leu Arg Ser Pro Lys Gly Trp
        275                 280                 285
Thr Gly Pro Lys Glu Val Asp Asp Lys Pro Thr Glu Gly Thr Phe Arg
    290                 295                 300
Ser His Gln Val Pro Met Gly Asp Met Ser Glu Ala Gly His Val Lys
305                 310                 315                 320
Ile Leu Glu Lys Trp Leu Lys Ser Tyr His Pro Lys Gln Leu Phe Asp
                325                 330                 335
Lys Thr Gly Lys Leu Val Ala Glu Leu Ala Glu Leu Ala Pro Ala Gly
            340                 345                 350
Glu Arg Arg Met Ser Ala Asn Pro His Ala Asn Gly Gly Leu Leu Leu
        355                 360                 365
Gln Gln Leu His Leu Pro Asp Phe His Asp Tyr Glu Val Lys Val Ser
    370                 375                 380
Lys Pro Gly Asn Val Glu Ala Glu Ser Thr Arg Val Gln Gly Glu Phe
385                 390                 395                 400
Ile Arg Asp Val Ile Lys Arg Asn Pro Glu Asn Phe Arg Ile Phe Ser
                405                 410                 415
Pro Asp Glu Thr Asn Ser Asn Arg Trp Gly Ala Val Phe Glu Val Thr
            420                 425                 430
Asn Arg Cys Ser Thr Ala Glu Ile Val Pro Gly Asp His Val Ala
        435                 440                 445
Pro Asp Gly Arg Val Met Glu Ile Leu Ser Glu His Gln Cys Glu Gly
    450                 455                 460
Trp Leu Glu Gly Tyr Leu Leu Thr Gly Arg His Gly Phe Phe Ser Cys
465                 470                 475                 480
Tyr Glu Ala Phe Ile His Ile Ile Asp Ser Met Phe Asn Gln His Ala
                485                 490                 495
Lys Trp Leu Lys Val Ser Asn Gln Ile Pro Trp Arg Arg Pro Ile Ala
            500                 505                 510
Ser Leu Asn Tyr Leu Leu Ser Ser His Val Trp Arg Gln Asp His Asn
        515                 520                 525
Gly Phe Ser His Gln Asp Pro Gly Phe Met Asp His Val Val Asn Lys
    530                 535                 540
Lys Ala Glu Val Ile Arg Val Phe Leu Pro Pro Asp Ala Asn Thr Leu
545                 550                 555                 560
Leu Ser Val Thr Asp His Cys Leu Arg Ser Arg Asn Tyr Val Asn Val
                565                 570                 575
Ile Val Ala Gly Lys Gln Pro Ser Leu Gln Trp Leu Asp Met Asp Glu
            580                 585                 590
Ala Ile Lys His Cys Thr Ala Gly Leu Gly Ile Trp Pro Trp Ala Ser
```

```
                    595                 600                 605
            Asn Asp Gln Asp Gly Glu Pro Asp Val Val Met Ala Cys Cys Gly Asp
                610                 615                 620

Val Pro Thr Leu Glu Thr Leu Ala Ala Val Glu Leu Leu Arg Glu Tyr
            625                 630                 635                 640

Phe Pro Glu Leu Lys Val Arg Val Ile Asn Val Val Asp Leu Met Lys
                            645                 650                 655

Leu Gln Thr Gln Ser Glu His Pro Asn Gly Leu Ser Asp Lys Asp Phe
                        660                 665                 670

Asp Leu Leu Phe Thr Lys Asp Lys Pro Ile Ile Phe Ala Phe His Gly
                    675                 680                 685

Tyr Pro Leu Leu Ile His Arg Leu Thr Tyr Arg Arg Ser Asn His Ser
                690                 695                 700

Asn Leu His Val Arg Gly Phe Lys Glu Glu Gly Thr Thr Thr Thr Pro
            705                 710                 715                 720

Phe Asp Met Thr Val Leu Asn Asp Leu Asp Arg Phe His Leu Phe Gly
                            725                 730                 735

Asp Ala Ile Asp Arg Leu Pro Gln Leu Gly Ala Arg Ala Ala Tyr Ala
                        740                 745                 750

Lys Gln Ala Met Arg Asp Lys Leu Ile Glu His Lys Gln Tyr Ile Arg
                    755                 760                 765

Lys His Gly Glu Asp Met Pro Glu Ile Arg His Trp Lys Trp Lys
                770                 775                 780

<210> SEQ ID NO 23
<211> LENGTH: 2388
<212> TYPE: DNA
<213> ORGANISM: Methylomicrobium buryatense
<220> FEATURE:
<221> NAME/KEY: CDS
<222> LOCATION: (1)..(2388)

<400> SEQUENCE: 23 atg agc act gaa att tca aca tcc gtc tcc gac ccc ctc gat gcc gaa        48
Met Ser Thr Glu Ile Ser Thr Ser Val Ser Asp Pro Leu Asp Ala Glu
1               5                   10                  15 gaa tta aga aaa atc gat gct tgg tgg cgc gcc tgc aat tat ttg tcg        96
Glu Leu Arg Lys Ile Asp Ala Trp Trp Arg Ala Cys Asn Tyr Leu Ser
            20                  25                  30 gtc ggc atg att tat ctc cga gct aat cct ctc ctg aaa gaa ccc ttg       144
Val Gly Met Ile Tyr Leu Arg Ala Asn Pro Leu Leu Lys Glu Pro Leu
        35                  40                  45 tcg acc gaa cat gtc aaa cat cgt tta tta ggc cac tgg gga gcc agt       192
Ser Thr Glu His Val Lys His Arg Leu Leu Gly His Trp Gly Ala Ser
    50                  55                  60 ccc gcg ttg tcg ttt gcc tgg gcg cat ctc aat cgt ttg att aaa cgt       240
Pro Ala Leu Ser Phe Ala Trp Ala His Leu Asn Arg Leu Ile Lys Arg
65                  70                  75                  80 gac gag ctc gat gtg att ttt atc gcc ggt ccc ggt cat gga gcc ccc       288
Asp Glu Leu Asp Val Ile Phe Ile Ala Gly Pro Gly His Gly Ala Pro
                85                  90                  95 ggc gtt tta ggg ccg agt tac ttg gaa ggc acc tat tcc gaa gtc tat       336
Gly Val Leu Gly Pro Ser Tyr Leu Glu Gly Thr Tyr Ser Glu Val Tyr
            100                 105                 110 ccc gat aaa agc gaa gac acg gaa ggc atg cgt aaa ttc ttc aaa caa       384
Pro Asp Lys Ser Glu Asp Thr Glu Gly Met Arg Lys Phe Phe Lys Gln
        115                 120                 125 ttt tca ttc ccg ggc cag atc ggc tcg cat gtc acg ccg gaa acg ccc       432
```

|  |  |  |  |  |  |  |  |  |  |  |  |  |
|---|---|---|---|---|---|---|---|---|---|---|---|---|
| Phe | Ser | Phe | Pro | Gly | Gln | Ile | Gly | Ser | His | Val | Thr | Pro | Glu | Thr | Pro |
|  | 130 |  |  |  | 135 |  |  |  | 140 |  |  |  |

```
ggt tcg atc cat gaa ggc ggc gaa ttg ggc tac agt ctc gca cat gcc       480
Gly Ser Ile His Glu Gly Gly Glu Leu Gly Tyr Ser Leu Ala His Ala
145             150                 155                 160 tac ggc gca gca ttc gac aat ccg gat ttg atc gtc gcc tgt gtg gtc       528
Tyr Gly Ala Ala Phe Asp Asn Pro Asp Leu Ile Val Ala Cys Val Val
                165                 170                 175 gga gac ggc gag gcg gaa aca ggg cca ttg gcg act gct tgg cat tcg       576
Gly Asp Gly Glu Ala Glu Thr Gly Pro Leu Ala Thr Ala Trp His Ser
            180                 185                 190 aat aaa ttc ttg aat ccg ata cgc gac ggc gcg gtc ttg ccc att ctc       624
Asn Lys Phe Leu Asn Pro Ile Arg Asp Gly Ala Val Leu Pro Ile Leu
        195                 200                 205 aat ctg aat ggc tac aaa atc gcc aat ccg aca att ctt gcc cgc atc       672
Asn Leu Asn Gly Tyr Lys Ile Ala Asn Pro Thr Ile Leu Ala Arg Ile
    210                 215                 220 agt cac gaa gaa ctg gag gcc atg ttt atc ggt tat ggt tac cgg ccc       720
Ser His Glu Glu Leu Glu Ala Met Phe Ile Gly Tyr Gly Tyr Arg Pro
225                 230                 235                 240 tat ttc gtc gaa ggc agc gat ccg gca gaa atg cat caa aaa atg gct       768
Tyr Phe Val Glu Gly Ser Asp Pro Ala Glu Met His Gln Lys Met Ala
                245                 250                 255 tcc gtt gtt gat gaa gcc atc gcc gaa atc aaa acc att caa aag tcc       816
Ser Val Val Asp Glu Ala Ile Ala Glu Ile Lys Thr Ile Gln Lys Ser
            260                 265                 270 gcc cga gaa agc gga atc gca gag cgc ccg cgc tgg ccg atg atc gtg       864
Ala Arg Glu Ser Gly Ile Ala Glu Arg Pro Arg Trp Pro Met Ile Val
        275                 280                 285 tta cgg tct ccg aaa ggc tgg acc gga ccg aaa aca atc aac ggc cat       912
Leu Arg Ser Pro Lys Gly Trp Thr Gly Pro Lys Thr Ile Asn Gly His
    290                 295                 300 caa tcc gaa ggc tcg tgg cga tct cat caa gtg ccc ttt gcc gac gct       960
Gln Ser Glu Gly Ser Trp Arg Ser His Gln Val Pro Phe Ala Asp Ala
305                 310                 315                 320 ggc acc agt tcg tcc ggc ttg cgc tta ctg gag gaa tgg ctg caa agc      1008
Gly Thr Ser Ser Ser Gly Leu Arg Leu Leu Glu Glu Trp Leu Gln Ser
                325                 330                 335 tat cga ccg gaa gag cta ttc gac gac aac ggc cgc tta gtg gca gaa      1056
Tyr Arg Pro Glu Glu Leu Phe Asp Asp Asn Gly Arg Leu Val Ala Glu
            340                 345                 350 ctc aga gaa ctt tct cca caa ggc cag cgc cga atg agc gcc aat ctt      1104
Leu Arg Glu Leu Ser Pro Gln Gly Gln Arg Arg Met Ser Ala Asn Leu
        355                 360                 365 cac gcc aac ggc ggc tta ttg cgc aag gcg ctc aaa tta ccc gat ttt      1152
His Ala Asn Gly Gly Leu Leu Arg Lys Ala Leu Lys Leu Pro Asp Phe
    370                 375                 380 cga gac tat gcg gtc gaa gtc aac cgg ctc ggc caa gcc gaa cat gaa      1200
Arg Asp Tyr Ala Val Glu Val Asn Arg Leu Gly Gln Ala Glu His Glu
385                 390                 395                 400 aac acc aag ccg ctg ggc gaa ttc tta agg gac gtt cta aaa aac aac      1248
Asn Thr Lys Pro Leu Gly Glu Phe Leu Arg Asp Val Leu Lys Asn Asn
                405                 410                 415 atg aac aat ttc cgg att ttc ggt ccg gac gaa acc gca tcg aac cgc      1296
Met Asn Asn Phe Arg Ile Phe Gly Pro Asp Glu Thr Ala Ser Asn Arg
            420                 425                 430 ttg caa gcg gtc tat gga gcg tcc aaa aag act tgg atg gcg gat ttt      1344
Leu Gln Ala Val Tyr Gly Ala Ser Lys Lys Thr Trp Met Ala Asp Phe
        435                 440                 445
```

```
                                                         -continued tta ccc gaa gac gaa gac ggc ggc gaa ttg agc cgg gac ggg cgc gtc    1392
Leu Pro Glu Asp Glu Asp Gly Gly Glu Leu Ser Arg Asp Gly Arg Val
    450                 455                 460 atg gaa atg ctc tcc gaa cat acc ctg gtc ggc tgg ctt gaa ggc tac    1440
Met Glu Met Leu Ser Glu His Thr Leu Val Gly Trp Leu Glu Gly Tyr
465                 470                 475                 480 ttg ctg acc ggc cgg cac ggt ttt ttc cat acc tac gaa gcc ttc gcc    1488
Leu Leu Thr Gly Arg His Gly Phe Phe His Thr Tyr Glu Ala Phe Ala
            485                 490                 495 cac gtc gtc gat tcg atg ttc aac caa cat gca aaa tgg ctc gac acc    1536
His Val Val Asp Ser Met Phe Asn Gln His Ala Lys Trp Leu Asp Thr
        500                 505                 510 agt aaa aac cat gtg cca tgg cga gcg aaa gta tct tcg caa aat atc    1584
Ser Lys Asn His Val Pro Trp Arg Ala Lys Val Ser Ser Gln Asn Ile
    515                 520                 525 ttg ttg tcc tcg acc gtc tgg cgt cag gat cat aac ggc ttc tcg cac    1632
Leu Leu Ser Ser Thr Val Trp Arg Gln Asp His Asn Gly Phe Ser His
530                 535                 540 caa gac ccc ggc ttt atc gat ctg gtc acg aac aaa agc cca tcg gtg    1680
Gln Asp Pro Gly Phe Ile Asp Leu Val Thr Asn Lys Ser Pro Ser Val
545                 550                 555                 560 acc cgc gtc tat ttg ccg ccc gat gcg aac acc ctg ctt tcg gtt gcc    1728
Thr Arg Val Tyr Leu Pro Pro Asp Ala Asn Thr Leu Leu Ser Val Ala
            565                 570                 575 gat cat tgc ctg cgt tcg acc gac tat atc aac gtc ata gtc gcg gac    1776
Asp His Cys Leu Arg Ser Thr Asp Tyr Ile Asn Val Ile Val Ala Asp
        580                 585                 590 aag caa aag cat ctt cag ttt ttg acg atc gaa gaa gcg att gtg cac    1824
Lys Gln Lys His Leu Gln Phe Leu Thr Ile Glu Glu Ala Ile Val His
    595                 600                 605 tgc acc aag ggt gtc gga ctt tgg gaa cgc gcc agt aac gac caa ggt    1872
Cys Thr Lys Gly Val Gly Leu Trp Glu Arg Ala Ser Asn Asp Gln Gly
610                 615                 620 caa gac ccg gac gta gtc atg gct tgc tgc ggc gat gtc gca acc ttg    1920
Gln Asp Pro Asp Val Val Met Ala Cys Cys Gly Asp Val Ala Thr Leu
625                 630                 635                 640 gaa gcg ctg gcc gca acg gcc att ctg cgt gag cat cta ccg gat ttg    1968
Glu Ala Leu Ala Ala Thr Ala Ile Leu Arg Glu His Leu Pro Asp Leu
            645                 650                 655 aaa gtc cgt ttt gtc aat gtg gtc gat tta ttc aaa ctg caa ccg aac    2016
Lys Val Arg Phe Val Asn Val Val Asp Leu Phe Lys Leu Gln Pro Asn
        660                 665                 670 acc gaa cat cct cac ggt tta agt cat cgc gaa ttc gat agc cta ttt    2064
Thr Glu His Pro His Gly Leu Ser His Arg Glu Phe Asp Ser Leu Phe
    675                 680                 685 acg gtc gac aaa ccg gtc att ttc aat ttc cac ggc tat ccc tgg ttg    2112
Thr Val Asp Lys Pro Val Ile Phe Asn Phe His Gly Tyr Pro Trp Leu
690                 695                 700 att cac aaa ttg gcc tat cgc ttc aag aat cat gaa aat ctg cat gtg    2160
Ile His Lys Leu Ala Tyr Arg Phe Lys Asn His Glu Asn Leu His Val
705                 710                 715                 720 cgg ggc tat aaa gaa cgc ggc aat atc aat aca ccc atg gag ctt gcg    2208
Arg Gly Tyr Lys Glu Arg Gly Asn Ile Asn Thr Pro Met Glu Leu Ala
            725                 730                 735 att ctg aac gaa gtc gat cgc ttc aat cta gtc atc gat gtc atc gac    2256
Ile Leu Asn Glu Val Asp Arg Phe Asn Leu Val Ile Asp Val Ile Asp
        740                 745                 750 cgg gtt ccg aaa ttg caa atc agg gcg gcc cat ctc aag gag ctc atg    2304
Arg Val Pro Lys Leu Gln Ile Arg Ala Ala His Leu Lys Glu Leu Met
    755                 760                 765
```

```
aaa aac gaa atc atc gag aat ctt cgt tat gcg cat caa cac ggc acc        2352
Lys Asn Glu Ile Ile Glu Asn Leu Arg Tyr Ala His Gln His Gly Thr
770                 775                 780 gat aaa ccc gaa atc acc ggt tgg caa tgg ccg ttt                        2388
Asp Lys Pro Glu Ile Thr Gly Trp Gln Trp Pro Phe
785                 790                 795

<210> SEQ ID NO 24
<211> LENGTH: 796
<212> TYPE: PRT
<213> ORGANISM: Methylomicrobium buryatense

<400> SEQUENCE: 24

Met Ser Thr Glu Ile Ser Thr Ser Val Ser Asp Pro Leu Asp Ala Glu
1               5                   10                  15

Glu Leu Arg Lys Ile Asp Ala Trp Trp Arg Ala Cys Asn Tyr Leu Ser
            20                  25                  30

Val Gly Met Ile Tyr Leu Arg Ala Asn Pro Leu Leu Lys Glu Pro Leu
        35                  40                  45

Ser Thr Glu His Val Lys His Arg Leu Leu Gly His Trp Gly Ala Ser
    50                  55                  60

Pro Ala Leu Ser Phe Ala Trp Ala His Leu Asn Arg Leu Ile Lys Arg
65                  70                  75                  80

Asp Glu Leu Asp Val Ile Phe Ile Ala Gly Pro Gly His Gly Ala Pro
                85                  90                  95

Gly Val Leu Gly Pro Ser Tyr Leu Glu Gly Thr Tyr Ser Glu Val Tyr
            100                 105                 110

Pro Asp Lys Ser Glu Asp Thr Glu Gly Met Arg Lys Phe Phe Lys Gln
        115                 120                 125

Phe Ser Phe Pro Gly Gln Ile Gly Ser His Val Thr Pro Glu Thr Pro
    130                 135                 140

Gly Ser Ile His Glu Gly Gly Glu Leu Gly Tyr Ser Leu Ala His Ala
145                 150                 155                 160

Tyr Gly Ala Ala Phe Asp Asn Pro Asp Leu Ile Val Ala Cys Val Val
                165                 170                 175

Gly Asp Gly Glu Ala Glu Thr Gly Pro Leu Ala Thr Ala Trp His Ser
            180                 185                 190

Asn Lys Phe Leu Asn Pro Ile Arg Asp Gly Ala Val Leu Pro Ile Leu
        195                 200                 205

Asn Leu Asn Gly Tyr Lys Ile Ala Asn Pro Thr Ile Leu Ala Arg Ile
    210                 215                 220

Ser His Glu Glu Leu Glu Ala Met Phe Ile Gly Tyr Gly Tyr Arg Pro
225                 230                 235                 240

Tyr Phe Val Glu Gly Ser Asp Pro Ala Glu Met His Gln Lys Met Ala
                245                 250                 255

Ser Val Val Asp Glu Ala Ile Ala Glu Ile Lys Thr Ile Gln Lys Ser
            260                 265                 270

Ala Arg Glu Ser Gly Ile Ala Glu Arg Pro Arg Trp Pro Met Ile Val
        275                 280                 285

Leu Arg Ser Pro Lys Gly Trp Thr Gly Pro Lys Thr Ile Asn Gly His
    290                 295                 300

Gln Ser Glu Gly Ser Trp Arg Ser His Gln Val Pro Phe Ala Asp Ala
305                 310                 315                 320

Gly Thr Ser Ser Ser Gly Leu Arg Leu Leu Glu Glu Trp Leu Gln Ser
                325                 330                 335
```

```
Tyr Arg Pro Glu Glu Leu Phe Asp Asp Asn Gly Arg Leu Val Ala Glu
            340                 345                 350

Leu Arg Glu Leu Ser Pro Gln Gly Gln Arg Arg Met Ser Ala Asn Leu
            355                 360                 365

His Ala Asn Gly Gly Leu Leu Arg Lys Ala Leu Lys Leu Pro Asp Phe
            370                 375                 380

Arg Asp Tyr Ala Val Glu Val Asn Arg Leu Gly Gln Ala Glu His Glu
385                 390                 395                 400

Asn Thr Lys Pro Leu Gly Glu Phe Leu Arg Asp Val Leu Lys Asn Asn
                405                 410                 415

Met Asn Asn Phe Arg Ile Phe Gly Pro Asp Thr Ala Ser Asn Arg
            420                 425                 430

Leu Gln Ala Val Tyr Gly Ala Ser Lys Lys Thr Trp Met Ala Asp Phe
            435                 440                 445

Leu Pro Glu Asp Glu Gly Gly Glu Leu Ser Arg Asp Gly Arg Val
    450                 455                 460

Met Glu Met Leu Ser Glu His Thr Leu Val Gly Trp Leu Glu Gly Tyr
465                 470                 475                 480

Leu Leu Thr Gly Arg His Gly Phe Phe His Thr Tyr Glu Ala Phe Ala
                485                 490                 495

His Val Val Asp Ser Met Phe Asn Gln His Ala Lys Trp Leu Asp Thr
                500                 505                 510

Ser Lys Asn His Val Pro Trp Arg Ala Lys Val Ser Ser Gln Asn Ile
            515                 520                 525

Leu Leu Ser Ser Thr Val Trp Arg Gln Asp His Asn Gly Phe Ser His
            530                 535                 540

Gln Asp Pro Gly Phe Ile Asp Leu Val Thr Asn Lys Ser Pro Ser Val
545                 550                 555                 560

Thr Arg Val Tyr Leu Pro Pro Asp Ala Asn Thr Leu Leu Ser Val Ala
                565                 570                 575

Asp His Cys Leu Arg Ser Thr Asp Tyr Ile Asn Val Ile Val Ala Asp
            580                 585                 590

Lys Gln Lys His Leu Gln Phe Leu Thr Ile Glu Glu Ala Ile Val His
            595                 600                 605

Cys Thr Lys Gly Val Gly Leu Trp Glu Arg Ala Ser Asn Asp Gln Gly
            610                 615                 620

Gln Asp Pro Asp Val Val Met Ala Cys Cys Gly Asp Val Ala Thr Leu
625                 630                 635                 640

Glu Ala Leu Ala Ala Thr Ala Ile Leu Arg Glu His Leu Pro Asp Leu
                645                 650                 655

Lys Val Arg Phe Val Asn Val Val Asp Leu Phe Lys Leu Gln Pro Asn
            660                 665                 670

Thr Glu His Pro His Gly Leu Ser His Arg Glu Phe Asp Ser Leu Phe
            675                 680                 685

Thr Val Asp Lys Pro Val Ile Phe Asn Phe His Gly Tyr Pro Trp Leu
            690                 695                 700

Ile His Lys Leu Ala Tyr Arg Phe Lys Asn His Glu Asn Leu His Val
705                 710                 715                 720

Arg Gly Tyr Lys Glu Arg Gly Asn Ile Asn Thr Pro Met Glu Leu Ala
                725                 730                 735

Ile Leu Asn Glu Val Asp Arg Phe Asn Leu Val Ile Asp Val Ile Asp
                740                 745                 750
```

```
Arg Val Pro Lys Leu Gln Ile Arg Ala Ala His Leu Lys Glu Leu Met
        755                 760                 765

Lys Asn Glu Ile Ile Glu Asn Leu Arg Tyr Ala His Gln His Gly Thr
    770                 775                 780

Asp Lys Pro Glu Ile Thr Gly Trp Gln Trp Pro Phe
785                 790                 795

<210> SEQ ID NO 25
<211> LENGTH: 1419
<212> TYPE: DNA
<213> ORGANISM: Methylococcus capsulatus
<220> FEATURE:
<221> NAME/KEY: CDS
<222> LOCATION: (1)..(1419)

<400> SEQUENCE: 25 atg gct gtc aaa aca tac aac gcg ggc gtc aag gaa tac cgc gaa acc        48
Met Ala Val Lys Thr Tyr Asn Ala Gly Val Lys Glu Tyr Arg Glu Thr
1               5                   10                  15 tac tgg gac ccg aac tac act ccc gcc gac acc gat ctg ctg gcg gtc        96
Tyr Trp Asp Pro Asn Tyr Thr Pro Ala Asp Thr Asp Leu Leu Ala Val
                20                  25                  30 ttc aag atc acc cct cag ccg ggt gtg ccg cgc gaa gaa gcc gcc gcc       144
Phe Lys Ile Thr Pro Gln Pro Gly Val Pro Arg Glu Glu Ala Ala Ala
            35                  40                  45 gcc gtg gcc gcg gaa tcg tcg acc ggc acc tgg acc acc gtc tgg acc       192
Ala Val Ala Ala Glu Ser Ser Thr Gly Thr Trp Thr Thr Val Trp Thr
        50                  55                  60 gac ctg ctg acc gac ctc gac tat tac aag ggc cgc gcc tac cgg atc       240
Asp Leu Leu Thr Asp Leu Asp Tyr Tyr Lys Gly Arg Ala Tyr Arg Ile
65                  70                  75                  80 gag gac gtg ccc ggc cag gac gaa cag ttc tac gcc ttc atc gcc tat       288
Glu Asp Val Pro Gly Gln Asp Glu Gln Phe Tyr Ala Phe Ile Ala Tyr
                85                  90                  95 ccc atc gac ctg ttc gag gag ggc tcc gtc gtc aac gtg ttc acc tcg       336
Pro Ile Asp Leu Phe Glu Glu Gly Ser Val Val Asn Val Phe Thr Ser
            100                 105                 110 ctg gtg ggc aac gtg ttc ggc ttc aag gcc gtg cgc ggc ctg cgc ctg       384
Leu Val Gly Asn Val Phe Gly Phe Lys Ala Val Arg Gly Leu Arg Leu
        115                 120                 125 gaa gac gtg cgc ttc ccc ctc gcc tac gtg atg acc tgc ggc ggc ccg       432
Glu Asp Val Arg Phe Pro Leu Ala Tyr Val Met Thr Cys Gly Gly Pro
    130                 135                 140 ccc cac ggc atc cag gtg gag cgc gac atc atg aac aag tac ggc cgt       480
Pro His Gly Ile Gln Val Glu Arg Asp Ile Met Asn Lys Tyr Gly Arg
145                 150                 155                 160 ccg ttg ctc ggc tgc acc atc aag ccc aag ctg ggc ctg tcg gcc aag       528
Pro Leu Leu Gly Cys Thr Ile Lys Pro Lys Leu Gly Leu Ser Ala Lys
                165                 170                 175 aac tac ggc cgc gcc gtg tac gag tgc ctc aga ggc ggc ctg gac ttc       576
Asn Tyr Gly Arg Ala Val Tyr Glu Cys Leu Arg Gly Gly Leu Asp Phe
            180                 185                 190 acc aag gac gac gag aac gtc aac agc cag ccg ttc atg cgc tgg cgc       624
Thr Lys Asp Asp Glu Asn Val Asn Ser Gln Pro Phe Met Arg Trp Arg
        195                 200                 205 cag cgc ttc gac ttc gtg atg gag gcg atc gag aag gcc gag gcc gaa       672
Gln Arg Phe Asp Phe Val Met Glu Ala Ile Glu Lys Ala Glu Ala Glu
    210                 215                 220 acc ggc gag cgc aag ggc cac tac ctc aac gtg acc gcc ccg act ccg       720
Thr Gly Glu Arg Lys Gly His Tyr Leu Asn Val Thr Ala Pro Thr Pro
225                 230                 235                 240
```

```
gaa gag atg tac aaa cgt gcc gag tac gcc aag gaa atc ggc gcg ccc        768
Glu Glu Met Tyr Lys Arg Ala Glu Tyr Ala Lys Glu Ile Gly Ala Pro
            245                 250                 255 atc atc atg cac gac ttc atc acc ggg ggc ttc tgc gcc aac acg ggt        816
Ile Ile Met His Asp Phe Ile Thr Gly Gly Phe Cys Ala Asn Thr Gly
        260                 265                 270 ctc gcc aac tgg tgc cgc aac aac ggc atg ctg ctg cac atc cac cgc        864
Leu Ala Asn Trp Cys Arg Asn Asn Gly Met Leu Leu His Ile His Arg
        275                 280                 285 gcc atg cac gcc gtg atg gac cgc aat ccc aac cac ggc atc cac ttc        912
Ala Met His Ala Val Met Asp Arg Asn Pro Asn His Gly Ile His Phe
        290                 295                 300 cgc gtc ttc acc aag atg ctg cgc ctt tct ggc ggc gac cat ctg cac        960
Arg Val Phe Thr Lys Met Leu Arg Leu Ser Gly Gly Asp His Leu His
305                 310                 315                 320 acc ggc acc gtg gtc ggc aag ctg gaa ggc gac cgc cag gcc acc ctg       1008
Thr Gly Thr Val Val Gly Lys Leu Glu Gly Asp Arg Gln Ala Thr Leu
                325                 330                 335 ggg tgg atc gac ctg ctg cgc gaa cgc agc atc aag gaa gac cgc agc       1056
Gly Trp Ile Asp Leu Leu Arg Glu Arg Ser Ile Lys Glu Asp Arg Ser
            340                 345                 350 cgc ggc atc ttc ttc gac cag gaa tgg ggc gcc atg ccc ggc gtg ttc       1104
Arg Gly Ile Phe Phe Asp Gln Glu Trp Gly Ala Met Pro Gly Val Phe
        355                 360                 365 gcg gtc gcc tcc ggc ggc atc cac gtc tgg cac atg ccg gca ctg ctt       1152
Ala Val Ala Ser Gly Gly Ile His Val Trp His Met Pro Ala Leu Leu
        370                 375                 380 tcg atc ttc ggc gac gac gcg gtg ttc cag ttc ggt ggc ggc acc ctg       1200
Ser Ile Phe Gly Asp Asp Ala Val Phe Gln Phe Gly Gly Gly Thr Leu
385                 390                 395                 400 ggc cat cct tgg ggc aac gcg gcc ggc gcc gct gcc aac cgc gtg gcg       1248
Gly His Pro Trp Gly Asn Ala Ala Gly Ala Ala Ala Asn Arg Val Ala
                405                 410                 415 ctg gaa gcc tgc gtg gag gcc cgc aac gaa ggc cgc cag ctc gag aag       1296
Leu Glu Ala Cys Val Glu Ala Arg Asn Glu Gly Arg Gln Leu Glu Lys
            420                 425                 430 gaa ggc aag gaa atc ctg acc gaa gcc gcc aag agc agc ccg gaa ctc       1344
Glu Gly Lys Glu Ile Leu Thr Glu Ala Ala Lys Ser Ser Pro Glu Leu
        435                 440                 445 aag gcc gca atg gag acc tgg aag gaa atc aaa ttc gag ttc gac acc       1392
Lys Ala Ala Met Glu Thr Trp Lys Glu Ile Lys Phe Glu Phe Asp Thr
        450                 455                 460 gtc gac aag ctc gac gtg gcc cac cgg                                   1419
Val Asp Lys Leu Asp Val Ala His Arg
465                 470

<210> SEQ ID NO 26
<211> LENGTH: 473
<212> TYPE: PRT
<213> ORGANISM: Methylococcus capsulatus

<400> SEQUENCE: 26

Met Ala Val Lys Thr Tyr Asn Ala Gly Val Lys Glu Tyr Arg Glu Thr
1               5                   10                  15

Tyr Trp Asp Pro Asn Tyr Thr Pro Ala Asp Thr Asp Leu Leu Ala Val
            20                  25                  30

Phe Lys Ile Thr Pro Gln Pro Gly Val Pro Arg Glu Glu Ala Ala Ala
        35                  40                  45

Ala Val Ala Ala Glu Ser Ser Thr Gly Thr Trp Thr Thr Val Trp Thr
```

```
                50                  55                  60
Asp Leu Leu Thr Asp Leu Asp Tyr Tyr Lys Gly Arg Ala Tyr Arg Ile
 65                  70                  75                  80

Glu Asp Val Pro Gly Gln Asp Glu Gln Phe Tyr Ala Phe Ile Ala Tyr
                 85                  90                  95

Pro Ile Asp Leu Phe Glu Glu Gly Ser Val Val Asn Val Phe Thr Ser
                100                 105                 110

Leu Val Gly Asn Val Phe Gly Phe Lys Ala Val Arg Gly Leu Arg Leu
                115                 120                 125

Glu Asp Val Arg Phe Pro Leu Ala Tyr Val Met Thr Cys Gly Gly Pro
130                 135                 140

Pro His Gly Ile Gln Val Glu Arg Asp Ile Met Asn Lys Tyr Gly Arg
145                 150                 155                 160

Pro Leu Leu Gly Cys Thr Ile Lys Pro Lys Leu Gly Leu Ser Ala Lys
                165                 170                 175

Asn Tyr Gly Arg Ala Val Tyr Glu Cys Leu Arg Gly Gly Leu Asp Phe
                180                 185                 190

Thr Lys Asp Asp Glu Asn Val Asn Ser Gln Pro Phe Met Arg Trp Arg
                195                 200                 205

Gln Arg Phe Asp Phe Val Met Glu Ala Ile Glu Lys Ala Glu Ala Glu
210                 215                 220

Thr Gly Glu Arg Lys Gly His Tyr Leu Asn Val Thr Ala Pro Thr Pro
225                 230                 235                 240

Glu Glu Met Tyr Lys Arg Ala Glu Tyr Ala Lys Glu Ile Gly Ala Pro
                245                 250                 255

Ile Ile Met His Asp Phe Ile Thr Gly Gly Phe Cys Ala Asn Thr Gly
                260                 265                 270

Leu Ala Asn Trp Cys Arg Asn Asn Gly Met Leu Leu His Ile His Arg
                275                 280                 285

Ala Met His Ala Val Met Asp Arg Asn Pro Asn His Gly Ile His Phe
290                 295                 300

Arg Val Phe Thr Lys Met Leu Arg Leu Ser Gly Gly Asp His Leu His
305                 310                 315                 320

Thr Gly Thr Val Val Gly Lys Leu Glu Gly Asp Arg Gln Ala Thr Leu
                325                 330                 335

Gly Trp Ile Asp Leu Leu Arg Glu Arg Ser Ile Lys Glu Asp Arg Ser
                340                 345                 350

Arg Gly Ile Phe Phe Asp Gln Glu Trp Gly Ala Met Pro Gly Val Phe
                355                 360                 365

Ala Val Ala Ser Gly Gly Ile His Val Trp His Met Pro Ala Leu Leu
370                 375                 380

Ser Ile Phe Gly Asp Asp Ala Val Phe Gln Phe Gly Gly Gly Thr Leu
385                 390                 395                 400

Gly His Pro Trp Gly Asn Ala Ala Gly Ala Ala Ala Asn Arg Val Ala
                405                 410                 415

Leu Glu Ala Cys Val Glu Ala Arg Asn Glu Gly Arg Gln Leu Glu Lys
                420                 425                 430

Glu Gly Lys Glu Ile Leu Thr Glu Ala Ala Lys Ser Ser Pro Glu Leu
                435                 440                 445

Lys Ala Ala Met Glu Thr Trp Lys Glu Ile Lys Phe Glu Phe Asp Thr
450                 455                 460

Val Asp Lys Leu Asp Val Ala His Arg
465                 470
```

<210> SEQ ID NO 27
<211> LENGTH: 354
<212> TYPE: DNA
<213> ORGANISM: Methylococcus capsulatus
<220> FEATURE:
<221> NAME/KEY: CDS
<222> LOCATION: (1)..(354)

<400> SEQUENCE: 27

| | | | | | | | | | | | | | | | | |
|---|---|---|---|---|---|---|---|---|---|---|---|---|---|---|---|---|
| atg | agc | gat | atg | caa | gac | tac | aaa | tcc | agc | ctg | tcc | gac | agc | ggc | tcg | 48 |
| Met | Ser | Asp | Met | Gln | Asp | Tyr | Lys | Ser | Ser | Leu | Ser | Asp | Ser | Gly | Ser | |
| 1 | | | | 5 | | | | | 10 | | | | | 15 | | |
| cgc | aag | ttc | gag | act | ttc | tcc | tac | ctg | ccg | ccg | atg | aac | ccg | gag | aag | 96 |
| Arg | Lys | Phe | Glu | Thr | Phe | Ser | Tyr | Leu | Pro | Pro | Met | Asn | Pro | Glu | Lys | |
| | | | 20 | | | | | 25 | | | | | 30 | | | |
| atc | cgc | cgg | cag | gtg | gaa | tac | atc | gtc | agc | cgc | ggc | tgg | aat | ccg | gcc | 144 |
| Ile | Arg | Arg | Gln | Val | Glu | Tyr | Ile | Val | Ser | Arg | Gly | Trp | Asn | Pro | Ala | |
| | | 35 | | | | | 40 | | | | | 45 | | | | |
| atc | gaa | cat | acc | gag | ccg | gaa | aac | gcc | ttc | gac | cac | tac | tgg | tac | atg | 192 |
| Ile | Glu | His | Thr | Glu | Pro | Glu | Asn | Ala | Phe | Asp | His | Tyr | Trp | Tyr | Met | |
| | 50 | | | | | 55 | | | | | 60 | | | | | |
| tgg | aaa | ctg | ccg | atg | ttc | ggc | gag | acc | gac | gtc | gat | gcg | atc | ctg | gcc | 240 |
| Trp | Lys | Leu | Pro | Met | Phe | Gly | Glu | Thr | Asp | Val | Asp | Ala | Ile | Leu | Ala | |
| 65 | | | | | 70 | | | | | 75 | | | | | 80 | |
| gag | gcc | gag | gcc | tgc | cac | aag | gcg | cac | ccc | aac | aac | cac | gtc | cga | ctg | 288 |
| Glu | Ala | Glu | Ala | Cys | His | Lys | Ala | His | Pro | Asn | Asn | His | Val | Arg | Leu | |
| | | | | 85 | | | | | 90 | | | | | 95 | | |
| gtc | ggc | tac | gac | aac | ttc | agg | cag | acc | cag | ggc | gcc | gcc | atg | gtg | atc | 336 |
| Val | Gly | Tyr | Asp | Asn | Phe | Arg | Gln | Thr | Gln | Gly | Ala | Ala | Met | Val | Ile | |
| | | | 100 | | | | | 105 | | | | | 110 | | | |
| tat | cgg | ggg | ccg | tcg | gtc | | | | | | | | | | | 354 |
| Tyr | Arg | Gly | Pro | Ser | Val | | | | | | | | | | | |
| | | | 115 | | | | | | | | | | | | | |

<210> SEQ ID NO 28
<211> LENGTH: 118
<212> TYPE: PRT
<213> ORGANISM: Methylococcus capsulatus

<400> SEQUENCE: 28

Met Ser Asp Met Gln Asp Tyr Lys Ser Ser Leu Ser Asp Ser Gly Ser
1               5                   10                  15

Arg Lys Phe Glu Thr Phe Ser Tyr Leu Pro Pro Met Asn Pro Glu Lys
            20                  25                  30

Ile Arg Arg Gln Val Glu Tyr Ile Val Ser Arg Gly Trp Asn Pro Ala
        35                  40                  45

Ile Glu His Thr Glu Pro Glu Asn Ala Phe Asp His Tyr Trp Tyr Met
    50                  55                  60

Trp Lys Leu Pro Met Phe Gly Glu Thr Asp Val Asp Ala Ile Leu Ala
65                  70                  75                  80

Glu Ala Glu Ala Cys His Lys Ala His Pro Asn Asn His Val Arg Leu
                85                  90                  95

Val Gly Tyr Asp Asn Phe Arg Gln Thr Gln Gly Ala Ala Met Val Ile
            100                 105                 110

Tyr Arg Gly Pro Ser Val
        115

<210> SEQ ID NO 29
<211> LENGTH: 798

```
<212> TYPE: DNA
<213> ORGANISM: Methylococcus capsulatus
<220> FEATURE:
<221> NAME/KEY: CDS
<222> LOCATION: (1)..(798)

<400> SEQUENCE: 29 atg tcc agc aca gag caa tac ctg att caa gaa cga ccc tat tac cgc      48
Met Ser Ser Thr Glu Gln Tyr Leu Ile Gln Glu Arg Pro Tyr Tyr Arg
1               5                   10                  15 gcc acc gcc gac gaa gtc gag ctg ttc gag gcc gcc tat gcc gcg cgc      96
Ala Thr Ala Asp Glu Val Glu Leu Phe Glu Ala Ala Tyr Ala Ala Arg
                20                  25                  30 atg ccg gtg atg ctc aag ggc ccg acc ggc tgc ggc aag acc cgg ttc     144
Met Pro Val Met Leu Lys Gly Pro Thr Gly Cys Gly Lys Thr Arg Phe
            35                  40                  45 gtg gaa tac atg gcc tgg aag ctg aag cgc ccg ctg atc acg gtg gcc     192
Val Glu Tyr Met Ala Trp Lys Leu Lys Arg Pro Leu Ile Thr Val Ala
        50                  55                  60 tgc aac gaa gac atg acg gcc tcg gac ctg gtc ggc cgc ttc ctg ctc     240
Cys Asn Glu Asp Met Thr Ala Ser Asp Leu Val Gly Arg Phe Leu Leu
65                  70                  75                  80 gac gcc agc ggc acc cgc tgg cag gac ggc ccc ctc acc ctg gcc gcc     288
Asp Ala Ser Gly Thr Arg Trp Gln Asp Gly Pro Leu Thr Leu Ala Ala
                85                  90                  95 cgc atc ggc gcc atc tgc tat ctc gac gag gtc gtg gag gcc cgc cag     336
Arg Ile Gly Ala Ile Cys Tyr Leu Asp Glu Val Val Glu Ala Arg Gln
            100                 105                 110 gac acc acc gtg gtc atc cac ccc ctg acc gat cac cgc cgc acc ctg     384
Asp Thr Thr Val Val Ile His Pro Leu Thr Asp His Arg Arg Thr Leu
        115                 120                 125 ccg ctg gac aag aaa ggc gag ctg gtg cat gcc cac ccg gat ttc cag     432
Pro Leu Asp Lys Lys Gly Glu Leu Val His Ala His Pro Asp Phe Gln
    130                 135                 140 ttg gtg att tcc tac aat ccc ggc tac cag aac ctg ctg aag gac ctc     480
Leu Val Ile Ser Tyr Asn Pro Gly Tyr Gln Asn Leu Leu Lys Asp Leu
145                 150                 155                 160 aag caa tcg acc aag cag cgc ttc ggc gcg ctg gat ttc ggc tat ccc     528
Lys Gln Ser Thr Lys Gln Arg Phe Gly Ala Leu Asp Phe Gly Tyr Pro
                165                 170                 175 gag acg gct gtc gag gtc gat gtg gtg tcg cac gag acc ggc atc gat     576
Glu Thr Ala Val Glu Val Asp Val Val Ser His Glu Thr Gly Ile Asp
            180                 185                 190 ccc aag atc gcc gag aag ctg gtg cag atc gcc cac cgc gcc cgg aac     624
Pro Lys Ile Ala Glu Lys Leu Val Gln Ile Ala His Arg Ala Arg Asn
        195                 200                 205 ctc aag ggc cac ggc ctg gac gaa ggc atc tcg acc cgc ttg ctg gtc     672
Leu Lys Gly His Gly Leu Asp Glu Gly Ile Ser Thr Arg Leu Leu Val
    210                 215                 220 tat gcc ggc cat ctc atc gcc aag ggt atc gag ccc aga gcg gcc tgc     720
Tyr Ala Gly His Leu Ile Ala Lys Gly Ile Glu Pro Arg Ala Ala Cys
225                 230                 235                 240 atg atg acg ctc gtc cgc ccc ctc acc gac gac ccg gat atg cgc gat     768
Met Met Thr Leu Val Arg Pro Leu Thr Asp Asp Pro Asp Met Arg Asp
                245                 250                 255 acc ctc gac gcc gcc gta gcg acg ttt ttc                             798
Thr Leu Asp Ala Ala Val Ala Thr Phe Phe
            260                 265

<210> SEQ ID NO 30
<211> LENGTH: 266
```

<212> TYPE: PRT
<213> ORGANISM: Methylococcus capsulatus

<400> SEQUENCE: 30

```
Met Ser Ser Thr Glu Gln Tyr Leu Ile Gln Glu Arg Pro Tyr Tyr Arg
1               5                   10                  15

Ala Thr Ala Asp Glu Val Glu Leu Phe Glu Ala Ala Tyr Ala Ala Arg
            20                  25                  30

Met Pro Val Met Leu Lys Gly Pro Thr Gly Cys Gly Lys Thr Arg Phe
        35                  40                  45

Val Glu Tyr Met Ala Trp Lys Leu Lys Arg Pro Leu Ile Thr Val Ala
    50                  55                  60

Cys Asn Glu Asp Met Thr Ala Ser Asp Leu Val Gly Arg Phe Leu Leu
65                  70                  75                  80

Asp Ala Ser Gly Thr Arg Trp Gln Asp Gly Pro Leu Thr Leu Ala Ala
                85                  90                  95

Arg Ile Gly Ala Ile Cys Tyr Leu Asp Glu Val Val Glu Ala Arg Gln
            100                 105                 110

Asp Thr Thr Val Val Ile His Pro Leu Thr Asp His Arg Arg Thr Leu
        115                 120                 125

Pro Leu Asp Lys Lys Gly Glu Leu Val His Ala His Pro Asp Phe Gln
130                 135                 140

Leu Val Ile Ser Tyr Asn Pro Gly Tyr Gln Asn Leu Leu Lys Asp Leu
145                 150                 155                 160

Lys Gln Ser Thr Lys Gln Arg Phe Gly Ala Leu Asp Phe Gly Tyr Pro
                165                 170                 175

Glu Thr Ala Val Glu Val Asp Val Val Ser His Glu Thr Gly Ile Asp
            180                 185                 190

Pro Lys Ile Ala Glu Lys Leu Val Gln Ile Ala His Arg Ala Arg Asn
        195                 200                 205

Leu Lys Gly His Gly Leu Asp Glu Gly Ile Ser Thr Arg Leu Leu Val
    210                 215                 220

Tyr Ala Gly His Leu Ile Ala Lys Gly Ile Glu Pro Arg Ala Ala Cys
225                 230                 235                 240

Met Met Thr Leu Val Arg Pro Leu Thr Asp Pro Asp Met Arg Asp
                245                 250                 255

Thr Leu Asp Ala Ala Val Ala Thr Phe Phe
            260                 265
```

<210> SEQ ID NO 31
<211> LENGTH: 876
<212> TYPE: DNA
<213> ORGANISM: Methylococcus capsulatus
<220> FEATURE:
<221> NAME/KEY: CDS
<222> LOCATION: (1)..(876)

<400> SEQUENCE: 31

```
atg tcc aag aaa cac ccc atc atc gcc atc acc ggt tcg tcc ggc gcg      48
Met Ser Lys Lys His Pro Ile Ile Ala Ile Thr Gly Ser Ser Gly Ala
1               5                   10                  15 ggc acg acc acc gta aaa tgc gcc ttc gag cat att ttc ttc agg ctc      96
Gly Thr Thr Thr Val Lys Cys Ala Phe Glu His Ile Phe Phe Arg Leu
            20                  25                  30 gga ctc aaa cca ctg gtc atc gag ggc gac agc ttt cat cgc tat gac     144
Gly Leu Lys Pro Leu Val Ile Glu Gly Asp Ser Phe His Arg Tyr Asp
        35                  40                  45
```

```
cgt gtg gaa atg cgt gcg cag atc gac aag gcc aga cgt gaa gga cgt      192
Arg Val Glu Met Arg Ala Gln Ile Asp Lys Ala Arg Arg Glu Gly Arg
    50                  55                  60 cat ttc agc cat ttt tcg atc gag gcc aac atc ctg gac gag ctc gaa      240
His Phe Ser His Phe Ser Ile Glu Ala Asn Ile Leu Asp Glu Leu Glu
65                  70                  75                  80 aac gtt ttt cgg cac tac ggg gaa acg gga acg gct cgc cgc cgt ttt      288
Asn Val Phe Arg His Tyr Gly Glu Thr Gly Thr Ala Arg Arg Arg Phe
                85                  90                  95 tat gtc cac aat gaa gcc gag agt cag cgg ctg ggg ggt tac aaa ccg      336
Tyr Val His Asn Glu Ala Glu Ser Gln Arg Leu Gly Gly Tyr Lys Pro
            100                 105                 110 gga acc ttc acc cca tgg gaa gaa gta cct gca ggg acg gat ctg ctg      384
Gly Thr Phe Thr Pro Trp Glu Glu Val Pro Ala Gly Thr Asp Leu Leu
        115                 120                 125 ttt tac gaa ggt ctg cac gga ggc gtg atc acc gac cgc atc aat gtc      432
Phe Tyr Glu Gly Leu His Gly Gly Val Ile Thr Asp Arg Ile Asn Val
    130                 135                 140 aga aaa tac gtc gat ctt ctc gtc ggc gtg gtt ccc atc gtc aat ttg      480
Arg Lys Tyr Val Asp Leu Leu Val Gly Val Val Pro Ile Val Asn Leu
145                 150                 155                 160 gaa tgg att caa aaa atc cat cgc gat acc gcc gaa cgc ggc tat aag      528
Glu Trp Ile Gln Lys Ile His Arg Asp Thr Ala Glu Arg Gly Tyr Lys
                165                 170                 175 ccc gag gac gtt acg gaa acg ata ctg cgc cgc atg gat gac tac gtc      576
Pro Glu Asp Val Thr Glu Thr Ile Leu Arg Arg Met Asp Asp Tyr Val
            180                 185                 190 aag gtc atc acc ccc caa ttt tca cag acc gac atc aat ttc cag cgt      624
Lys Val Ile Thr Pro Gln Phe Ser Gln Thr Asp Ile Asn Phe Gln Arg
        195                 200                 205 gtc ccg acg gtc gat act tcc aat ccg ttc att gcc cgg gat att ccc      672
Val Pro Thr Val Asp Thr Ser Asn Pro Phe Ile Ala Arg Asp Ile Pro
    210                 215                 220 acc ccg gat gag agt ttc gtc atc atc cgc ttc aaa gag cct ggc aaa      720
Thr Pro Asp Glu Ser Phe Val Ile Ile Arg Phe Lys Glu Pro Gly Lys
225                 230                 235                 240 ttc aac gtg gat ttc cct tat ctc ctg gcc atg ctg caa aac tcc ttc      768
Phe Asn Val Asp Phe Pro Tyr Leu Leu Ala Met Leu Gln Asn Ser Phe
                245                 250                 255 atg tca cga cat aat tcg atc gtg att ccg gga ggc aag atg gga ctc      816
Met Ser Arg His Asn Ser Ile Val Ile Pro Gly Gly Lys Met Gly Leu
            260                 265                 270 gca atg gag atc att ttc cgg ccg ata ctc gaa cgc atg atg gcg gat      864
Ala Met Glu Ile Ile Phe Arg Pro Ile Leu Glu Arg Met Met Ala Asp
        275                 280                 285 cgt gag aaa ggc                                                      876
Arg Glu Lys Gly
    290
```

<210> SEQ ID NO 32
<211> LENGTH: 292
<212> TYPE: PRT
<213> ORGANISM: Methylococcus capsulatus

<400> SEQUENCE: 32

```
Met Ser Lys Lys His Pro Ile Ile Ala Ile Thr Gly Ser Ser Gly Ala
1               5                   10                  15

Gly Thr Thr Thr Val Lys Cys Ala Phe Glu His Ile Phe Phe Arg Leu
            20                  25                  30

Gly Leu Lys Pro Leu Val Ile Glu Gly Asp Ser Phe His Arg Tyr Asp
```

```
                35                  40                  45
Arg Val Glu Met Arg Ala Gln Ile Asp Lys Ala Arg Arg Glu Gly Arg
 50                  55                  60

His Phe Ser His Phe Ser Ile Glu Ala Asn Ile Leu Asp Glu Leu Glu
65                  70                  75                  80

Asn Val Phe Arg His Tyr Gly Glu Thr Gly Thr Ala Arg Arg Arg Phe
                85                  90                  95

Tyr Val His Asn Glu Ala Glu Ser Gln Arg Leu Gly Gly Tyr Lys Pro
            100                 105                 110

Gly Thr Phe Thr Pro Trp Glu Val Pro Ala Gly Thr Asp Leu Leu
        115                 120                 125

Phe Tyr Glu Gly Leu His Gly Gly Val Ile Thr Asp Arg Ile Asn Val
130                 135                 140

Arg Lys Tyr Val Asp Leu Leu Val Gly Val Val Pro Ile Val Asn Leu
145                 150                 155                 160

Glu Trp Ile Gln Lys Ile His Arg Asp Thr Ala Glu Arg Gly Tyr Lys
                165                 170                 175

Pro Glu Asp Val Thr Glu Thr Ile Leu Arg Arg Met Asp Asp Tyr Val
            180                 185                 190

Lys Val Ile Thr Pro Gln Phe Ser Gln Thr Asp Ile Asn Phe Gln Arg
        195                 200                 205

Val Pro Thr Val Asp Thr Ser Asn Pro Phe Ile Ala Arg Asp Ile Pro
210                 215                 220

Thr Pro Asp Glu Ser Phe Val Ile Ile Arg Phe Lys Glu Pro Gly Lys
225                 230                 235                 240

Phe Asn Val Asp Phe Pro Tyr Leu Leu Ala Met Leu Gln Asn Ser Phe
                245                 250                 255

Met Ser Arg His Asn Ser Ile Val Ile Pro Gly Gly Lys Met Gly Leu
            260                 265                 270

Ala Met Glu Ile Ile Phe Arg Pro Ile Leu Glu Arg Met Met Ala Asp
        275                 280                 285

Arg Glu Lys Gly
    290

<210> SEQ ID NO 33
<211> LENGTH: 1050
<212> TYPE: DNA
<213> ORGANISM: Methylomicrobium alcaliphilum
<220> FEATURE:
<221> NAME/KEY: CDS
<222> LOCATION: (1)..(1050)

<400> SEQUENCE: 33 atg aac tac caa aac gac gac ttg agg atc aaa gaa atc aaa gaa ttg      48
Met Asn Tyr Gln Asn Asp Asp Leu Arg Ile Lys Glu Ile Lys Glu Leu
1               5                   10                  15 ttg ccg ccg gtc gcg ctt ttg gag aaa ttc cct gcc acc gag aac gct      96
Leu Pro Pro Val Ala Leu Leu Glu Lys Phe Pro Ala Thr Glu Asn Ala
            20                  25                  30 gct aac acc gtg gcg cat gcg aga aaa gct att cat aaa atc ctg aag     144
Ala Asn Thr Val Ala His Ala Arg Lys Ala Ile His Lys Ile Leu Lys
        35                  40                  45 ggc aac gat gac cgt ttg ttg gta gtg atc ggg cct tgt agt atc cat     192
Gly Asn Asp Asp Arg Leu Leu Val Val Ile Gly Pro Cys Ser Ile His
    50                  55                  60 gac ccg gtc gcc gcc aaa gaa tat gcg acc cgc ttg ctg gct ctg cgt     240
Asp Pro Val Ala Ala Lys Glu Tyr Ala Thr Arg Leu Leu Ala Leu Arg
```

```
                  65                  70                  75                  80
gag gaa ctg aaa gac gaa ctg gaa atc gta atg aga gtc tac ttc gaa        288
Glu Glu Leu Lys Asp Glu Leu Glu Ile Val Met Arg Val Tyr Phe Glu
                    85                  90                  95 aag cct cgc act acc gtc ggt tgg aaa ggc ctt ata aac gac cct cac        336
Lys Pro Arg Thr Thr Val Gly Trp Lys Gly Leu Ile Asn Asp Pro His
                100                 105                 110 atg gac aat tct ttc caa atc aac gac ggc ttg cgt atc gcg cgt aaa        384
Met Asp Asn Ser Phe Gln Ile Asn Asp Gly Leu Arg Ile Ala Arg Lys
            115                 120                 125 ctg ctt cta gac att aac gac tct ggc ttg cct gcc gca ggt gaa ttc        432
Leu Leu Leu Asp Ile Asn Asp Ser Gly Leu Pro Ala Ala Gly Glu Phe
        130                 135                 140 tta aac atg ata act cca caa tac ttg gcc gac ctg atg agt tgg ggt        480
Leu Asn Met Ile Thr Pro Gln Tyr Leu Ala Asp Leu Met Ser Trp Gly
145                 150                 155                 160 gcc att ggc gcc aga act aca gaa tcc caa gtg cac cgg gaa ttg gcg        528
Ala Ile Gly Ala Arg Thr Thr Glu Ser Gln Val His Arg Glu Leu Ala
                165                 170                 175 agc ggc cta tct tgt ccg gtg ggc ttc aaa aac ggc acc gac ggc acg        576
Ser Gly Leu Ser Cys Pro Val Gly Phe Lys Asn Gly Thr Asp Gly Thr
            180                 185                 190 atc aag gtc gcc att gat gct atc aac gcg gcc ggc gcc ccg cat tgt        624
Ile Lys Val Ala Ile Asp Ala Ile Asn Ala Ala Gly Ala Pro His Cys
        195                 200                 205 ttc ctg tcg gtt acg aaa tgg ggg cat agc gcc atc gta aac acg tca        672
Phe Leu Ser Val Thr Lys Trp Gly His Ser Ala Ile Val Asn Thr Ser
    210                 215                 220 ggc aat ggg gac tgt cat atc ata ctg cgg ggt ggc aaa gaa ccg aac        720
Gly Asn Gly Asp Cys His Ile Ile Leu Arg Gly Gly Lys Glu Pro Asn
225                 230                 235                 240 tac tct gct aaa cat gta gct gaa gtc aaa gag ggt ttg aac aaa gct        768
Tyr Ser Ala Lys His Val Ala Glu Val Lys Glu Gly Leu Asn Lys Ala
                245                 250                 255 ggc cta ccg gcg caa gtc atg atc gat ttt agc cat gcg aac tcg tct        816
Gly Leu Pro Ala Gln Val Met Ile Asp Phe Ser His Ala Asn Ser Ser
            260                 265                 270 aag caa ttc aaa aaa caa atg gac gtt tgc gcg gac gtt tgc caa cag        864
Lys Gln Phe Lys Lys Gln Met Asp Val Cys Ala Asp Val Cys Gln Gln
        275                 280                 285 atc gcc gga gga gaa aaa gcc ata atc ggc gta atg gtt gaa tcg cac        912
Ile Ala Gly Gly Glu Lys Ala Ile Ile Gly Val Met Val Glu Ser His
    290                 295                 300 ctg gtt gaa gga aac caa tcg ctg gaa tcg ggt gaa cct ctg gct tac        960
Leu Val Glu Gly Asn Gln Ser Leu Glu Ser Gly Glu Pro Leu Ala Tyr
305                 310                 315                 320 ggt aaa tct ata aca gac gcg tgt ata ggc tgg gag gac aca gac gcc       1008
Gly Lys Ser Ile Thr Asp Ala Cys Ile Gly Trp Glu Asp Thr Asp Ala
                325                 330                 335 ctg ctg cgt caa ttg gcg aat gct gtc aaa gcc cga agg ggc                1050
Leu Leu Arg Gln Leu Ala Asn Ala Val Lys Ala Arg Arg Gly
            340                 345                 350

<210> SEQ ID NO 34
<211> LENGTH: 350
<212> TYPE: PRT
<213> ORGANISM: Methylomicrobium alcaliphilum

<400> SEQUENCE: 34

Met Asn Tyr Gln Asn Asp Asp Leu Arg Ile Lys Glu Ile Lys Glu Leu
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Leu | Pro | Pro | Val | Ala | Leu | Leu | Glu | Lys | Phe | Pro | Ala | Thr | Glu | Asn | Ala |
|   |   |   | 20 |   |   |   |   | 25 |   |   |   |   | 30 |   |   |
| Ala | Asn | Thr | Val | Ala | His | Ala | Arg | Lys | Ala | Ile | His | Lys | Ile | Leu | Lys |
|   |   | 35 |   |   |   |   | 40 |   |   |   |   | 45 |   |   |   |
| Gly | Asn | Asp | Asp | Arg | Leu | Leu | Val | Val | Ile | Gly | Pro | Cys | Ser | Ile | His |
|   | 50 |   |   |   |   | 55 |   |   |   |   | 60 |   |   |   |   |
| Asp | Pro | Val | Ala | Ala | Lys | Glu | Tyr | Ala | Thr | Arg | Leu | Leu | Ala | Leu | Arg |
| 65 |   |   |   |   | 70 |   |   |   |   | 75 |   |   |   |   | 80 |
| Glu | Glu | Leu | Lys | Asp | Glu | Leu | Glu | Ile | Val | Met | Arg | Val | Tyr | Phe | Glu |
|   |   |   |   | 85 |   |   |   |   | 90 |   |   |   |   | 95 |   |
| Lys | Pro | Arg | Thr | Thr | Val | Gly | Trp | Lys | Gly | Leu | Ile | Asn | Asp | Pro | His |
|   |   |   | 100 |   |   |   |   | 105 |   |   |   |   | 110 |   |   |
| Met | Asp | Asn | Ser | Phe | Gln | Ile | Asn | Asp | Gly | Leu | Arg | Ile | Ala | Arg | Lys |
|   |   | 115 |   |   |   |   | 120 |   |   |   |   | 125 |   |   |   |
| Leu | Leu | Leu | Asp | Ile | Asn | Asp | Ser | Gly | Leu | Pro | Ala | Ala | Gly | Glu | Phe |
|   | 130 |   |   |   |   | 135 |   |   |   |   | 140 |   |   |   |   |
| Leu | Asn | Met | Ile | Thr | Pro | Gln | Tyr | Leu | Ala | Asp | Leu | Met | Ser | Trp | Gly |
| 145 |   |   |   |   | 150 |   |   |   |   | 155 |   |   |   |   | 160 |
| Ala | Ile | Gly | Ala | Arg | Thr | Thr | Glu | Ser | Gln | Val | His | Arg | Glu | Leu | Ala |
|   |   |   |   | 165 |   |   |   |   | 170 |   |   |   |   | 175 |   |
| Ser | Gly | Leu | Ser | Cys | Pro | Val | Gly | Phe | Lys | Asn | Gly | Thr | Asp | Gly | Thr |
|   |   |   | 180 |   |   |   |   | 185 |   |   |   |   | 190 |   |   |
| Ile | Lys | Val | Ala | Ile | Asp | Ala | Ile | Asn | Ala | Ala | Gly | Ala | Pro | His | Cys |
|   |   | 195 |   |   |   |   | 200 |   |   |   |   | 205 |   |   |   |
| Phe | Leu | Ser | Val | Thr | Lys | Trp | Gly | His | Ser | Ala | Ile | Val | Asn | Thr | Ser |
|   | 210 |   |   |   |   | 215 |   |   |   |   | 220 |   |   |   |   |
| Gly | Asn | Gly | Asp | Cys | His | Ile | Ile | Leu | Arg | Gly | Gly | Lys | Glu | Pro | Asn |
| 225 |   |   |   |   | 230 |   |   |   |   | 235 |   |   |   |   | 240 |
| Tyr | Ser | Ala | Lys | His | Val | Ala | Glu | Val | Lys | Glu | Gly | Leu | Asn | Lys | Ala |
|   |   |   |   | 245 |   |   |   |   | 250 |   |   |   |   | 255 |   |
| Gly | Leu | Pro | Ala | Gln | Val | Met | Ile | Asp | Phe | Ser | His | Ala | Asn | Ser | Ser |
|   |   |   | 260 |   |   |   |   | 265 |   |   |   |   | 270 |   |   |
| Lys | Gln | Phe | Lys | Lys | Gln | Met | Asp | Val | Cys | Ala | Asp | Val | Cys | Gln | Gln |
|   |   | 275 |   |   |   |   | 280 |   |   |   |   | 285 |   |   |   |
| Ile | Ala | Gly | Gly | Glu | Lys | Ala | Ile | Ile | Gly | Val | Met | Val | Glu | Ser | His |
|   | 290 |   |   |   |   | 295 |   |   |   |   | 300 |   |   |   |   |
| Leu | Val | Glu | Gly | Asn | Gln | Ser | Leu | Glu | Ser | Gly | Glu | Pro | Leu | Ala | Tyr |
| 305 |   |   |   |   | 310 |   |   |   |   | 315 |   |   |   |   | 320 |
| Gly | Lys | Ser | Ile | Thr | Asp | Ala | Cys | Ile | Gly | Trp | Glu | Asp | Thr | Asp | Ala |
|   |   |   |   | 325 |   |   |   |   | 330 |   |   |   |   | 335 |   |
| Leu | Leu | Arg | Gln | Leu | Ala | Asn | Ala | Val | Lys | Ala | Arg | Arg | Gly |   |   |
|   |   |   | 340 |   |   |   |   | 345 |   |   |   |   | 350 |   |   |

```
<210> SEQ ID NO 35
<211> LENGTH: 1560
<212> TYPE: DNA
<213> ORGANISM: Methylomicrobium alcaliphilum
<220> FEATURE:
<221> NAME/KEY: CDS
<222> LOCATION: (1)..(1560)

<400> SEQUENCE: 35 atg caa acg caa aaa cct acc ttg gaa tta tta acg tgc gaa ggt gcc    48
Met Gln Thr Gln Lys Pro Thr Leu Glu Leu Leu Thr Cys Glu Gly Ala
1               5                   10                  15
```

```
tac cgc gac aac cct act gcc ttg ttc cat caa ttg tgc ggt gac cgt        96
Tyr Arg Asp Asn Pro Thr Ala Leu Phe His Gln Leu Cys Gly Asp Arg
             20                  25                  30 cca gcc act ttg cta cta gaa agg gca gac atc gac tcg aag gat gat       144
Pro Ala Thr Leu Leu Leu Glu Arg Ala Asp Ile Asp Ser Lys Asp Asp
         35                  40                  45 ctt aaa tcg cta ctg tta gtg gac tca gcg ttg cgt atc acg gct ctg       192
Leu Lys Ser Leu Leu Leu Val Asp Ser Ala Leu Arg Ile Thr Ala Leu
     50                  55                  60 ggt gac act gtg act atc caa gcg ttg tcg ggt aac ggc gaa gcg ctg       240
Gly Asp Thr Val Thr Ile Gln Ala Leu Ser Gly Asn Gly Glu Ala Leu
65                  70                  75                  80 tta gcc ctc ctg gac aac gct tta ccc gcc ggt gtc gaa tct gaa caa       288
Leu Ala Leu Leu Asp Asn Ala Leu Pro Ala Gly Val Glu Ser Glu Gln
                 85                  90                  95 tcg ccc aac tgc aga gtc ttg cgt ttc cca ccg gtc tcg ccg ttg ctg       336
Ser Pro Asn Cys Arg Val Leu Arg Phe Pro Pro Val Ser Pro Leu Leu
             100                 105                 110 gac gag gac gct cgt ctg tgt tcg ttg tct gtt ttc gac gcc ttc agg       384
Asp Glu Asp Ala Arg Leu Cys Ser Leu Ser Val Phe Asp Ala Phe Arg
         115                 120                 125 ctg ttg caa aac ctc ctg aac gtc cca aaa gag gaa cga gaa gcg atg       432
Leu Leu Gln Asn Leu Leu Asn Val Pro Lys Glu Glu Arg Glu Ala Met
     130                 135                 140 ttt ttc ggt ggc ttg ttc agc tac gac ttg gtt gcg gga ttc gaa gac       480
Phe Phe Gly Gly Leu Phe Ser Tyr Asp Leu Val Ala Gly Phe Glu Asp
145                 150                 155                 160 ctg ccc caa ttg tct gcc gaa aac aat tgc ccg gac ttc tgc ttt tac       528
Leu Pro Gln Leu Ser Ala Glu Asn Asn Cys Pro Asp Phe Cys Phe Tyr
                 165                 170                 175 ttg gcc gaa acc cta atg gtg att gac cat cag aaa aag tcg act cgc       576
Leu Ala Glu Thr Leu Met Val Ile Asp His Gln Lys Lys Ser Thr Arg
             180                 185                 190 ata caa gcg tct ctg ttc gcg cct aac gaa gag gaa aaa cag cgt ttg       624
Ile Gln Ala Ser Leu Phe Ala Pro Asn Glu Glu Glu Lys Gln Arg Leu
         195                 200                 205 act gca cgg ctg aac gaa tta cgc cag cag ctg acg gaa gcg gcc cca       672
Thr Ala Arg Leu Asn Glu Leu Arg Gln Gln Leu Thr Glu Ala Ala Pro
     210                 215                 220 cca ttg ccg gtc gtt tcg gtc cca cat atg cgg tgt gaa tgt aac caa       720
Pro Leu Pro Val Val Ser Val Pro His Met Arg Cys Glu Cys Asn Gln
225                 230                 235                 240 tcg gac gaa gaa ttc ggc ggt gtt gtc cgt ctg ctg caa aaa gcc atc       768
Ser Asp Glu Glu Phe Gly Gly Val Val Arg Leu Leu Gln Lys Ala Ile
                 245                 250                 255 cgc gcc ggg gaa ata ttc caa gtt gtc ccg tca aga aga ttt tcc ctc       816
Arg Ala Gly Glu Ile Phe Gln Val Val Pro Ser Arg Arg Phe Ser Leu
             260                 265                 270 cca tgc cct agt cct ctt gct gcc tac tac gtc ctc aaa aaa tct aac       864
Pro Cys Pro Ser Pro Leu Ala Ala Tyr Tyr Val Leu Lys Lys Ser Asn
         275                 280                 285 cca agc ccc tac atg ttc ttc atg caa gac aac gat ttt act ctg ttc       912
Pro Ser Pro Tyr Met Phe Phe Met Gln Asp Asn Asp Phe Thr Leu Phe
     290                 295                 300 ggg gcg tcg cct gaa tcg tcg ctg aaa tac gac gcg acc tcg cgc cag       960
Gly Ala Ser Pro Glu Ser Ser Leu Lys Tyr Asp Ala Thr Ser Arg Gln
305                 310                 315                 320 atc gag atc tac cct ata gcg ggc acg cgc cca cgt ggc cgt aga gcc      1008
Ile Glu Ile Tyr Pro Ile Ala Gly Thr Arg Pro Arg Gly Arg Arg Ala
```

```
                    325                 330                 335
gac ggc tcg cta gat cgc gac ctg gat agc cgc atc gaa ctg gaa atg    1056
Asp Gly Ser Leu Asp Arg Asp Leu Asp Ser Arg Ile Glu Leu Glu Met
            340                 345                 350 cga acg gac cat aag gaa ctt agt gag cat ctg atg ttg gtg gac ctc    1104
Arg Thr Asp His Lys Glu Leu Ser Glu His Leu Met Leu Val Asp Leu
                355                 360                 365 gcc cgt aat gac cta gcg cgt atc tgc acg cct ggt tcg cga tat gtc    1152
Ala Arg Asn Asp Leu Ala Arg Ile Cys Thr Pro Gly Ser Arg Tyr Val
        370                 375                 380 gcc gac ttg acc aaa gtg gac cgt tac tct tac gtc atg cat ctg gtc    1200
Ala Asp Leu Thr Lys Val Asp Arg Tyr Ser Tyr Val Met His Leu Val
385                 390                 395                 400 tct cgt gtg gta gga gaa ttg cgc cac gac ctc gac gct ctc cat gcg    1248
Ser Arg Val Val Gly Glu Leu Arg His Asp Leu Asp Ala Leu His Ala
                405                 410                 415 tac cgc gct tgc atg aac atg ggc acg ctc tcg ggc gcc cca aaa gtc    1296
Tyr Arg Ala Cys Met Asn Met Gly Thr Leu Ser Gly Ala Pro Lys Val
            420                 425                 430 cga gct atg caa ttg atc gcg gaa gct gaa ggg cgc cgt cgt ggt tcc    1344
Arg Ala Met Gln Leu Ile Ala Glu Ala Glu Gly Arg Arg Arg Gly Ser
        435                 440                 445 tac ggc ggg gcg gtt ggc tac ttc act gct cat ggc gac cta gac acc    1392
Tyr Gly Gly Ala Val Gly Tyr Phe Thr Ala His Gly Asp Leu Asp Thr
450                 455                 460 tgc atc gtg ata cgt agt gct ctc gtc gaa aac ggc atc gct aca gtg    1440
Cys Ile Val Ile Arg Ser Ala Leu Val Glu Asn Gly Ile Ala Thr Val
465                 470                 475                 480 caa gcc gga gcg ggt gtt gtc ctt gac tct gtt ccg caa tca gaa gct    1488
Gln Ala Gly Ala Gly Val Val Leu Asp Ser Val Pro Gln Ser Glu Ala
                485                 490                 495 gat gaa act cgt aat aaa gcg cgt gcg gtg ctg cgt gct atc gct acg    1536
Asp Glu Thr Arg Asn Lys Ala Arg Ala Val Leu Arg Ala Ile Ala Thr
            500                 505                 510 gct cac cat gct caa gaa acg ttc                                    1560
Ala His His Ala Gln Glu Thr Phe
        515                 520

<210> SEQ ID NO 36
<211> LENGTH: 520
<212> TYPE: PRT
<213> ORGANISM: Methylomicrobium alcaliphilum

<400> SEQUENCE: 36

Met Gln Thr Gln Lys Pro Thr Leu Glu Leu Leu Thr Cys Glu Gly Ala
1               5                   10                  15

Tyr Arg Asp Asn Pro Thr Ala Leu Phe His Gln Leu Cys Gly Asp Arg
            20                  25                  30

Pro Ala Thr Leu Leu Leu Glu Arg Ala Asp Ile Asp Ser Lys Asp Asp
        35                  40                  45

Leu Lys Ser Leu Leu Leu Val Asp Ser Ala Leu Arg Ile Thr Ala Leu
    50                  55                  60

Gly Asp Thr Val Thr Ile Gln Ala Leu Ser Gly Asn Gly Glu Ala Leu
65                  70                  75                  80

Leu Ala Leu Leu Asp Asn Ala Leu Pro Ala Gly Val Glu Ser Glu Gln
                85                  90                  95

Ser Pro Asn Cys Arg Val Leu Arg Phe Pro Pro Val Ser Pro Leu Leu
            100                 105                 110
```

```
Asp Glu Asp Ala Arg Leu Cys Ser Leu Ser Val Phe Asp Ala Phe Arg
            115                 120                 125
Leu Leu Gln Asn Leu Leu Asn Val Pro Lys Glu Glu Arg Glu Ala Met
130                 135                 140
Phe Phe Gly Gly Leu Phe Ser Tyr Asp Leu Val Ala Gly Phe Glu Asp
145                 150                 155                 160
Leu Pro Gln Leu Ser Ala Glu Asn Asn Cys Pro Asp Phe Cys Phe Tyr
                165                 170                 175
Leu Ala Glu Thr Leu Met Val Ile Asp His Gln Lys Lys Ser Thr Arg
            180                 185                 190
Ile Gln Ala Ser Leu Phe Ala Pro Asn Glu Glu Glu Lys Gln Arg Leu
        195                 200                 205
Thr Ala Arg Leu Asn Glu Leu Arg Gln Gln Leu Thr Glu Ala Ala Pro
    210                 215                 220
Pro Leu Pro Val Val Ser Val Pro His Met Arg Cys Glu Cys Asn Gln
225                 230                 235                 240
Ser Asp Glu Glu Phe Gly Gly Val Val Arg Leu Leu Gln Lys Ala Ile
                245                 250                 255
Arg Ala Gly Glu Ile Phe Gln Val Val Pro Ser Arg Arg Phe Ser Leu
            260                 265                 270
Pro Cys Pro Ser Pro Leu Ala Ala Tyr Tyr Val Leu Lys Lys Ser Asn
        275                 280                 285
Pro Ser Pro Tyr Met Phe Phe Met Gln Asp Asn Asp Phe Thr Leu Phe
    290                 295                 300
Gly Ala Ser Pro Glu Ser Ser Leu Lys Tyr Asp Ala Thr Ser Arg Gln
305                 310                 315                 320
Ile Glu Ile Tyr Pro Ile Ala Gly Thr Arg Pro Arg Gly Arg Arg Ala
                325                 330                 335
Asp Gly Ser Leu Asp Arg Asp Leu Asp Ser Arg Ile Glu Leu Glu Met
            340                 345                 350
Arg Thr Asp His Lys Glu Leu Ser Glu His Leu Met Leu Val Asp Leu
        355                 360                 365
Ala Arg Asn Asp Leu Ala Arg Ile Cys Thr Pro Gly Ser Arg Tyr Val
    370                 375                 380
Ala Asp Leu Thr Lys Val Asp Arg Tyr Ser Tyr Val Met His Leu Val
385                 390                 395                 400
Ser Arg Val Val Gly Glu Leu Arg His Asp Leu Asp Ala Leu His Ala
                405                 410                 415
Tyr Arg Ala Cys Met Asn Met Gly Thr Leu Ser Gly Ala Pro Lys Val
            420                 425                 430
Arg Ala Met Gln Leu Ile Ala Glu Ala Glu Gly Arg Arg Arg Gly Ser
        435                 440                 445
Tyr Gly Gly Ala Val Gly Tyr Phe Thr Ala His Gly Asp Leu Asp Thr
    450                 455                 460
Cys Ile Val Ile Arg Ser Ala Leu Val Glu Asn Gly Ile Ala Thr Val
465                 470                 475                 480
Gln Ala Gly Ala Gly Val Val Leu Asp Ser Val Pro Gln Ser Glu Ala
                485                 490                 495
Asp Glu Thr Arg Asn Lys Ala Arg Ala Val Leu Arg Ala Ile Ala Thr
            500                 505                 510
Ala His His Ala Gln Glu Thr Phe
        515                 520
```

```
<210> SEQ ID NO 37
<211> LENGTH: 2409
<212> TYPE: DNA
<213> ORGANISM: Methylomicrobium alcaliphilum
<220> FEATURE:
<221> NAME/KEY: CDS
<222> LOCATION: (1)..(2409)

<400> SEQUENCE: 37 atg tca gaa aaa ttc aag tac atc cgt tgg ttt gag gaa cta acg atc        48
Met Ser Glu Lys Phe Lys Tyr Ile Arg Trp Phe Glu Glu Leu Thr Ile
1               5                   10                  15 gac gat att ccc ttg gtt ggc ggc aag aat gcc tcg ctg ggc gaa atg        96
Asp Asp Ile Pro Leu Val Gly Gly Lys Asn Ala Ser Leu Gly Glu Met
            20                  25                  30 tac ctc gaa cta gcc acc gaa ggc atc cgc gtg ccg aac ggc ttc gcg       144
Tyr Leu Glu Leu Ala Thr Glu Gly Ile Arg Val Pro Asn Gly Phe Ala
        35                  40                  45 att act gcg gaa ggt tac cgg cac atg ctc gat aaa gcg gat gcc tgg       192
Ile Thr Ala Glu Gly Tyr Arg His Met Leu Asp Lys Ala Asp Ala Trp
    50                  55                  60 gaa gcc tta cat gag gcg ctc gat acc ttg aat ccg gac gat gtg aac       240
Glu Ala Leu His Glu Ala Leu Asp Thr Leu Asn Pro Asp Asp Val Asn
65                  70                  75                  80 gac ttg gct aag cga gcc aga aaa gcg cga gat atc gtt tac gcg gcg       288
Asp Leu Ala Lys Arg Ala Arg Lys Ala Arg Asp Ile Val Tyr Ala Ala
                85                  90                  95 ccg cta tcc gaa gac ttg gag cat gaa att ctg att gct ttc gat caa       336
Pro Leu Ser Glu Asp Leu Glu His Glu Ile Leu Ile Ala Phe Asp Gln
            100                 105                 110 ctg cag cga caa tac gat gag gaa ttg acc gtt gcg gtt aga agt tcg       384
Leu Gln Arg Gln Tyr Asp Glu Glu Leu Thr Val Ala Val Arg Ser Ser
        115                 120                 125 gcg acg gcc gag gat ttg ccg acc gcg agc ttt gcg ggt cag cag gac       432
Ala Thr Ala Glu Asp Leu Pro Thr Ala Ser Phe Ala Gly Gln Gln Asp
    130                 135                 140 acc tat ctg aac gtg cat agc gga cag gct ctg ctc gat gcg tgt aaa       480
Thr Tyr Leu Asn Val His Ser Gly Gln Ala Leu Leu Asp Ala Cys Lys
145                 150                 155                 160 cgc tgt ttc gcg agc ctg ttc acc gat cgg gcg att cat tat cgg atc       528
Arg Cys Phe Ala Ser Leu Phe Thr Asp Arg Ala Ile His Tyr Arg Ile
                165                 170                 175 gat caa ggt ttc gat cat ttc aag gtg tcg tta tcg atc ggc gtg atg       576
Asp Gln Gly Phe Asp His Phe Lys Val Ser Leu Ser Ile Gly Val Met
            180                 185                 190 aaa atg gtc cgt tcg gat ttg gcg tcg agc ggc gta atg ttc tcg atc       624
Lys Met Val Arg Ser Asp Leu Ala Ser Ser Gly Val Met Phe Ser Ile
        195                 200                 205 gat acc gaa tcg ggc ttc aaa gat gcg gta ttc att acc ggt gct tac       672
Asp Thr Glu Ser Gly Phe Lys Asp Ala Val Phe Ile Thr Gly Ala Tyr
    210                 215                 220 ggc ctc ggt gaa aat gtc gtg cag ggt tcg gtc gac ccg gac gag ttt       720
Gly Leu Gly Glu Asn Val Val Gln Gly Ser Val Asp Pro Asp Glu Phe
225                 230                 235                 240 tat gtg cat aag cct acc ttc gag caa ggt cat cgt tgt gtg ttg cga       768
Tyr Val His Lys Pro Thr Phe Glu Gln Gly His Arg Cys Val Leu Arg
                245                 250                 255 cgg tcg ctg ggc gcg aaa aaa att aag atg gtc tat agc gaa ggc cgt       816
Arg Ser Leu Gly Ala Lys Lys Ile Lys Met Val Tyr Ser Glu Gly Arg
            260                 265                 270 acg cgc gag caa act tgt aat gtc gtg acg tca gcc gag gag cgt tcg       864
Thr Arg Glu Gln Thr Cys Asn Val Val Thr Ser Ala Glu Glu Arg Ser
```

```
Thr Arg Glu Gln Thr Cys Asn Val Val Thr Ser Ala Glu Arg Ser
        275                 280                 285 caa ttt tgc ttg agc gac gac gag gtg ctg act ttg gcc gat tac gcg      912
Gln Phe Cys Leu Ser Asp Asp Glu Val Leu Thr Leu Ala Asp Tyr Ala
    290                 295                 300 atc aag atc gag aag cac tac agc gcg aag gct ggc atg ccc agg cca      960
Ile Lys Ile Glu Lys His Tyr Ser Ala Lys Ala Gly Met Pro Arg Pro
305                 310                 315                 320 atg gat atc gaa tgg gcg aag gac ggg ctg gac gga caa ctc tat atc     1008
Met Asp Ile Glu Trp Ala Lys Asp Gly Leu Asp Gly Gln Leu Tyr Ile
                325                 330                 335 gta cag gca cgg ccc gaa aca gtc gca tcg cag ttg agc ggg acg acg     1056
Val Gln Ala Arg Pro Glu Thr Val Ala Ser Gln Leu Ser Gly Thr Thr
        340                 345                 350 ctc gaa caa tac gaa ctg aaa caa aag gcc gag gcg att gtc aca gga     1104
Leu Glu Gln Tyr Glu Leu Lys Gln Lys Ala Glu Ala Ile Val Thr Gly
    355                 360                 365 cga gcg gtc ggc agc aag atc gcg gtc ggt acc gcg cat gtg atc aaa     1152
Arg Ala Val Gly Ser Lys Ile Ala Val Gly Thr Ala His Val Ile Lys
370                 375                 380 aat gtc agc caa ttg aat acc ttc aaa ccc ggc gaa gtg ttg att acc     1200
Asn Val Ser Gln Leu Asn Thr Phe Lys Pro Gly Glu Val Leu Ile Thr
385                 390                 395                 400 gac atg acc aca ccg gat tgg gaa ccg gtc atg aaa acg gcc gca gcg     1248
Asp Met Thr Thr Pro Asp Trp Glu Pro Val Met Lys Thr Ala Ala Ala
                405                 410                 415 atc gtg acc aat cga ggt ggg cgc acc tgt cat gcc gca atc atc gct     1296
Ile Val Thr Asn Arg Gly Gly Arg Thr Cys His Ala Ala Ile Ile Ala
        420                 425                 430 cgc gag ctg ggt gtt ccg gcc gtg atc ggc tgc gac aat gcg acc gaa     1344
Arg Glu Leu Gly Val Pro Ala Val Ile Gly Cys Asp Asn Ala Thr Glu
    435                 440                 445 acg att aaa acc ggt acg act gtc acg gta tcc tgc gcc gaa ggc gat     1392
Thr Ile Lys Thr Gly Thr Thr Val Thr Val Ser Cys Ala Glu Gly Asp
450                 455                 460 gcc ggc aag gtt tat gac ggc gag ttg agt ttc gat gtc aat aag acc     1440
Ala Gly Lys Val Tyr Asp Gly Glu Leu Ser Phe Asp Val Asn Lys Thr
465                 470                 475                 480 gat ctt tcc gga ttg aag cga ccg aaa act aaa att atg ctg aat ttg     1488
Asp Leu Ser Gly Leu Lys Arg Pro Lys Thr Lys Ile Met Leu Asn Leu
                485                 490                 495 ggc aat ccg gaa ttg gca ttc aaa ctc agc ttt ttg ccg aat gac ggc     1536
Gly Asn Pro Glu Leu Ala Phe Lys Leu Ser Phe Leu Pro Asn Asp Gly
        500                 505                 510 gtc gga ttg gcg cgg atg gaa ttc atc att acc gag ttt atc aag gct     1584
Val Gly Leu Ala Arg Met Glu Phe Ile Ile Thr Glu Phe Ile Lys Ala
    515                 520                 525 cat ccg atg gcg ttg att cat cct gaa cgc ata caa gat gcc gaa gaa     1632
His Pro Met Ala Leu Ile His Pro Glu Arg Ile Gln Asp Ala Glu Glu
530                 535                 540 aaa gca aag att aaa cgc ttg acc cgc tat tat gcg cag ccg gag gat     1680
Lys Ala Lys Ile Lys Arg Leu Thr Arg Tyr Tyr Ala Gln Pro Glu Asp
545                 550                 555                 560 ttt ttc atc gag cgt ctt gcg gag gga gtc ggt acg atc gct gca gcg     1728
Phe Phe Ile Glu Arg Leu Ala Glu Gly Val Gly Thr Ile Ala Ala Ala
                565                 570                 575 ttt tat ccg aag ccg gtc gtg gtc aga atg tcc gac ttc aag act aat     1776
Phe Tyr Pro Lys Pro Val Val Val Arg Met Ser Asp Phe Lys Thr Asn
        580                 585                 590
```

```
gag tat gca acc ttg ctc ggc ggt cgc ggg ttc gag cgc gac gag gcg    1824
Glu Tyr Ala Thr Leu Leu Gly Gly Arg Gly Phe Glu Arg Asp Glu Ala
        595                 600                 605 aat ccg atg atc ggt ttc aga ggc gct tcg cgt tat gtg cat ccc gat    1872
Asn Pro Met Ile Gly Phe Arg Gly Ala Ser Arg Tyr Val His Pro Asp
610                 615                 620 tat aag gaa ggc ttc gca ctc gaa tgc cga gcg atg aag cgg gtt cgc    1920
Tyr Lys Glu Gly Phe Ala Leu Glu Cys Arg Ala Met Lys Arg Val Arg
625                 630                 635                 640 gaa gac atg ggt ttg acc aac gtg att ctt atg att ccg ttt tgc cgc    1968
Glu Asp Met Gly Leu Thr Asn Val Ile Leu Met Ile Pro Phe Cys Arg
                645                 650                 655 cgg gag caa gaa gcg gtg cgc gtt ttg gat tat atg gcc gag ctc ggt    2016
Arg Glu Gln Glu Ala Val Arg Val Leu Asp Tyr Met Ala Glu Leu Gly
            660                 665                 670 ttg aaa aga ggg gag aac gga ctc gaa att tat gtg atg tgc gaa att    2064
Leu Lys Arg Gly Glu Asn Gly Leu Glu Ile Tyr Val Met Cys Glu Ile
        675                 680                 685 ccg aat aat gtg att cgt atc gat gcg ttt tcg aag ctg ttc gac gga    2112
Pro Asn Asn Val Ile Arg Ile Asp Ala Phe Ser Lys Leu Phe Asp Gly
690                 695                 700 ttt tcg atc ggc tcg aac gat ttg aca caa ttg acg ctc ggc gtc gat    2160
Phe Ser Ile Gly Ser Asn Asp Leu Thr Gln Leu Thr Leu Gly Val Asp
705                 710                 715                 720 agg gat tcc gaa ata ctt gcc gaa gat ttc gat gag cgc gat ccg ggc    2208
Arg Asp Ser Glu Ile Leu Ala Glu Asp Phe Asp Glu Arg Asp Pro Gly
                725                 730                 735 gtt aaa gaa atg att cgt atg gct gtg gaa ggc gcg cgc cgt aac ggc    2256
Val Lys Glu Met Ile Arg Met Ala Val Glu Gly Ala Arg Arg Asn Gly
            740                 745                 750 aag cat tcc ggc ttg tgc ggg cag gcg cca tcc gat tat ccg gaa atg    2304
Lys His Ser Gly Leu Cys Gly Gln Ala Pro Ser Asp Tyr Pro Glu Met
        755                 760                 765 gcc gaa tac cta gtc gaa att ggc atc gat tcg atg agt ttg aat ccg    2352
Ala Glu Tyr Leu Val Glu Ile Gly Ile Asp Ser Met Ser Leu Asn Pro
770                 775                 780 gat acg gtg ttg cag acg acc cag cgg att ttg aaa atg gaa gaa caa    2400
Asp Thr Val Leu Gln Thr Thr Gln Arg Ile Leu Lys Met Glu Glu Gln
785                 790                 795                 800 tta aaa ggg                                                        2409
Leu Lys Gly <210> SEQ ID NO 38
<211> LENGTH: 803
<212> TYPE: PRT
<213> ORGANISM: Methylomicrobium alcaliphilum

<400> SEQUENCE: 38

Met Ser Glu Lys Phe Lys Tyr Ile Arg Trp Phe Glu Glu Leu Thr Ile
1               5                   10                  15

Asp Asp Ile Pro Leu Val Gly Gly Lys Asn Ala Ser Leu Gly Glu Met
                20                  25                  30

Tyr Leu Glu Leu Ala Thr Glu Gly Ile Arg Val Pro Asn Gly Phe Ala
            35                  40                  45

Ile Thr Ala Glu Gly Tyr Arg His Met Leu Asp Lys Ala Asp Ala Trp
        50                  55                  60

Glu Ala Leu His Glu Ala Leu Asp Thr Leu Asn Pro Asp Asp Val Asn
65                  70                  75                  80

Asp Leu Ala Lys Arg Ala Arg Lys Ala Arg Asp Ile Val Tyr Ala Ala
                85                  90                  95
```

Pro Leu Ser Glu Asp Leu Glu His Glu Ile Leu Ile Ala Phe Asp Gln
              100                 105                 110

Leu Gln Arg Gln Tyr Asp Glu Leu Thr Val Ala Val Arg Ser Ser
        115                 120                 125

Ala Thr Ala Glu Asp Leu Pro Thr Ala Ser Phe Ala Gly Gln Gln Asp
130                 135                 140

Thr Tyr Leu Asn Val His Ser Gly Gln Ala Leu Leu Asp Ala Cys Lys
145                 150                 155                 160

Arg Cys Phe Ala Ser Leu Phe Thr Asp Arg Ala Ile His Tyr Arg Ile
                165                 170                 175

Asp Gln Gly Phe Asp His Phe Lys Val Ser Leu Ser Ile Gly Val Met
            180                 185                 190

Lys Met Val Arg Ser Asp Leu Ala Ser Ser Gly Val Met Phe Ser Ile
            195                 200                 205

Asp Thr Glu Ser Gly Phe Lys Asp Ala Val Phe Ile Thr Gly Ala Tyr
    210                 215                 220

Gly Leu Gly Glu Asn Val Val Gln Gly Ser Val Asp Pro Asp Glu Phe
225                 230                 235                 240

Tyr Val His Lys Pro Thr Phe Glu Gln Gly His Arg Cys Val Leu Arg
                245                 250                 255

Arg Ser Leu Gly Ala Lys Lys Ile Lys Met Val Tyr Ser Glu Gly Arg
            260                 265                 270

Thr Arg Glu Gln Thr Cys Asn Val Val Thr Ser Ala Glu Glu Arg Ser
    275                 280                 285

Gln Phe Cys Leu Ser Asp Asp Glu Val Leu Thr Leu Ala Asp Tyr Ala
290                 295                 300

Ile Lys Ile Glu Lys His Tyr Ser Ala Lys Ala Gly Met Pro Arg Pro
305                 310                 315                 320

Met Asp Ile Glu Trp Ala Lys Asp Gly Leu Asp Gly Gln Leu Tyr Ile
                325                 330                 335

Val Gln Ala Arg Pro Glu Thr Val Ala Ser Gln Leu Ser Gly Thr Thr
            340                 345                 350

Leu Glu Gln Tyr Glu Leu Lys Gln Lys Ala Glu Ala Ile Val Thr Gly
            355                 360                 365

Arg Ala Val Gly Ser Lys Ile Ala Val Gly Thr Ala His Val Ile Lys
370                 375                 380

Asn Val Ser Gln Leu Asn Thr Phe Lys Pro Gly Glu Val Leu Ile Thr
385                 390                 395                 400

Asp Met Thr Thr Pro Asp Trp Glu Pro Val Met Lys Thr Ala Ala Ala
                405                 410                 415

Ile Val Thr Asn Arg Gly Gly Arg Thr Cys His Ala Ala Ile Ile Ala
            420                 425                 430

Arg Glu Leu Gly Val Pro Ala Val Ile Gly Cys Asp Asn Ala Thr Glu
        435                 440                 445

Thr Ile Lys Thr Gly Thr Thr Val Thr Val Ser Cys Ala Glu Gly Asp
    450                 455                 460

Ala Gly Lys Val Tyr Asp Gly Glu Leu Ser Phe Asp Val Asn Lys Thr
465                 470                 475                 480

Asp Leu Ser Gly Leu Lys Arg Pro Lys Thr Lys Ile Met Leu Asn Leu
                485                 490                 495

Gly Asn Pro Glu Leu Ala Phe Lys Leu Ser Phe Leu Pro Asn Asp Gly
            500                 505                 510

-continued

```
Val Gly Leu Ala Arg Met Glu Phe Ile Ile Thr Glu Phe Ile Lys Ala
            515                 520                 525

His Pro Met Ala Leu Ile His Pro Glu Arg Ile Gln Asp Ala Glu Glu
        530                 535                 540

Lys Ala Lys Ile Lys Arg Leu Thr Arg Tyr Tyr Ala Gln Pro Glu Asp
545                 550                 555                 560

Phe Phe Ile Glu Arg Leu Ala Glu Gly Val Gly Thr Ile Ala Ala Ala
                565                 570                 575

Phe Tyr Pro Lys Pro Val Val Arg Met Ser Asp Phe Lys Thr Asn
                580                 585                 590

Glu Tyr Ala Thr Leu Leu Gly Gly Arg Gly Phe Glu Arg Asp Glu Ala
        595                 600                 605

Asn Pro Met Ile Gly Phe Arg Gly Ala Ser Arg Tyr Val His Pro Asp
        610                 615                 620

Tyr Lys Glu Gly Phe Ala Leu Glu Cys Arg Ala Met Lys Arg Val Arg
625                 630                 635                 640

Glu Asp Met Gly Leu Thr Asn Val Ile Leu Met Ile Pro Phe Cys Arg
                645                 650                 655

Arg Glu Gln Glu Ala Val Arg Val Leu Asp Tyr Met Ala Glu Leu Gly
                660                 665                 670

Leu Lys Arg Gly Glu Asn Gly Leu Glu Ile Tyr Val Met Cys Glu Ile
        675                 680                 685

Pro Asn Asn Val Ile Arg Ile Asp Ala Phe Ser Lys Leu Phe Asp Gly
        690                 695                 700

Phe Ser Ile Gly Ser Asn Asp Leu Thr Gln Leu Thr Leu Gly Val Asp
705                 710                 715                 720

Arg Asp Ser Glu Ile Leu Ala Glu Asp Phe Asp Glu Arg Asp Pro Gly
                725                 730                 735

Val Lys Glu Met Ile Arg Met Ala Val Glu Gly Ala Arg Arg Asn Gly
                740                 745                 750

Lys His Ser Gly Leu Cys Gly Gln Ala Pro Ser Asp Tyr Pro Glu Met
        755                 760                 765

Ala Glu Tyr Leu Val Glu Ile Gly Ile Asp Ser Met Ser Leu Asn Pro
770                 775                 780

Asp Thr Val Leu Gln Thr Thr Gln Arg Ile Leu Lys Met Glu Glu Gln
785                 790                 795                 800

Leu Lys Gly

<210> SEQ ID NO 39
<211> LENGTH: 2010
<212> TYPE: DNA
<213> ORGANISM: Methylomicrobium alcaliphilum
<220> FEATURE:
<221> NAME/KEY: CDS
<222> LOCATION: (1)..(2010)

<400> SEQUENCE: 39 atg cct tcg cgc cga gac tta gcg aac gcc ata cgc gct ttg agc atg      48
Met Pro Ser Arg Arg Asp Leu Ala Asn Ala Ile Arg Ala Leu Ser Met
1               5                   10                  15 gat gcc gtc caa aaa gcc aac tcc gga cac ccg ggc gca ccg atg ggg      96
Asp Ala Val Gln Lys Ala Asn Ser Gly His Pro Gly Ala Pro Met Gly
                20                  25                  30 atg gcg gat atc gcc gag gtg tta tgg aac gac ttc ctg cag cat aac     144
Met Ala Asp Ile Ala Glu Val Leu Trp Asn Asp Phe Leu Gln His Asn
            35                  40                  45
```

```
ccg act aac ccg aac tgg gcc aac cga gac cgc ttc gta ctg tct aac      192
Pro Thr Asn Pro Asn Trp Ala Asn Arg Asp Arg Phe Val Leu Ser Asn
    50              55              60 ggc cac ggc tcg atg ctg ctg tac tcg tta ctg cat ctg aca ggt tac      240
Gly His Gly Ser Met Leu Leu Tyr Ser Leu Leu His Leu Thr Gly Tyr
65              70              75              80 cag ctg ccg atc gac gaa ctg aaa caa ttc cgt caa ctg cat tca aaa      288
Gln Leu Pro Ile Asp Glu Leu Lys Gln Phe Arg Gln Leu His Ser Lys
                85              90              95 acc ccg ggt cat ccg gaa tac ggc tat gcg ccg ggc gtc gaa acg acg      336
Thr Pro Gly His Pro Glu Tyr Gly Tyr Ala Pro Gly Val Glu Thr Thr
            100             105             110 acc gga cca tta ggt caa ggc atc acc aat gcc gtg ggc ttt gcg ata      384
Thr Gly Pro Leu Gly Gln Gly Ile Thr Asn Ala Val Gly Phe Ala Ile
        115             120             125 gcc gaa cgc gca cta gcg ggt caa ttt aac cgt ccc gga cac gaa atc      432
Ala Glu Arg Ala Leu Ala Gly Gln Phe Asn Arg Pro Gly His Glu Ile
    130             135             140 gtc gac cat tac acc tac gcc ttc ctg ggc gac ggc tgt tta atg gaa      480
Val Asp His Tyr Thr Tyr Ala Phe Leu Gly Asp Gly Cys Leu Met Glu
145             150             155             160 ggc atc tcg cat gaa gcc tgc tca ttg gcc ggc tcg atg aaa ctg ggc      528
Gly Ile Ser His Glu Ala Cys Ser Leu Ala Gly Ser Met Lys Leu Gly
                165             170             175 aaa ctg att gcc gtc tac gac gac aac aac atc tcg atc gac ggc gaa      576
Lys Leu Ile Ala Val Tyr Asp Asp Asn Asn Ile Ser Ile Asp Gly Glu
            180             185             190 gtc cgc ggt cac ggc gac acg ccg ggc tgg ttc ctg gac gac acg ccg      624
Val Arg Gly His Gly Asp Thr Pro Gly Trp Phe Leu Asp Asp Thr Pro
        195             200             205 aaa cgc ttc gaa gcc tac ggc tgg cac gtc atc ccg aaa gta gac ggc      672
Lys Arg Phe Glu Ala Tyr Gly Trp His Val Ile Pro Lys Val Asp Gly
    210             215             220 cat aac cct gaa gcc gtc aaa aaa gcc ttg gaa gaa gcg cgt agc gtc      720
His Asn Pro Glu Ala Val Lys Lys Ala Leu Glu Glu Ala Arg Ser Val
225             230             235             240 act gat cgg ccg acc ttg atc tgc tgc caa acc atc att ggc tgg ggc      768
Thr Asp Arg Pro Thr Leu Ile Cys Cys Gln Thr Ile Ile Gly Trp Gly
                245             250             255 tcg ccg aat aaa gaa ggc aaa gaa gaa tgt cat gga gcg gca tta ggc      816
Ser Pro Asn Lys Glu Gly Lys Glu Glu Cys His Gly Ala Ala Leu Gly
            260             265             270 gaa gcc gaa atc acg gca acc cgc gaa cgc atc ggt tgg ccg cat gca      864
Glu Ala Glu Ile Thr Ala Thr Arg Glu Arg Ile Gly Trp Pro His Ala
        275             280             285 cct ttc gaa atc ccg gcg gat att tac gcg ggt tgg gat gcg aaa gac      912
Pro Phe Glu Ile Pro Ala Asp Ile Tyr Ala Gly Trp Asp Ala Lys Asp
    290             295             300 aaa ggc gcg cgt caa gaa gcg gag tgg aac gac aaa ttc gcg aaa tac      960
Lys Gly Ala Arg Gln Glu Ala Glu Trp Asn Asp Lys Phe Ala Lys Tyr
305             310             315             320 caa gca gcg cat ccg gaa ctg gcg gcc gaa ttc gaa cgc cgc atg agc      1008
Gln Ala Ala His Pro Glu Leu Ala Ala Glu Phe Glu Arg Arg Met Ser
                325             330             335 gga cag ctg ccg agc gac tgg tcg gaa aaa gcg aac gcc ttc att gct      1056
Gly Gln Leu Pro Ser Asp Trp Ser Glu Lys Ala Asn Ala Phe Ile Ala
            340             345             350 gcg gtc gac gca aaa ggc gaa acc atc gct agc cgc aaa gcc tca caa      1104
Ala Val Asp Ala Lys Gly Glu Thr Ile Ala Ser Arg Lys Ala Ser Gln
        355             360             365
```

```
aac acc ctg aac gga ttc gga ccg tta ctg ccc gaa ctg atg ggc ggc    1152
Asn Thr Leu Asn Gly Phe Gly Pro Leu Leu Pro Glu Leu Met Gly Gly
    370             375                 380 tcg gcg gac ttg gca ggc tcc aac ttg acc ctg tgg tcg ggt tgc aaa    1200
Ser Ala Asp Leu Ala Gly Ser Asn Leu Thr Leu Trp Ser Gly Cys Lys
385                 390                 395                 400 gac gtc aac gcc ccg gga cat gac ggc aac tac gtc tac tac ggc gtc    1248
Asp Val Asn Ala Pro Gly His Asp Gly Asn Tyr Val Tyr Tyr Gly Val
                405                 410                 415 cgt gaa ttc ggc atg tcg gcg atc atg aac ggc atc acc ctg cat ggc    1296
Arg Glu Phe Gly Met Ser Ala Ile Met Asn Gly Ile Thr Leu His Gly
                    420                 425                 430 ggc ttc aag ccg tac ggc gcg acc ttc ctg atg ttc tcc gaa tat gcg    1344
Gly Phe Lys Pro Tyr Gly Ala Thr Phe Leu Met Phe Ser Glu Tyr Ala
            435                 440                 445 cgg aat gcc ttg cgg atg gcg tcg ttg atg aaa atc ccg acc atc ttc    1392
Arg Asn Ala Leu Arg Met Ala Ser Leu Met Lys Ile Pro Thr Ile Phe
        450                 455                 460 gta tac acg cac gac tcg atc ggc tta ggc gaa gac ggc ccg acc cat    1440
Val Tyr Thr His Asp Ser Ile Gly Leu Gly Glu Asp Gly Pro Thr His
465                 470                 475                 480 caa ccg atc gaa caa acc gcg acc ttg cgg atg att cca aac atg caa    1488
Gln Pro Ile Glu Gln Thr Ala Thr Leu Arg Met Ile Pro Asn Met Gln
                485                 490                 495 gtg tgg cgt cca tgt gat gct gtg gaa tcg gcg gtg tcg tgg aaa gcg    1536
Val Trp Arg Pro Cys Asp Ala Val Glu Ser Ala Val Ser Trp Lys Ala
                    500                 505                 510 gcg att gaa cga aac gat gga ccg agt tgt ctg atc ttc tca cgg caa    1584
Ala Ile Glu Arg Asn Asp Gly Pro Ser Cys Leu Ile Phe Ser Arg Gln
            515                 520                 525 aac cta gcg cac att gcg cgg acg ccg gcg cag atc gaa gcg atc aac    1632
Asn Leu Ala His Ile Ala Arg Thr Pro Ala Gln Ile Glu Ala Ile Asn
        530                 535                 540 aaa ggc ggc tac att ctg aaa gac agc gaa ggt cag ccg gac gtg atc    1680
Lys Gly Gly Tyr Ile Leu Lys Asp Ser Glu Gly Gln Pro Asp Val Ile
545                 550                 555                 560 ctg att gcg acg ggc tcg gaa gtc gaa ttg gcg gtg aaa gcg gca gac    1728
Leu Ile Ala Thr Gly Ser Glu Val Glu Leu Ala Val Lys Ala Ala Asp
                565                 570                 575 gag ttg agc ggc aaa ggc aaa aaa gtg cgg gtc gtc tcg atg cca tcg    1776
Glu Leu Ser Gly Lys Gly Lys Lys Val Arg Val Val Ser Met Pro Ser
                    580                 585                 590 acc aac gta ttc gat gcg cag gac gaa gcc tac cgt gag tcg gtg ctg    1824
Thr Asn Val Phe Asp Ala Gln Asp Glu Ala Tyr Arg Glu Ser Val Leu
            595                 600                 605 ccg tca tcg gtg aca aaa cgc gtc gta att gaa gcg ggc gtg acc gac    1872
Pro Ser Ser Val Thr Lys Arg Val Val Ile Glu Ala Gly Val Thr Asp
        610                 615                 620 agc tgg tgg aaa tac gcg ggt aca caa ggt tgc gtc atc gga atg gat    1920
Ser Trp Trp Lys Tyr Ala Gly Thr Gln Gly Cys Val Ile Gly Met Asp
625                 630                 635                 640 cgt ttc ggc gaa tcg gca ccg gcc ggc gcg ctg ttc aaa gag ttc ggc    1968
Arg Phe Gly Glu Ser Ala Pro Ala Gly Ala Leu Phe Lys Glu Phe Gly
                645                 650                 655
```

| ttc | acc | gtt | gac | aat | gtc | gtc | aaa | cac | gtc | gaa | gct | ctg | ctt | | 2010 |
| Phe | Thr | Val | Asp | Asn | Val | Val | Lys | His | Val | Glu | Ala | Leu | Leu | | |
| | | | 660 | | | | 665 | | | | | 670 | | | |

<210> SEQ ID NO 40
<211> LENGTH: 670
<212> TYPE: PRT
<213> ORGANISM: Methylomicrobium alcaliphilum

<400> SEQUENCE: 40

| Met | Pro | Ser | Arg | Arg | Asp | Leu | Ala | Asn | Ala | Ile | Arg | Ala | Leu | Ser | Met |
|---|---|---|---|---|---|---|---|---|---|---|---|---|---|---|---|
| 1 | | | | 5 | | | | | 10 | | | | | 15 | |

| Asp | Ala | Val | Gln | Lys | Ala | Asn | Ser | Gly | His | Pro | Gly | Ala | Pro | Met | Gly |
| | | | 20 | | | | | 25 | | | | | 30 | | |

| Met | Ala | Asp | Ile | Ala | Glu | Val | Leu | Trp | Asn | Asp | Phe | Leu | Gln | His | Asn |
| | | 35 | | | | | 40 | | | | | 45 | | | |

| Pro | Thr | Asn | Pro | Asn | Trp | Ala | Asn | Arg | Asp | Arg | Phe | Val | Leu | Ser | Asn |
| | 50 | | | | | 55 | | | | | 60 | | | | |

| Gly | His | Gly | Ser | Met | Leu | Leu | Tyr | Ser | Leu | Leu | His | Leu | Thr | Gly | Tyr |
| 65 | | | | | 70 | | | | | 75 | | | | | 80 |

| Gln | Leu | Pro | Ile | Asp | Glu | Leu | Lys | Gln | Phe | Arg | Gln | Leu | His | Ser | Lys |
| | | | | 85 | | | | | 90 | | | | | 95 | |

| Thr | Pro | Gly | His | Pro | Glu | Tyr | Gly | Tyr | Ala | Pro | Gly | Val | Glu | Thr | Thr |
| | | | 100 | | | | | 105 | | | | | 110 | | |

| Thr | Gly | Pro | Leu | Gly | Gln | Gly | Ile | Thr | Asn | Ala | Val | Gly | Phe | Ala | Ile |
| | | | 115 | | | | | 120 | | | | | 125 | | |

| Ala | Glu | Arg | Ala | Leu | Ala | Gly | Gln | Phe | Asn | Arg | Pro | Gly | His | Glu | Ile |
| 130 | | | | | 135 | | | | | 140 | | | | | |

| Val | Asp | His | Tyr | Thr | Tyr | Ala | Phe | Leu | Gly | Asp | Gly | Cys | Leu | Met | Glu |
| 145 | | | | | 150 | | | | | 155 | | | | | 160 |

| Gly | Ile | Ser | His | Glu | Ala | Cys | Ser | Leu | Ala | Gly | Ser | Met | Lys | Leu | Gly |
| | | | | 165 | | | | | 170 | | | | | 175 | |

| Lys | Leu | Ile | Ala | Val | Tyr | Asp | Asp | Asn | Asn | Ile | Ser | Ile | Asp | Gly | Glu |
| | | | 180 | | | | | 185 | | | | | 190 | | |

| Val | Arg | Gly | His | Gly | Asp | Thr | Pro | Gly | Trp | Phe | Leu | Asp | Asp | Thr | Pro |
| | | 195 | | | | | 200 | | | | | 205 | | | |

| Lys | Arg | Phe | Glu | Ala | Tyr | Gly | Trp | His | Val | Ile | Pro | Lys | Val | Asp | Gly |
| 210 | | | | | 215 | | | | | 220 | | | | | |

| His | Asn | Pro | Glu | Ala | Val | Lys | Lys | Ala | Leu | Glu | Glu | Ala | Arg | Ser | Val |
| 225 | | | | | 230 | | | | | 235 | | | | | 240 |

| Thr | Asp | Arg | Pro | Thr | Leu | Ile | Cys | Cys | Gln | Thr | Ile | Ile | Gly | Trp | Gly |
| | | | | 245 | | | | | 250 | | | | | 255 | |

| Ser | Pro | Asn | Lys | Glu | Gly | Lys | Glu | Cys | His | Gly | Ala | Ala | Leu | Gly |
| | | | 260 | | | | | 265 | | | | | 270 | | |

| Glu | Ala | Glu | Ile | Thr | Ala | Thr | Arg | Glu | Arg | Ile | Gly | Trp | Pro | His | Ala |
| | | 275 | | | | | 280 | | | | | 285 | | | |

| Pro | Phe | Glu | Ile | Pro | Ala | Asp | Ile | Tyr | Ala | Gly | Trp | Asp | Ala | Lys | Asp |
| | | 290 | | | | | 295 | | | | | 300 | | | |

| Lys | Gly | Ala | Arg | Gln | Glu | Ala | Glu | Trp | Asn | Asp | Lys | Phe | Ala | Lys | Tyr |
| 305 | | | | | 310 | | | | | 315 | | | | | 320 |

| Gln | Ala | Ala | His | Pro | Glu | Leu | Ala | Ala | Glu | Phe | Glu | Arg | Arg | Met | Ser |
| | | | | 325 | | | | | 330 | | | | | 335 | |

| Gly | Gln | Leu | Pro | Ser | Asp | Trp | Ser | Glu | Lys | Ala | Asn | Ala | Phe | Ile | Ala |
| | | | 340 | | | | | 345 | | | | | 350 | | |

| Ala | Val | Asp | Ala | Lys | Gly | Glu | Thr | Ile | Ala | Ser | Arg | Lys | Ala | Ser | Gln |

-continued

```
                355            360                365
Asn Thr Leu Asn Gly Phe Gly Pro Leu Leu Pro Glu Leu Met Gly Gly
        370            375            380
Ser Ala Asp Leu Ala Gly Ser Asn Leu Thr Leu Trp Ser Gly Cys Lys
385            390            395            400
Asp Val Asn Ala Pro Gly His Asp Gly Asn Tyr Val Tyr Tyr Gly Val
                405            410            415
Arg Glu Phe Gly Met Ser Ala Ile Met Asn Gly Ile Thr Leu His Gly
            420            425            430
Gly Phe Lys Pro Tyr Gly Ala Thr Phe Leu Met Phe Ser Glu Tyr Ala
        435            440            445
Arg Asn Ala Leu Arg Met Ala Ser Leu Met Lys Ile Pro Thr Ile Phe
    450            455            460
Val Tyr Thr His Asp Ser Ile Gly Leu Gly Glu Asp Gly Pro Thr His
465            470            475            480
Gln Pro Ile Glu Gln Thr Ala Thr Leu Arg Met Ile Pro Asn Met Gln
            485            490            495
Val Trp Arg Pro Cys Asp Ala Val Glu Ser Ala Val Ser Trp Lys Ala
        500            505            510
Ala Ile Glu Arg Asn Asp Gly Pro Ser Cys Leu Ile Phe Ser Arg Gln
            515            520            525
Asn Leu Ala His Ile Ala Arg Thr Pro Ala Gln Ile Glu Ala Ile Asn
    530            535            540
Lys Gly Gly Tyr Ile Leu Lys Asp Ser Glu Gly Gln Pro Asp Val Ile
545            550            555            560
Leu Ile Ala Thr Gly Ser Glu Val Glu Leu Ala Val Lys Ala Ala Asp
            565            570            575
Glu Leu Ser Gly Lys Gly Lys Lys Val Arg Val Val Ser Met Pro Ser
            580            585            590
Thr Asn Val Phe Asp Ala Gln Asp Glu Ala Tyr Arg Glu Ser Val Leu
            595            600            605
Pro Ser Ser Val Thr Lys Arg Val Val Ile Glu Ala Gly Val Thr Asp
        610            615            620
Ser Trp Trp Lys Tyr Ala Gly Thr Gln Gly Cys Val Ile Gly Met Asp
625            630            635            640
Arg Phe Gly Glu Ser Ala Pro Ala Gly Ala Leu Phe Lys Glu Phe Gly
            645            650            655
Phe Thr Val Asp Asn Val Val Lys His Val Glu Ala Leu Leu
            660            665            670
```

ORGANIC ACID SYNTHESIS FROM C1 SUBSTRATES

CROSS-REFERENCE TO RELATED APPLICATIONS

This application is a continuation of U.S. Non-provisional application Ser. No. 15/252,648, filed Aug. 31, 2016, which claims priority to, and the benefit of, U.S. Provisional Application No. 62/212,264, filed Aug. 31, 2015, the contents of which are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "15-92_ST25.txt," having a size in bytes of 224 kb and created on Aug. 22, 2016. Pursuant to 37 CFR § 1.52(e)(5), the information contained in the above electronic file is hereby incorporated by reference in its entirety.

BACKGROUND

Methane is a critical component of Earth's carbon cycle that contributes 18% to the Earth's warming. It is the major constituent of natural gas and biogas, composing up to 80% of the latter. $CH_4$ is emitted from a variety of natural and anthropogenic sources. Human-related activities, such as fossil fuel production (e.g., underground coal mining, oil and gas production), agriculture (e.g., enteric fermentation in livestock, manure management, and rice cultivation), landfills, and municipal wastewater are major contributors of global $CH_4$ emission. Anthropogenic $CH_4$ emission accounts for more than 60% of the total $CH_4$ budget (≈300 tg $yr^{-1}$).

$CH_4$ is not only one of the major contributors for climate change, it is also the primary target for near-term climate regulation. Stranded natural gas (SNG), oil-associated gas and almost all waste-derived biogas are not economically feasible sources of energy due to small size or remote location. Each year, up to 116 million tonnes of oil-associated methane and 40 million tonnes of biogas (equivalent to 30% of the total US transportation fuel) are flared, which represents lost energy (five quadrillion BTU of fossil fuel energy), unnecessary greenhouse gas emissions and dangerous air pollution. Strategies for effectively converting $CH_4$ into valuable compounds offer promising new technologies for global warming stabilization and possibly reduction. Methane-rich biogas offers a renewable alternative to fossil natural gas as a feedstock and intermediate in bioprocesses, adding to our capacity for biofuels and biobased products to supplement those available from lignocellulosics or algae.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Provided herein are engineered cells that are able to convert a C1 substrate to an organic acid and that comprise one or more exogenously added genes encoding a 3-dehydroshikimate dehydratase, a protocatechuic acid decarboxylase, a catechol 1,2-dioxygenase, aroG$^{fbr}$, trpE$^{fbr}$, a phosphoenolpyruvate synthase, a transketolase, a phosphoketolase, and/or a RuBisCO polypetide.

In some embodiments, the engineered cells comprise AroZ from *Klebsiella variicola*, AroY from *Enterobacter cloacae*, and/or CatA from *Acinetobacter*.

In various embodiments, the phosphoketolase is PktA or PktB and/or the RuBisCO polypetide is CbbL, CbbS, CbbQ and/or CbbP.

In certain embodiments, the engineered cell is a C1 metabolizing cell, such as cells from the genera *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Candida, Yarrowia, Hansenula, Pichia, Torulopsis, Rhodotorula* or *Pseudomonas*; and/or methanotrophic bacterial cells or a methylotrophic (methanol-utilizing) bacterial or yeast cells.

In some embodiments, the C1 metabolizing cell is a methanotroph or methylotroph; is from an organism from the genus *Methylobacterium, Methylomicrobium*, or *Methylococcus* (such as *Methylobacterium extorquens, Methylobacterium radiotolerans, Methylobacterium populi, Methylobacterium chloromethanicum, Methylobacterium nodulans, Methylomicrobium alkaliphilum* or a combination thereof); or is *M. alkaliphilum* 20Z or *M. buryatense*.

In various embodiments, the C1 substrate is methane, methanol, carbon dioxide, carbon monoxide, syngas, natural gas, or biogas; and/or the organic acid is muconic acid or adipic acid.

Also provided are methods for producing an organic acid by culturing cells described herein with a C1 substrate and recovering the organic acid from the culture.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 shows the nucleic acid sequence (A; SEQ ID NO:1) and amino acid sequence (B; SEQ ID NO:2) of 3-dehydroshikimate dehydratase from *Podospora anserina*.

FIG. 2 shows the nucleic acid sequence (A; SEQ ID NO:11) and amino acid sequence (B; SEQ ID NO:12) of protocatechuic acid decarboxylase from *Enterobacter cloacae*.

FIG. 3 shows the nucleic acid sequence (A; SEQ ID NO:15) and amino acid sequence (B; SEQ ID NO:16) of catechol 1,2-dioxygenase from *Candida albicans*.

Figure 4:
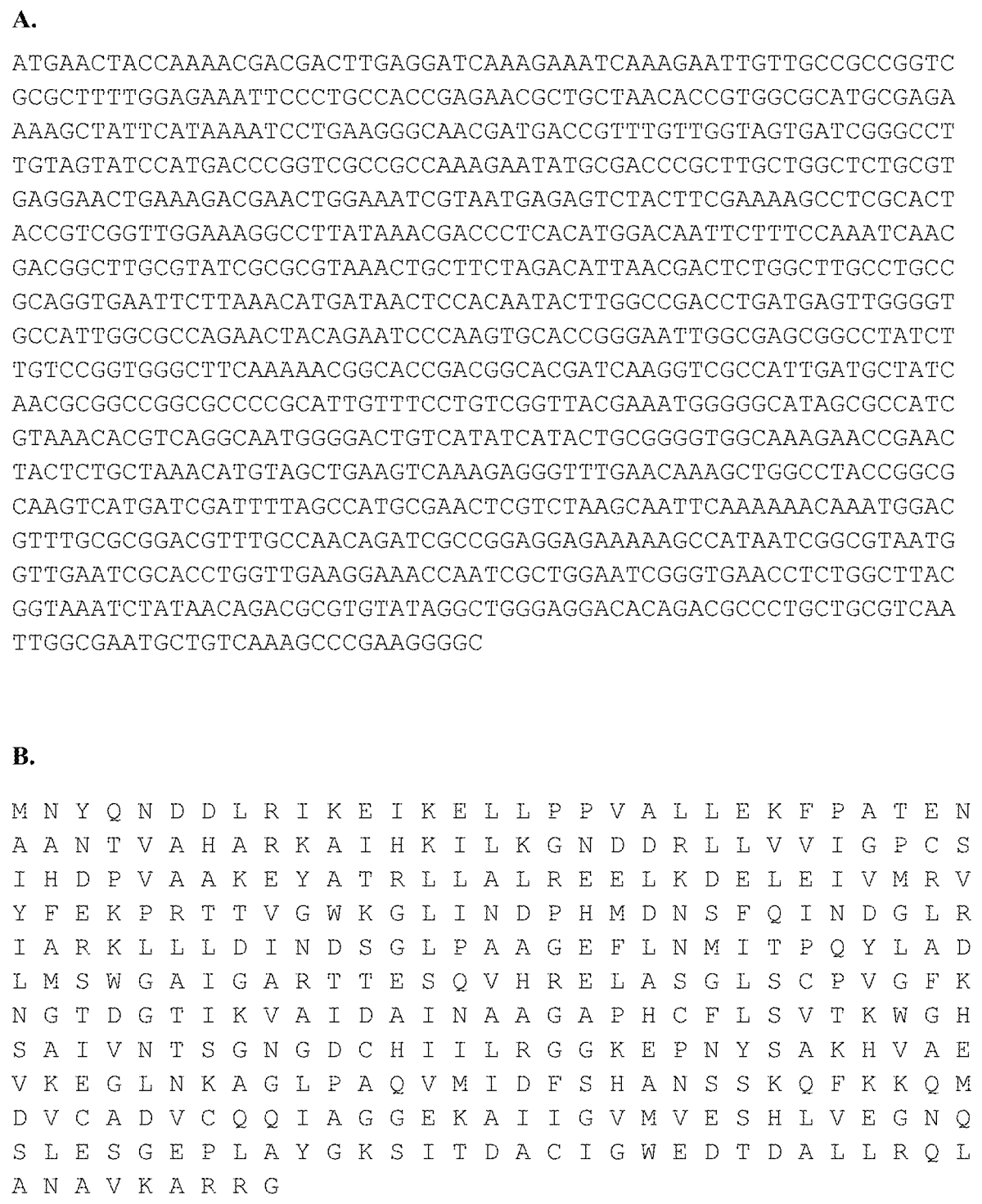

FIG. 4 shows the nucleic acid sequence (A; SEQ ID NO:33) and amino acid sequence (B; SEQ ID NO:34) of aroG$^{fbr}$ from *E. coli* codon optimized for expression in *Methylomicrobium alcaliphilum*.

Figure 5:
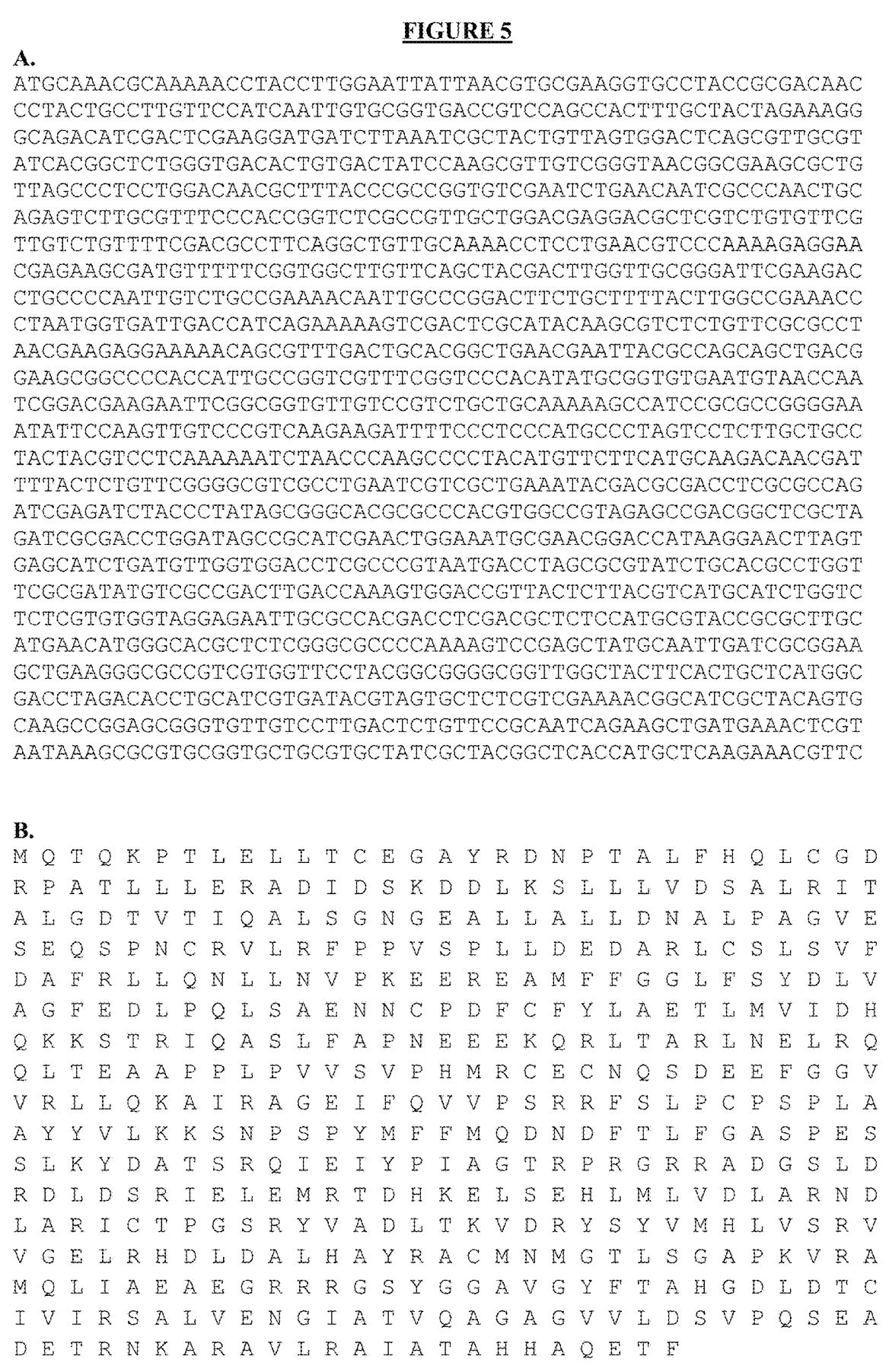

FIG. 5 shows the nucleic acid sequence (A; SEQ ID NO:35) and amino acid sequence (B; SEQ ID NO:36) of trpE$^{fbr}$ from *E. coli* codon optimized for expression in *Methylomicrobium alcaliphilum*.

Figure 6:
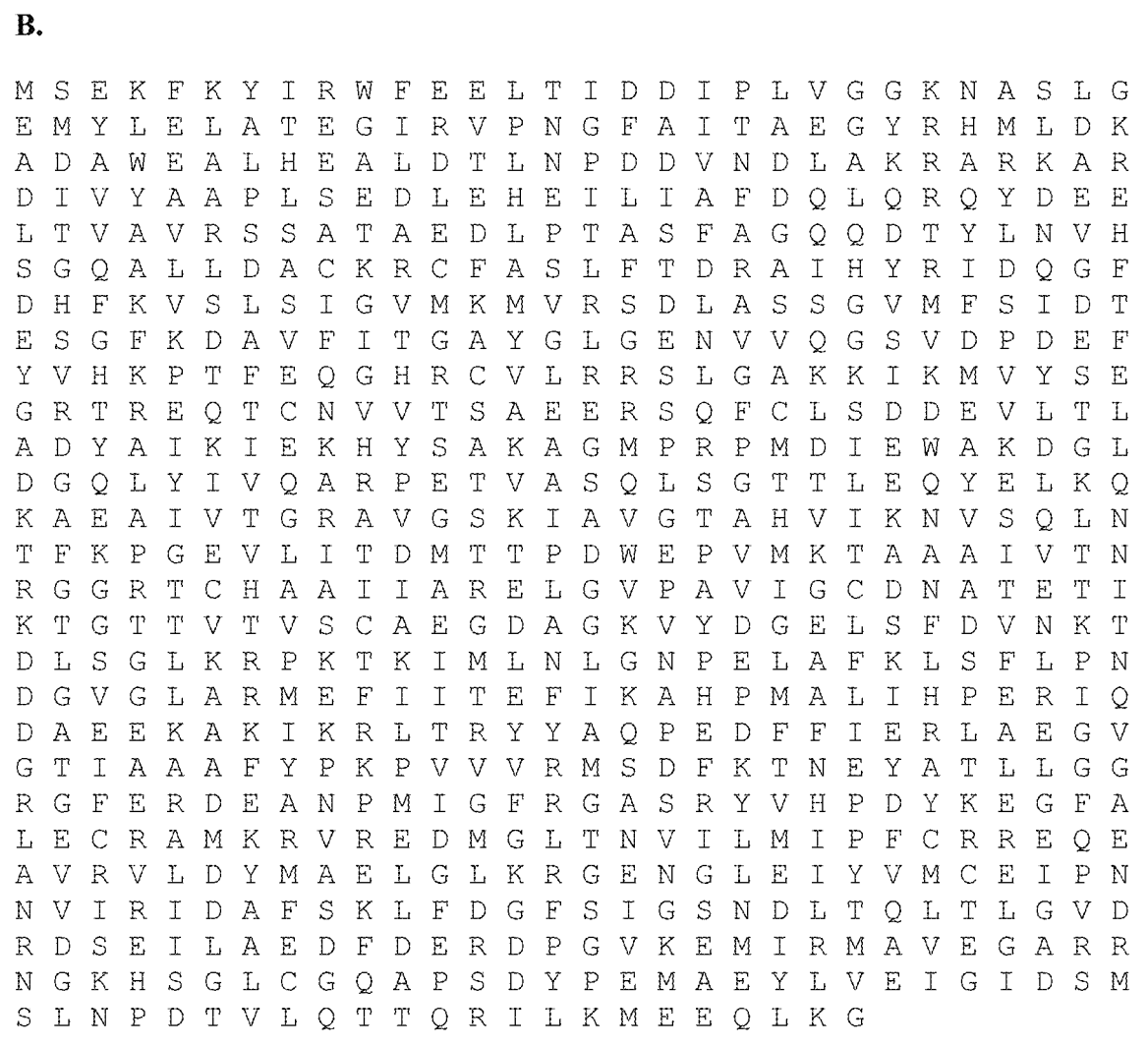

FIG. 6 shows the nucleic acid sequence (A; SEQ ID NO:37) and amino acid sequence (B; SEQ ID NO:38) of phosphoenolpyruvate synthase from *Methylomicrobium alcaliphilum* 20Z.

FIG. 7 shows the nucleic acid sequence (A; SEQ ID NO:39) and amino acid sequence (B; SEQ ID NO:40) of transketolase from *Methylomicrobium alcaliphilum* 20Z.

FIG. 18 shows that Pkt overexpression increases carbon conversion efficiency (CCE) by (A) real-time $CH_4$ consumption (off gas analysis) for wild-type *M. buryatense* cells (WT; upper line) and Pkt-expressing cells (pPKT; lower line); (B) cell growth (DCW, dry cell weight) as measured over time in a 0.5 L gas bioreactor with continuous $CH_4$ feed (20% $CH_4$ in air); and (C) the ratio of biomass DCW to total $CH_4$ consumption after 96 hours.

DETAILED DESCRIPTION

Figure 8:
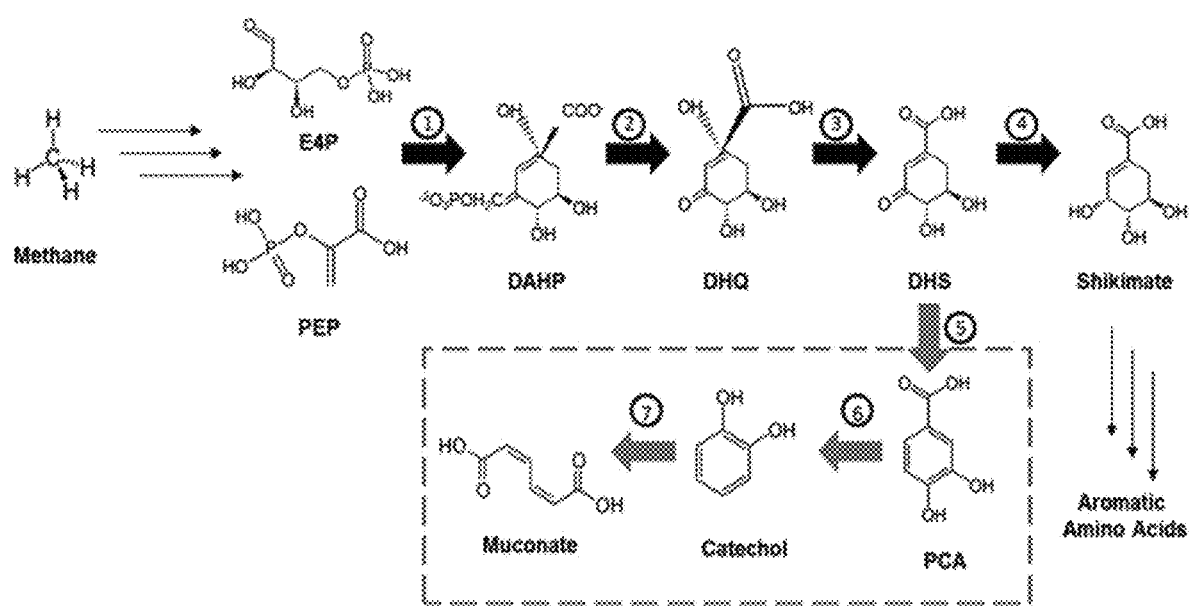
FIG. 8 shows a synthetic pathway for muconate biosynthesis from methane. E4P, erythrose 4-phosphate; PEP, phosphoenolpyruvate; DAHP, 3-deoxy-d-arabino-heptulosonate-7-phosphate; DHQ, 3-dehydroquinate; DHS, 3-dehydroshikimate; (1), DAHP synthase; (2), DHQ synthase; (3), DHQ dehydratase; (4), Shikimate dehydrogenase; (5), 3-dehydroshikimate dehydratase; (6), protocatechuate decarboxylase; (7), catechol 1,2-dioxygenase.
Figure 9:
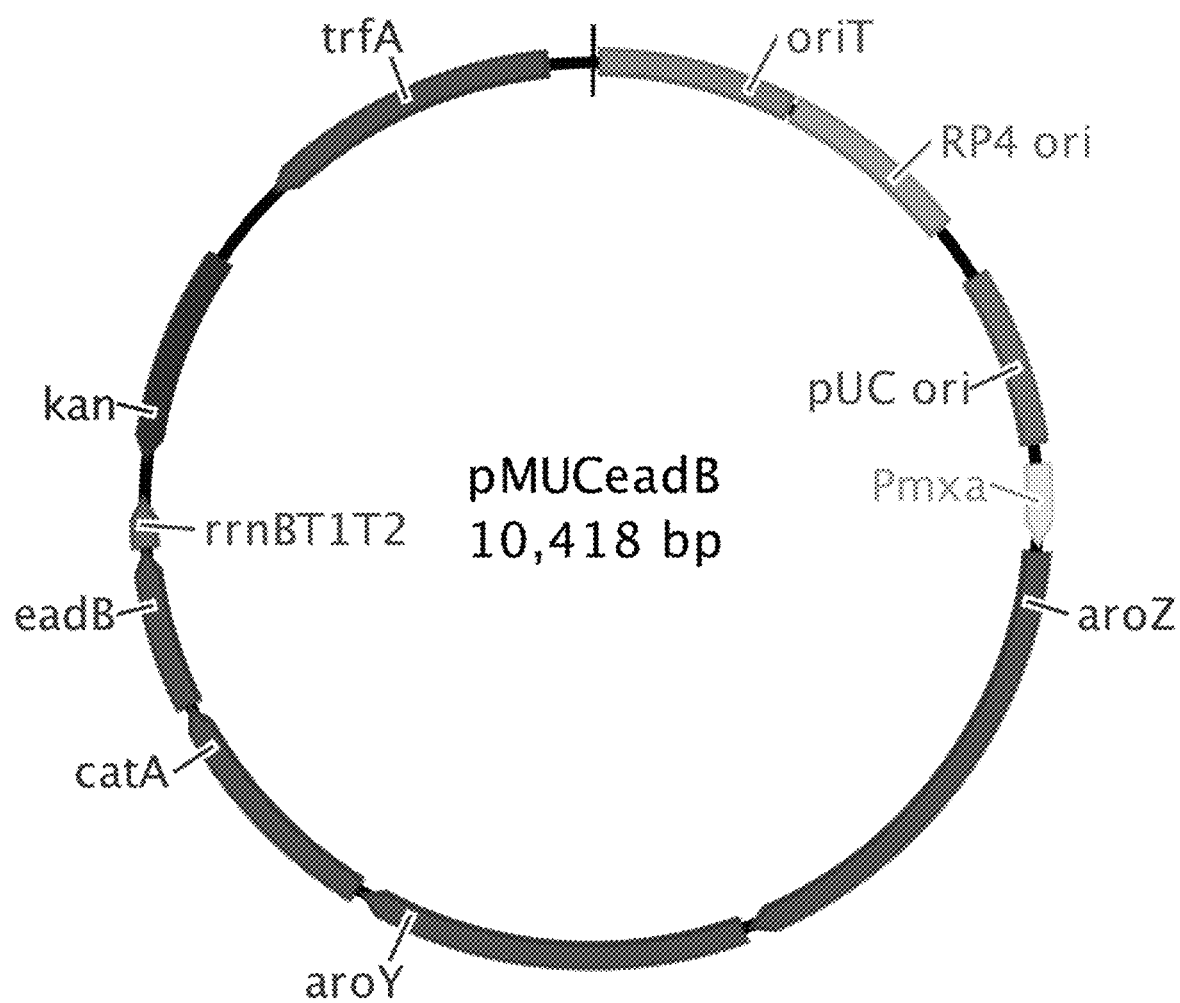
FIG. 9 shows a diagram of a vector useful for constitutive expression of genes such as AroZ, AroY and CatA in *Methylomicrobium alcaliphilum* 20Z.
Figure 10:
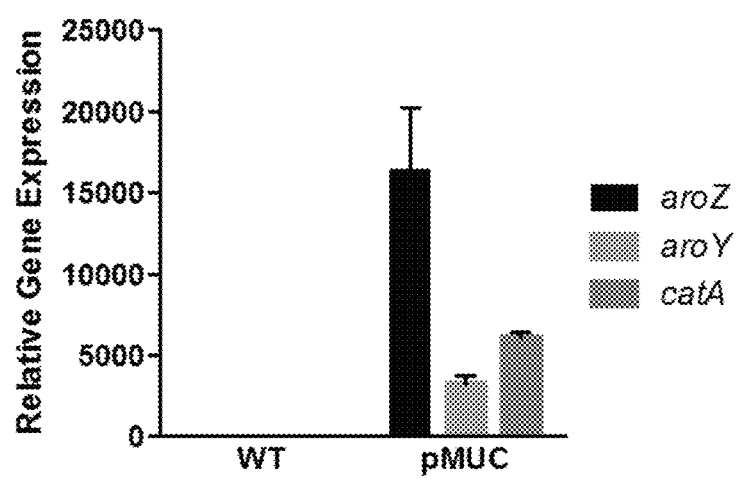
FIG. 10 shows gene expression levels of cells engineered to express 3-dehydroshikimate dehydratase (AroZ), protocatechuic acid decarboxylase (AroY) and catechol 1,2-dioxygenase (CatA).
Figure 11:
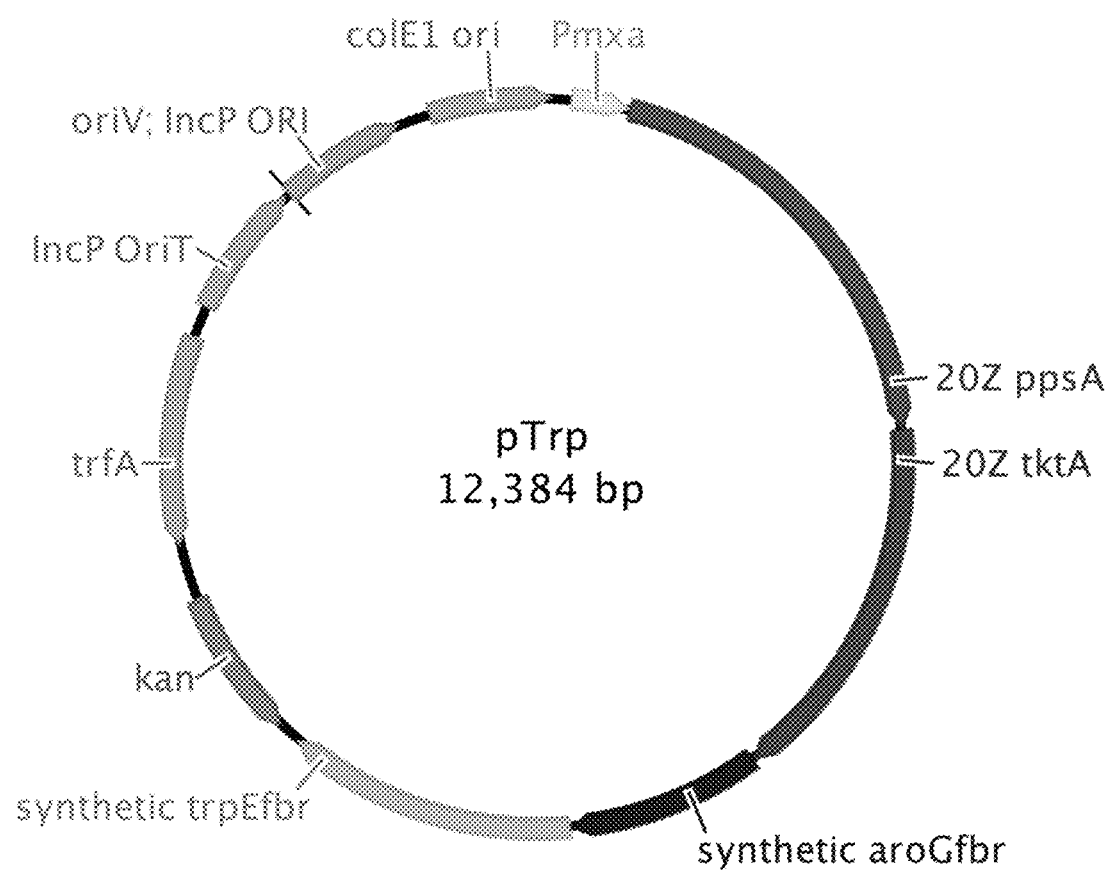
FIG. 11 shows a diagram of a vector for expression of genes for enhanced flux to muconic acid pathway precursors.

Presented herein are methods and biocatalysts for biological conversion of C1 substrates such as methane, methanol, and carbon-dioxide (or materials containing these compounds such as biogas) into organic acids such as muconic acid or adipic acid. Methanotrophs do not natively produce muconic acid, but disclosed herein are processes for altering methanotrophs to enable the production of organic acids such as muconic acid or adipic acid from C1 (e.g., methane) containing sources.

Figure 1:
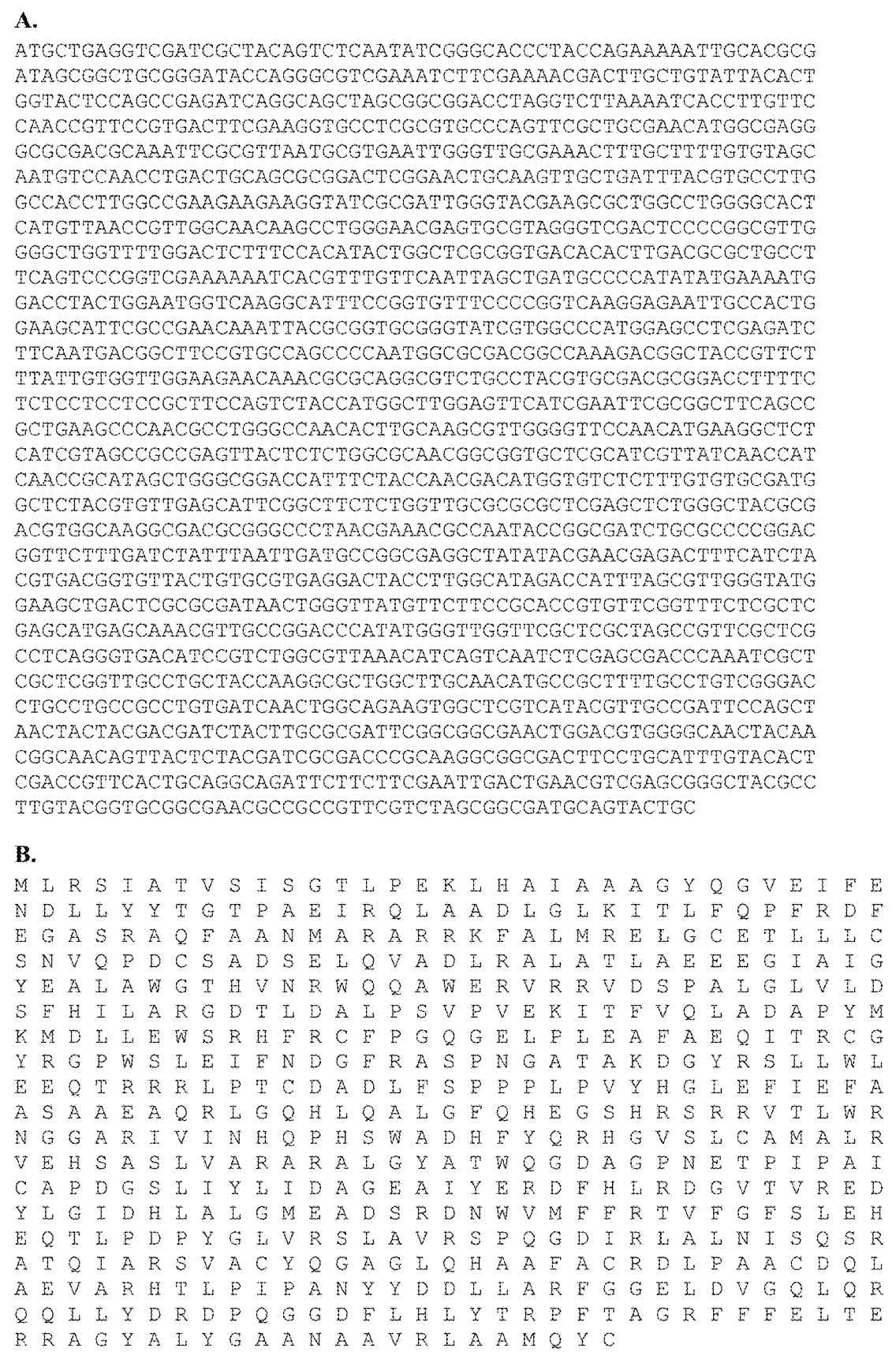
Figure 2:
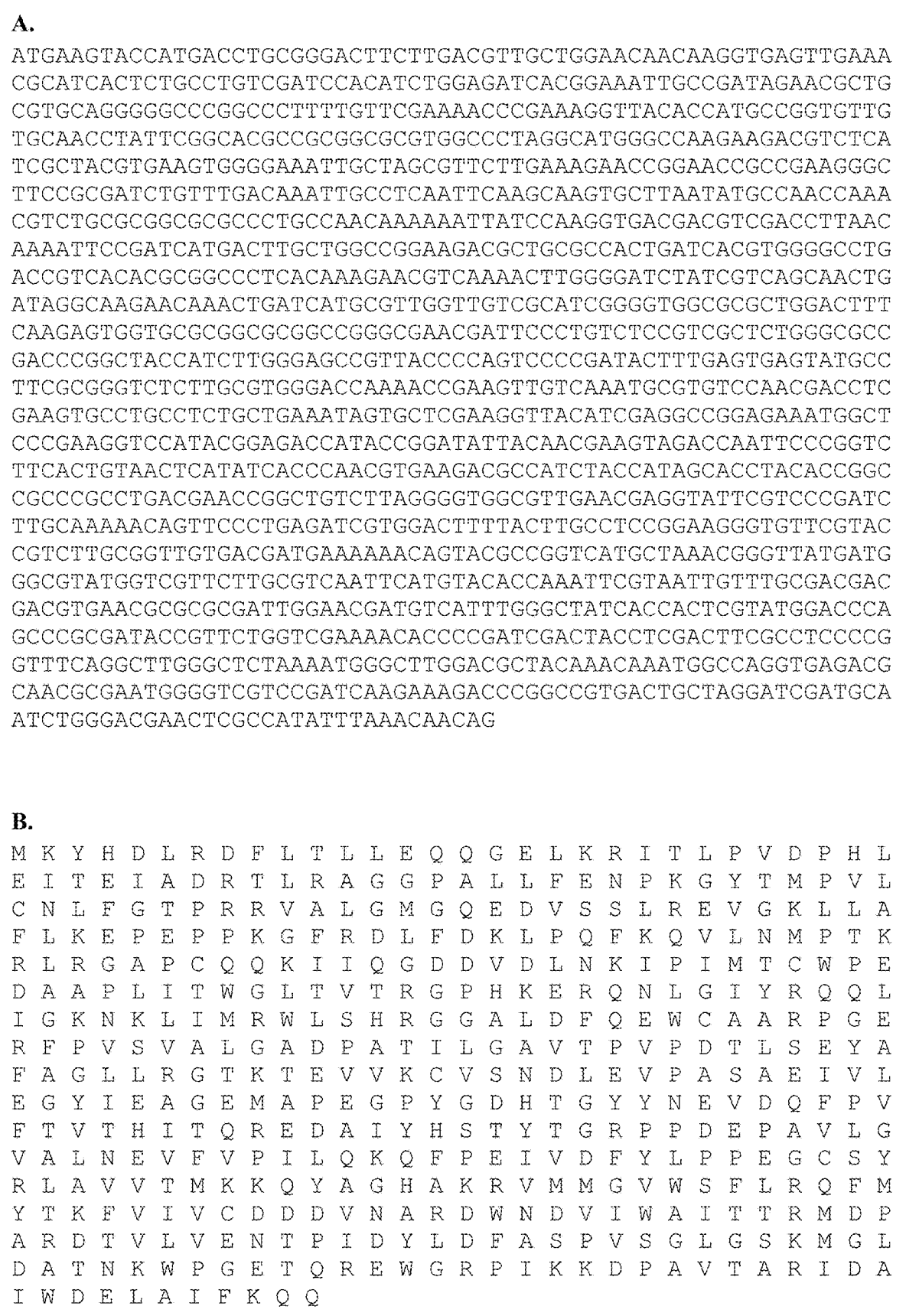

The cells of methanotrophic organisms may be modified to express one or more exogenously added genes encoding enzymes that allow the cell to convert C1 substrates such as methane to muconic acid or adipic acid. Exemplary enzymes include 3-dehydroshikimate dehydratase, protocatechuic acid decarboxylase and catechol 1,2-dioxygenase enzymes. Specific examples include the enzymes 3-dehydroshikimate dehydratase (AroZ) from *Podospora anserina*, protocatechuic acid decarboxylase (AroY) from *Enterobacter cloacae*, and catechol 1,2-dioxygenase (CatA) from *Candida albicans*, the nucleic acid and amino acid sequences of which are provided in FIG. 1-3. Functional homologs of these enzymes from other species are also suitable for use in the present disclosure.

Additional suitable examples of 3-dehydroshikimate dehydratases include those from *Klebsiella variicola* (SEQ ID NOS:3 and 4), *Bacillus thuringiensis* (SEQ ID NOS:5 and 6), *Enterobacter aerogenes* (SEQ ID NOS:7 and 8), and *Acinetobacter baylyi* (SEQ ID NOS:9 and 10). An additional exemplary protocatechuic acid decarboxylase is the AroY gene from *Klebsiella variicola* (SEQ ID NOS:13 and 14). Additional suitable examples of catechol 1,2-dioxygenases include the CatA gene from *Pseudomonas putida* (SEQ ID NOS:19 and 20) and the CatA gene from *Acinetobacter* spp. (SEQ ID NOS:17 and 18) as well as a variant version of this gene where the proline residue at position 76 is mutated to an alanine.

The cells may also be engineered to express one or more exogenously added genes encoding aroG$^{fbr}$, trpE$^{fbr}$, a phosphoenolpyruvate synthase, or a transketolase. The designation "fbr" refers to feedback resistant variants of the indicated enzymes. Suitable examples include aroG$^{fbr}$ from *E. coli*, trpE$^{fbr}$ from *E. coli*, phosphoenolpyruvate synthase from *Methylomicrobium alcaliphilum* 20Z or transketolase from *Methylomicrobium alcaliphilum* 20Z, the nucleic acid and amino acid sequences of which are provided in FIG. 4-7. Functional homologs of these enzymes from other species are also suitable for use in the present disclosure. All nucleic acid sequences may be codon optimized for expression in the host cell.

Muconic acid is a dicarboxylic acid that may be converted via hydrogenation into adipic acid with high yield and specificity. Currently, nylon-6,6 accounts for greater than 85% of global adipic acid production. The dicarboxylic functionality of adipic acid affords a wide variety of upgrading strategies including polymerization, lactonization, diolization, and ketonization. As such, adipic acid can be readily converted to other large-market, high-value molecules and fuel precursors, such as plasticizers, lubricants, engineering resins, polyurethanes, and food gelatin. Additionally, muconic acid itself can be upgraded to produce commodity chemicals beyond adipic acid, including terepthalic and trimellitic acids. Conventional adipic acid production is almost exclusively dependent on petroleum-derived feedstocks and accounts for nearly 10% of global $N_2O$ emissions. Thus, the production of muconic acid or adipic acid through a biocatalytic upgrading process from renewable methane sources offers a novel production route with significant economic and sustainability benefits. Furthermore, the diversity of products that can be made from adipic acid assures a large demand for the heretofore poorly valorized biogas.

Microbial utilization of $CH_4$ (methanotrophy) can occur in both aerobic and anaerobic environments, but only aerobic methanotrophic bacteria (methanotrophs) have been isolated in pure culture. Methanotrophs use methane monooxygenase for the first oxidation step that converts $CH_4$ into methanol ($CH_3OH$), which is further oxidized to formaldehyde ($CH_2O$). Gammaproteobacteria, such as *M. alcaliphilum* 20Z, assimilate formaldehyde through the assimilatory ribulose monophosphate (RuMP) pathway. The first part of the pathway is the condensation of $CH_2O$ with ribulose-5-phosphate (Ru5P) to produce 3-hexulose-6-phosphate, which is subsequently isomerized to fructose-6-phosphate.

Muconic acid production naturally occurs during the catabolism of aromatic compounds in a limited number of microorganisms. Production of muconic acid in various microbes has been achieved by exploiting naturally occurring intermediary metabolic pathways involved in the detoxification or catabolism of aromatic compounds such as toluene and benzoate. Methanotrophs do not naturally possess a pathway to produce muconic acid, and are obligate C1-utilizers. As such, a novel metabolic route to muconic acid biosynthesis must be employed in order to leverage the innate capacity of methanotrophic biocatalysts.

Shunting naturally occurring metabolites toward muconic acid presents a direct approach for synthesizing this product from renewable feedstocks. The shikimate pathway is involved in the synthesis of aromatic amino acids, and muconic acid can be synthesized in a three step process from the 3-dehydroshikimate (DHS) intermediate produced in this pathway (FIG. 8). Alternatively, muconic acid can be generated by converting the anthranilate intermediate of tryptophan biosynthesis into catechol by the anthranilate 1,2 dioxygenase.

*Methylomicrobium* spp. do not require exogenous amino acids for growth, indicating that the up-front metabolic machinery is already in place. Genomic analysis of *M. alcaliphilum* 20Z confirmed all genes of the shikimate and pentose phosphate (non-oxidative, PPP) pathways are present, verifying the ability to produce DHS. Further, the strain has high flux via PPP and a high pool of the key precursors for the proposed route of muconate biosynthesis, highlighting the feasibility of engineering muconate production in the organism.

Synthetic design of a three-step muconate biosynthesis pathway may be established and optimized in bacteria (e.g., *P. putida*) and yeast, using aromatics and glucose as precursors for muconic acid biosynthesis, respectively. Alternatively, muconate biosynthesis may be connected to methane precursors. In one specific example, a three-step synthetic pathway comprised of the enzymes 3-dehydroshikimate dehydratase from *Podospora anserina*, protocatechuic acid decarboxylase from *Enterobacter cloacae*, and catechol 1,2-dioxygenase from *Candida albicans* may be incorporated into *M. alcaliphilum* 20Z. The genes may be codon optimized for 20Z and can be used in the construction of both integrative and replicative plasmids.

Suitable cells include those able to convert a C1 substrate to an organic acid or a C1 metabolizing cell, including methanotrophic bacterial cells or methylotrophic (methanol-utilizing) bacterial or yeast cells. In certain embodiments, the cell is a methanotroph or methylotroph.

Examples include cells from the genera *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Candida, Yarrowia, Hansenula, Pichia, Torulopsis, Rhodotorula* or *Pseudomonas*. Specific examples include cells from *Methylobacterium extorquens, Methylobacterium radiotolerans, Methylobacterium populi, Methylobacterium chloromethanicum, Methylobacterium nodulans, Methylomicrobium buryatense, Methylomicrobium alkaliphilum* or a combination thereof. In some embodiments, the cell is *M. alkaliphilum* 20Z.

In various embodiments, the methanotroph is a *Methylomonas* sp. 16a (ATCC PTA 2402), *Methylosinus trichosporium* (NRRL B-1 1,196), *Methylosinus sporium* (NRRL B-1 1,197), *Methylocystis parvus* (NRRL fil 1, 198), *Methylomonas methanica* (NRRL B-1 1,199), *Methylomonas albus* (NRRL fil 1, 200), *Methylobacter capsulatus* (NRRL B-1 1,201), *Methylobacterium organophilum* (ATCC 27,886), *Methylomonas* sp. AJ-3670 (FERM P-2400), *Methylocella silvestris, Methylacidiphilum infernorum, Methylibium petroleiphilum*, or a combination thereof.

In certain embodiments, the organic acid may be muconic acid or adipic acid. The C1 substrate may be a C1 compound such as methane, methanol, carbon dioxide, or carbon monoxide; or a C1-containing material such as syngas, natural gas, or biogas; or materials comprising any of these compounds or materials. Biogas, such as that generated from anaerobic digestion of waste streams, including wastewater derived from conventional biorefineries, is one example of a versatile, renewable C1-containing material source. Currently, biogas is utilized for on-site heat and energy production or sold into the national grid for minimal compensation. However, microbial conversion of biogas to value-added chemicals using the modified microorganisms disclosed herein offers immense valorization potential.

These biocatalysts hold great promise for the capture and conversion of methane from anaerobic-digestion-derived biogas and other anthropogenic $CH_4$ sources. However, biogas contains more than just methane, with $CO_2$ typically comprising about 40% of biogas streams. A biocatalyst capable of co-utilization and conversion of $CO_2$ and $CH_4$ allows for complete utilization of biogas streams and, in turn, enhanced carbon conversion efficiencies. Such a biocatalyst may also shift the landscape of greenhouse gas mitigation, capture, and conversion pursuits, providing a novel, photosynthesis-independent $CO_2$ biocatalyst.

The biocatalyst microorganisms described herein may be further modified to express or overexpress a ribulose 1,5 bisphosphate carboxylase/oxygenase (RuBisCO) enzyme that can allow autotrophic growth in the presence an energy source such as methane, formate or hydrogen). Both homologous and heterologous overexpression of RuBisCO enzymes may increase $CO_2$ utilization in an array of methanotrophs, including those that do not encode genes that enable autotrophic growth.

Exemplary enzymes include the cbbL, cbbS and cbbQ genes encoding the subunit and regulatory proteins of RuBisCO, along with the phosphoribulokinase-encoding cbbP. For example, the nucleotide and amino acid sequences for cbbL, cbbS, cbbQ and cbbP from *Methylococcus capsulatus* are depicted as SEQ ID NOS:25 and 26 (cbbL); SEQ ID NOS:27 and 28 (cbbS); SEQ ID NOS:29 and 30 (cbbQ); and SEQ ID NOS:31 and 32 (cbbP), respectively. Functional homologs of these enzymes from other species are also suitable for use in the present disclosure.

Figure 15:
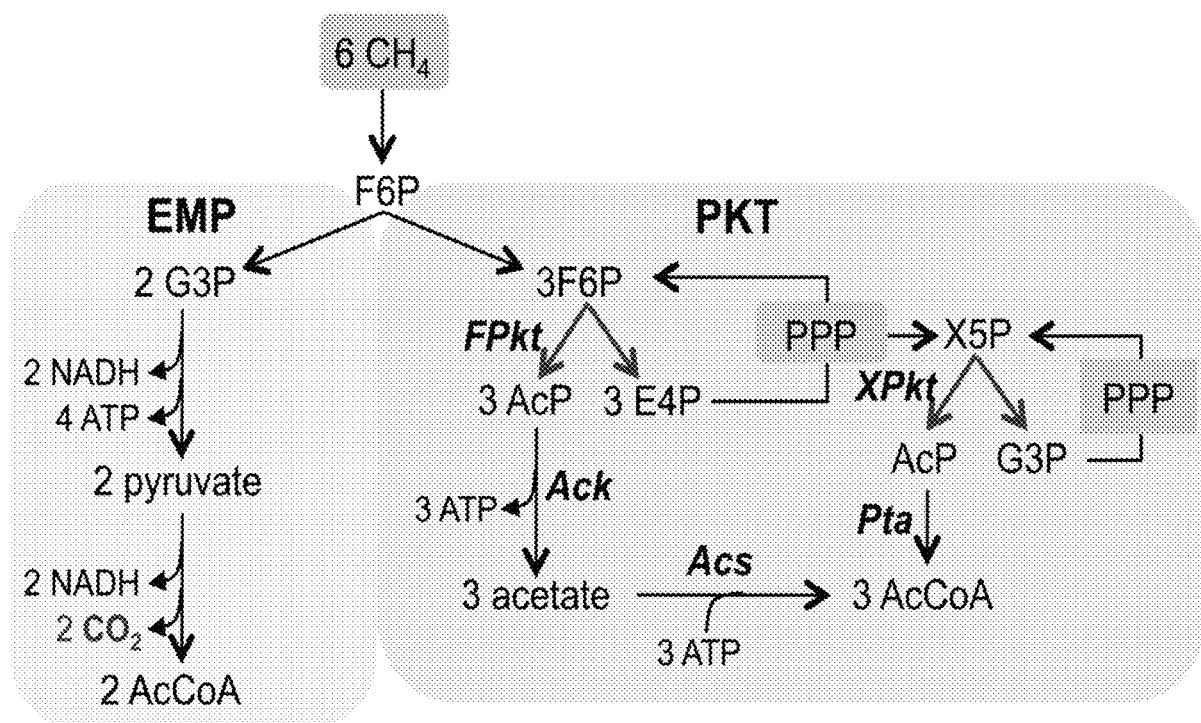
FIG. 15 shows the Embden-Meyerhof-Parnas (EMP) pathway, the phosphoketolase pathway (PKT) and how each acts on fructose-6-phosphate (F6P).
Figure 16:
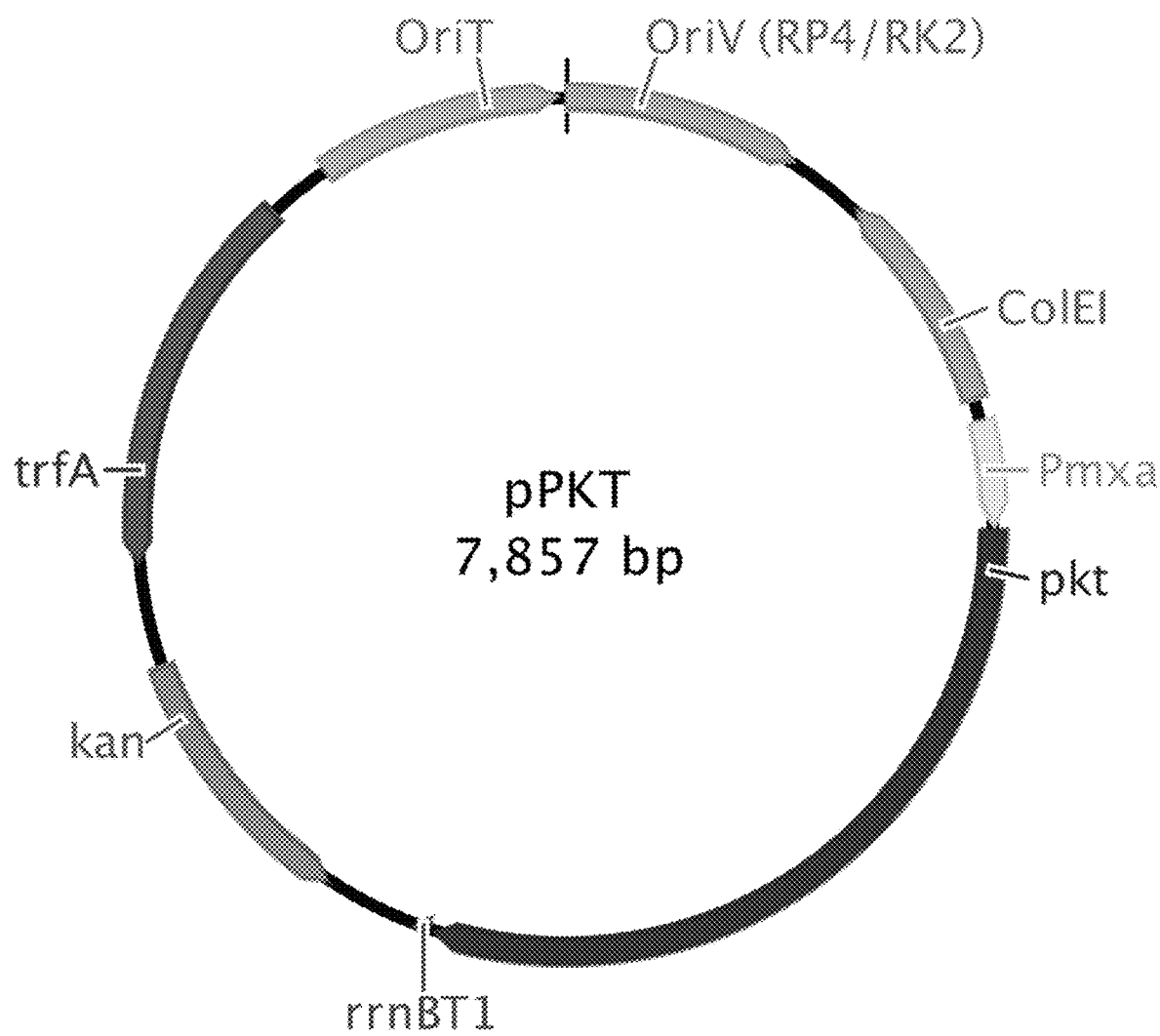
FIG. 16 shows an exemplary plasmid for high, constitutive expression of genes (such as Pkt isoforms PktA and PktB) from the methanol dehydrogenase promoter (Pmxa).
Figure 17:
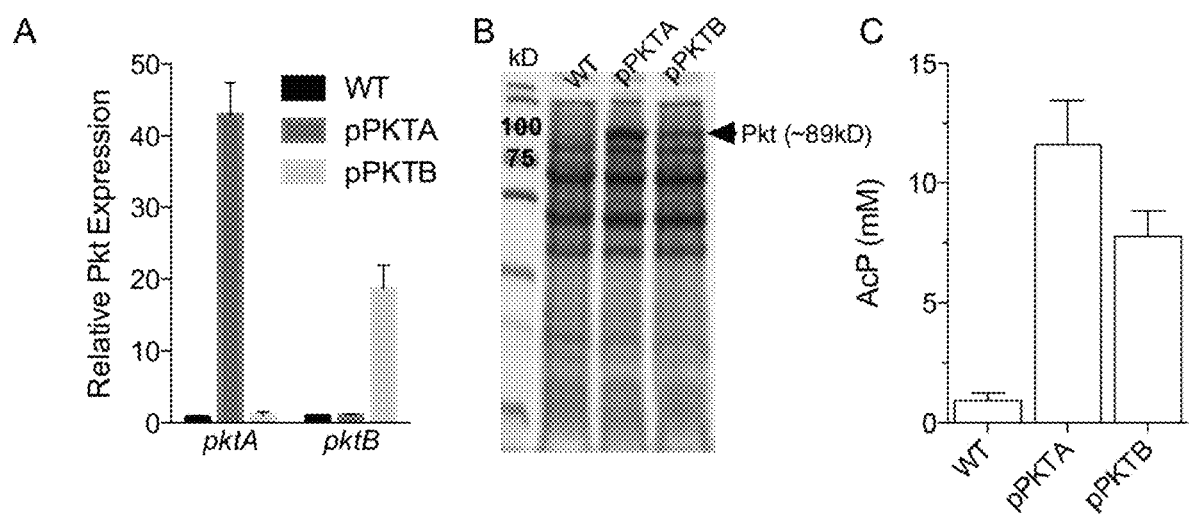
FIG. 17 shows (A) relative Pkt expression in wild-type (WT) *M. buryatense* cells or cells expressing plasmids containing PktA or PktB as determined by real-time PCR analysis; (B) SDS-PAGE analysis of whole-cell lysates demonstrating increased Pkt expression by engineered strains; and (C) in vitro conversion of fructose-6-phosphate (F6P) to acetyl-phosphate (AcP) by whole-cell lysates from wild-type (WT) cells or cells expressing plasmids containing PktA or PktB.

Additional embodiments include biocatalysts engineered to express or overexpress one or more genes encoding a phosphoketolase enzyme. Phosphoketolases catalyze the phosphorylytic cleavage of xylulose-5-phosphate to acetyl-phosphate and glyceraldehyde-3-phosphate or fructose-6-phosphate to acetyl-phosphate and erythrose-4-phosphate. In many methanotrophs, methane is assimilated into fructose-6-phosphate. As depicted in FIG. 15, expression of phosphoketolase by microorganisms such as methanotrophic bacteria may bypass pyruvate decarboxylation and convert some or all of available fructose-6-phospate to intermediates of the non-oxidative pentose phosphate pathway and acetyl-phosphate. Such a modification may increase the carbon conversion efficiency in methanotrophic biocatalysis.

Exemplary phosphoketolases include PktA and PktB from bacteria from the genus *Methylomicrobium*. The nucleotide and amino acid sequences for PktA and PktB from *M. buryatense*, for example, are provided as SEQ ID NOS:21 and 22 (PktA) and SEQ ID NOS:23 and 24 (PktB), respectively. Functional homologs of these enzymes from other species are also suitable for use in the present disclosure. Expression may be constitutive or may be inducible to allow a convenient means to switch between the conventional Embden-Meyerhof-Parnas (EMP) pathway and the phosphoketolase-mediated non-oxidative pentose phosphate pathway (see FIG. 15).

Cells may be cultured using conventional techniques and media that will vary with the cell type. Methanotrophic cells can be cultured in either methanol or methane at a wide range of temperatures depending on the nature of the cells. Examples include temperatures ranging from 20° C. to 65° C., from 30° C. to 37° C., or temperatures greater than 37° C. or greater than 45° C. Methanol may be added directly to the medium at 0.1%-5%. Gases such as methane may be bubbled into the liquid medium continuously, or added into the headspace of sealed vials. Gases may be methane, methane/air mixtures or an array of biogas or natural gas streams that may or may not be mixed with air or varying concentrations of oxygen. For example, methanotrophic cells may be cultured in NMS2 medium at 30° C. with orbital shaking at 175 rpm. Strains may be grown in sealed 1 L glass serum bottles with 25% methane in air, or 500 mL baffled flasks supplemented with 1% methanol. Additional cultivation techniques may also be suitable, including growth in solid media or large scale fermenters.

Figure 12:
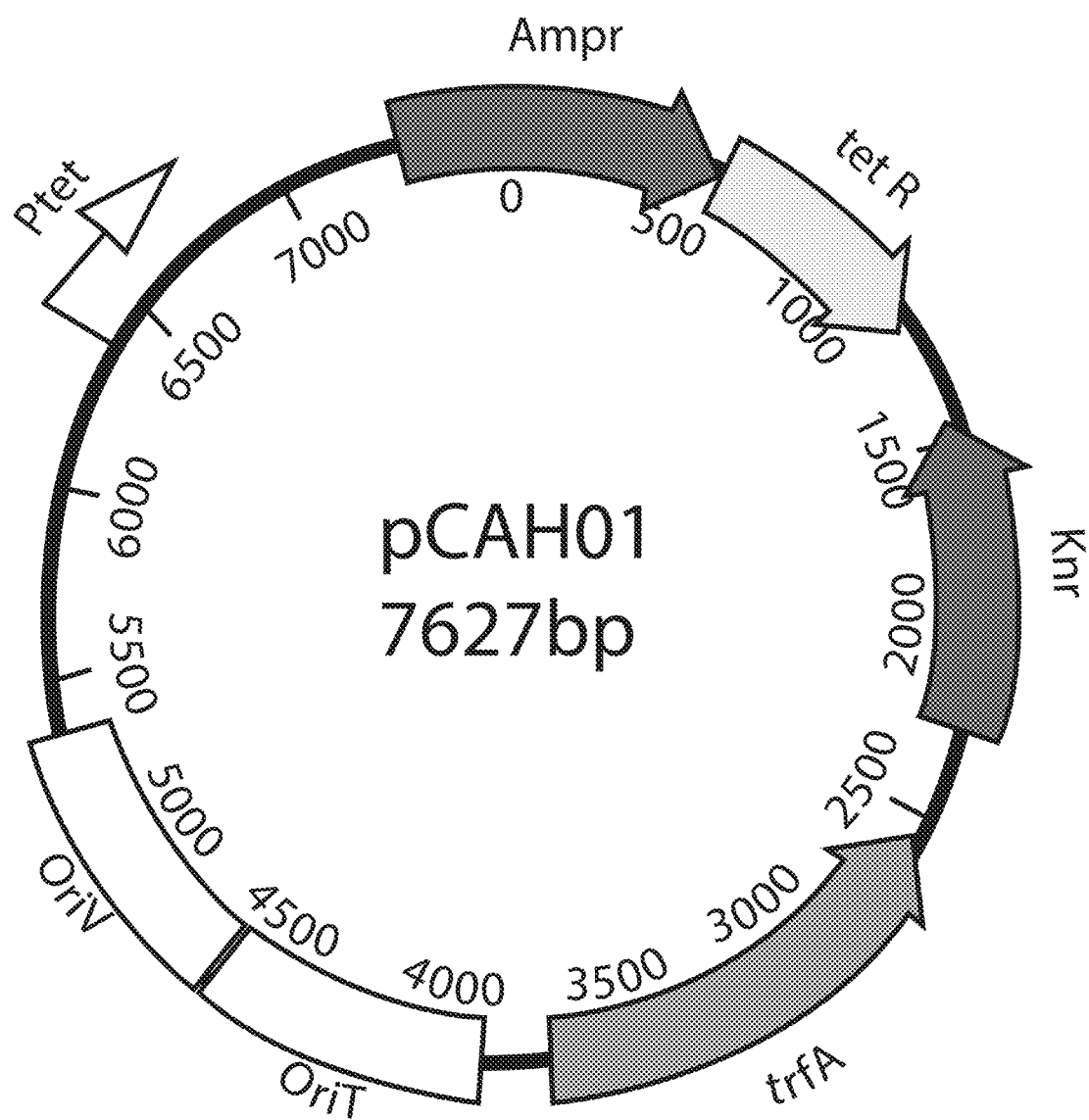
FIG. 12 shows a diagram of the pCAH01 inducible expression vector. Knr (kanamycin resistance), Ampr (ampicillin resistance), tetR (transcriptionally-fused tetracycline repressor), OriV/OriT (IncP-based origin of replication/transfer), trfA (OriV replication initiation protein).

In order to facilitate regulated, heterologous gene expression in methanotrophs, an inducible, broad-host range vector, pCAH01 (FIG. 12), was constructed by fusing the tetracycline promoter/operator (tetp/o or Ptet) from pASK75 with the IncP-based origin of the pAWP78 vector that can be replicated by *Methylomicrobium* spp. Experiments using GFP fluorescence as a readout of promoter activity indicated tightly controlled tetp/o-mediated gene expression in *M. buryatense* after induction with sub-lethal concentrations of the anhydrotetracycline inducer. The tetp/o did not show any leaky gene expression in the absence of inducer, making it an excellent tool for conditional gene expression/knock-out studies in methanotrophic bacteria that replicate vectors containing the IncP-based origin of replication.

In certain embodiments, a nucleic acid may be identical to the sequence represented herein. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein, or 80%, 81%, 82%, 83%, 84%, 85%, 86%, 87%, 88%, 89%, 90%, 91%, 92%, 93%, 94%, 95%, 96%, 97%, 98% or 99% identical to a nucleic acid sequence presented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

The nucleic acid molecules exemplified herein encode polypeptides with amino acid sequences represented herein. In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the reference amino acid sequence while possessing the function. The present disclosure encompasses cells that contain the nucleic acid molecules described herein, have genetic modifications to the nucleic acid molecules, or express the polypeptides described herein.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated. In certain embodiments, the nucleic acids are complementary DNA (cDNA) molecules.

The nucleic acids described herein may be used in methods for production of organic acids through incorporation into cells, tissues, or organisms. In some embodiments, a nucleic acid may be incorporated into a vector for expression in suitable host cells. Alternatively, gene-targeting or gene-deletion vectors may also be used to disrupt or ablate a gene. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Suitable vectors for gene expression may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including algal, bacterial, yeast, and mammalian vectors, have been described for replication and/or expression in various host cells or cell-free systems, and may be used with genes encoding the enzymes described herein for simple cloning or protein expression.

Certain embodiments may employ promoters or regulatory operons. The efficiency of expression may be enhanced by the inclusion of enhancers that are appropriate for the particular cell system that is used, such as those described in the literature. Suitable promoters also include inducible promoters. Expression systems for constitutive expression in cells include, for example, the vectors described in the figures. Inducible expression systems are also suitable for use.

Host cells can be transformed, transfected, or infected as appropriate with gene-disrupting constructs or plasmids (e.g., an expression plasmid) by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing a nucleic acid of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells by direct transformation, in which DNA is mixed with the cells and taken up without any additional manipulation, by conjugation, electroporation, or other means known in the art. Expression vectors may be expressed by host cells episomally or the gene of interest may be inserted into the chromosome of the host cell to produce cells that stably express the gene with or without the need for selective pressure. For example, expression cassettes may be targeted to neutral chromosomal sites by double recombination.

Host cells with targeted gene disruptions or carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

In exemplary embodiments, the host cell may be a microbial cell, such as a bacterial cell or a yeast cell, and may be from any genera or species of microorganism that is known to consume C1 substrates and is genetically manipulable. Exemplary microorganisms include, but are not limited to, bacteria; fungi; archaea; protists; eukaryotes, such as algae; and animals such as plankton, planarian, and amoeba.

Host cells may be cultured in an appropriate fermentation medium. An appropriate, or effective, fermentation medium refers to any medium in which a host cell, including a genetically modified microorganism, when cultured, is capable of growing and producing products such as organic acids. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors or photobioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing cells, for example, are available from ATCC.

Isolation or extraction of organic acids from the cells may be aided by mechanical processes such as crushing, for example, with an expeller or press, by supercritical fluid extraction, pH-induced precipitation, or the like. Once the organic acids have been released from the cells, they can be recovered or separated from a slurry of debris material (such as cellular residue, by-products, etc.). This can be done, for example, using techniques such as sedimentation or centrifugation. Recovered organic acids can be collected and directed to a conversion process if desired.

Processes for producing an organic acid may also comprise a removing step, wherein a portion of the organic acid is removed from the mixture to form substantially a pure organic acid. In some embodiments, the removing step may comprise a two-step process, wherein the first step comprises an adorption process wherein the organic acid is not adsorbed, and other components are selectively adsorbed. In some embodiments of the present invention, a first step comprising adorption will result in a substantially pure organic acid stream.

The first step may be followed by a second step polishing step. The second step may comprise crystallization. In still further embodiments of the present invention, the removing step is at least one of affinity chromatography, ion exchange chromatography, solvent extraction, liquid-liquid extraction, distillation, filtration, centrifugation, electrophoresis, hydrophobic interaction chromatography, gel filtration chromatography, reverse phase chromatography, chromatofocusing, differential solubilization, preparative disc-gel electrophoresis, isoelectric focusing, HPLC, reversed-phase HPLC, or countercurrent distribution, or combinations thereof. In some embodiments of the present invention, the removing step may be performed either during the mixing step or subsequent to the mixing step or both.

Separation/purification operations may be used to generate an organic acid free of or substantially free of a wide variety of impurities that may be introduced during the biological production of an organic acid. These impurities may include fermentation salts, nutrients and media to support growth, unconverted substrate, extracellular proteins and lysed cell contents, as well as the buildup of non-target metabolites. Accumulation of these constituents in culture broth may vary greatly depending on the microorganism, substrate used for conversion, biological growth conditions and bioreactor design, and broth pretreatment.

Cell removal from the broth may be achieved by a variety of solid removal unit operations. Some examples include filtration, centrifugation, and combinations thereof. Once the microorganism cell matter has been removed, further impurity removal operations may be utilized such as exposing the mixture to activated carbon.

EXAMPLES

Example 1

Plasmid and Strain Construction

Plasmids for heterologous gene expression were constructed using 2× Gibson Assembly Mix from New England Biolabs (Ipswich, Mass.) following the manufacturer's protocol. Polymerase chain reactions were performed using Q5 High-Fidelity Polymerase from New England Biolabs and primers from Integrated DNA Technologies (Coralville, Iowa). Final constructs were confirmed by sequence analysis (Genewiz, South Plainfield, N.J.). Plasmid constructs were transformed into M. alcaliphilum via conjugation. Positive transformants selected on P agar containing 100 μg/mL of kanamycin were confirmed using plasmid-specific primers in polymerase chain reactions. Escherichia coli Zymo 5a (Zymo Research, Irvine, Calif.) was used for cloning and plasmid propagation, and E. coli S17-1 λpir was used as the conjugation donor strain. E. coli strains were grown at 37° C. in Luria-Bertani (LB) broth supplemented with 50 ug/mL of kanamycin.

Cultivation, Growth Parameters, and Bioreactor Fermentations

Methylomicrobium alcaliphilum 20Z were routinely cultured in NMS2 medium (3% NaCl) at 30° C. with orbital shaking at 225 rpm. Strains were grown in sealed 150 mL glass serum bottles (Kimble Chase, Vineland, N.J.) with 20% (v/v) $CH_4$ in air, or 500 mL baffled flasks supplemented with 1% $CH_3OH$ (v/v).

Batch $CH_4$ fermentations were performed in a 0.5 L or 5.0 L BioFlo batch bioreactor (New Brunswick Scientific, Edison, N.J.) containing NMS2 medium supplemented with 8×KNO3, 2× phosphate buffer, and 4× trace element solution to support high cell growth. The temperature was maintained at 30° C., and mixing was achieved by using a bottom marine impeller and mid-height Rushton impeller at 500 rpm. A continuous flow rate of 300 ccm (0.5 L) or 3000 ccm (5.0 L) 20% (v/v) methane in air was maintained. Antifoam was added as needed.

Off-Gas Analysis and Detection of Organic Acids $CH_4$ and $CO_2$ off-gas was measured every 20 minutes for the duration of bioreactor fermentations by using infrared-based BlueSens gas detectors specific for $CH_4$ and $CO_2$ (Herten, Germany). $CH_4$ consumption was determined by calculating the difference between off-gas detected before and after inoculation. Percentage $CH_4$ consumption was converted to weight based on $CH_4$ density and the flow rate (56.64 g $CH_4$/24 hours, 0.5 L reactor; 566.4 g $CH_4$/24 hours, 5.0 L reactor).

Figure 13:
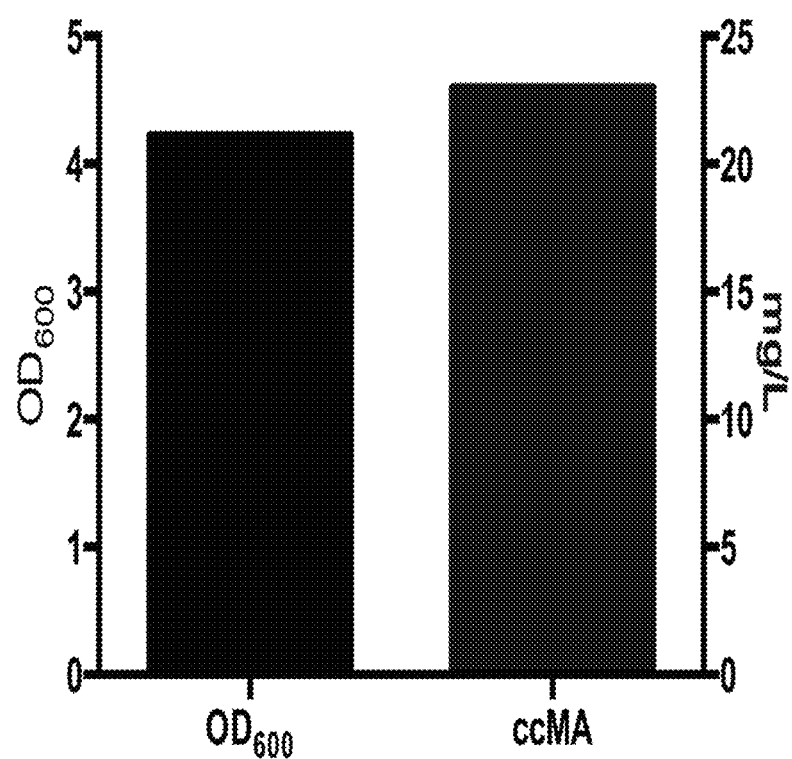
FIG. 13 shows growth ($OD_{600}$) and cis,cis-muconic acid (ccMA) production for *Methylomicrobium alcaliphilum* 20Z cells engineered express 3-dehydroshikimate dehydratase (AroZ), protocatechuic acid decarboxylase (AroY) and catechol 1,2-dioxygenase (CatA).
Figure 14:
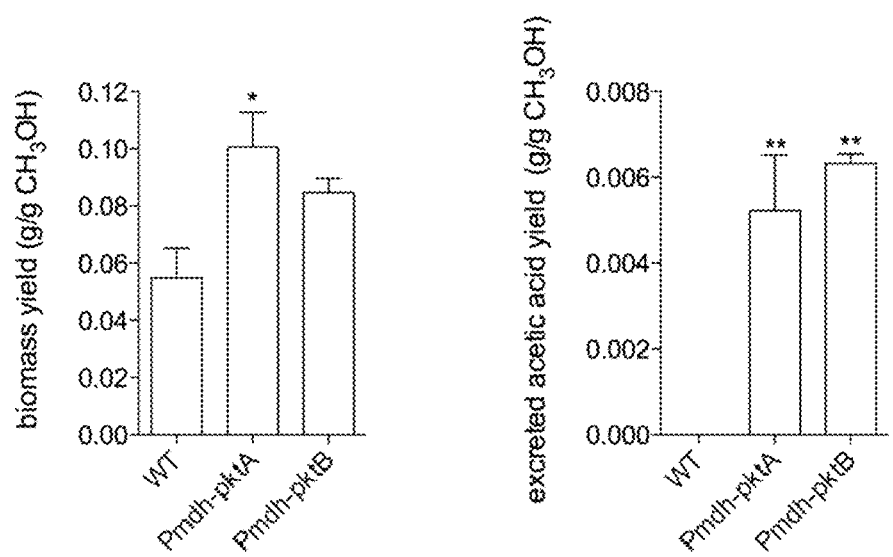
FIG. 14 shows increased carbon conversion efficiency from biocatalysts overexpressing the phosphoketolase enzyme (pktA and pktB).

High pressure liquid chromatography (HPLC) was used to detect excreted products in culture supernatants. At the indicated time, the $OD_{600}$ was measured and a 1 mL sample was taken for HPLC analysis. Culture supernatant was filtered using a 0.2 μm syringe filter or 0.5 mL 10K MWCO centrifuge tube (Life Technologies) and then separated using a model 1260 HPLC (Agilent, Santa Clara, Calif.) and a Rhenomonex Rezex RFQ-Fast Fruit H+ column (Bio-Rad). A 0.1 mL injection volume was used in 0.01 N sulfuric acid with a 1 mL/minute flow rate at 85° C. Refractive index and diode array detectors were used for compound detection, which were confirmed to have matching UV spectral profiles as pure compounds. Concentrations were calculated by regression analysis compared to known standards. FIG. 13 shows the production levels of cis,cis-muconic acid from a culture of Methylomicrobium alcaliphilum 20Z engineered to express the AroZ and AroY genes from K. variicola along with the CatA gene from Acinetobacter spp. (P76A variant).

Example 2

Expression of the Autotrophic Pathway

Figure 19:
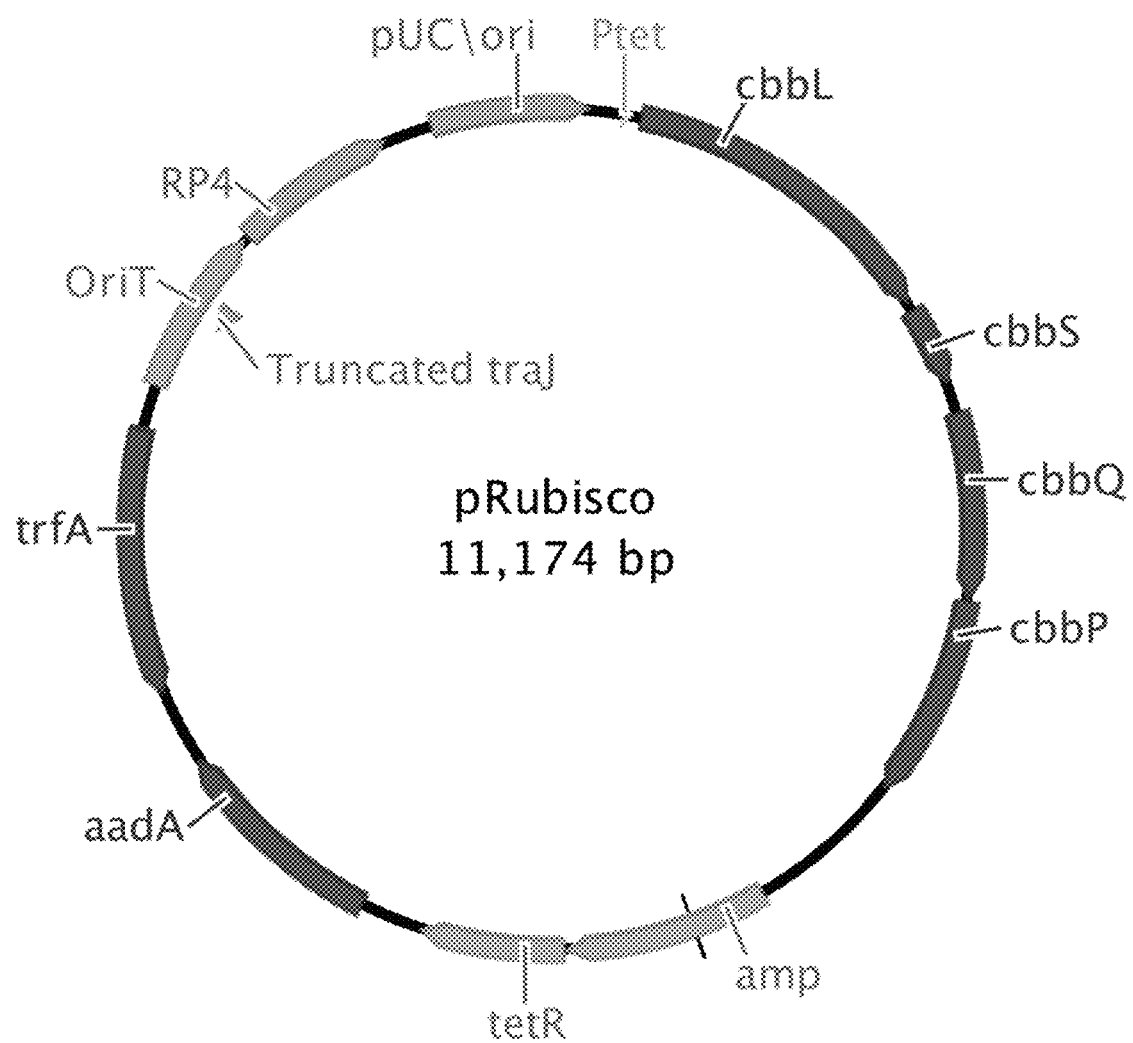
FIG. 19 shows an exemplary vector for heterologous expression of the autotrophic pathway. The cbbL, cbbS, and cbbQ genes encoding the subunit and regulatory proteins of ribulose-1,5-bisphosphate carboxylase/oxygenase (Rubisco) and phosphoribulokinase-encoding cbbP from *Methylococcus capsulatus* are included in the vector.

The cbbL, cbbS, and cbbQ genes encoding the subunit and regulatory proteins of ribulose-1,5-bisphosphate carboxylase/oxygenase (Rubisco) and the phosphoribulokinase-encoding cbbP gene from Methylococcus capsulatus were cloned into the inducible expression vector pCAH01 to create pRubisco (FIG. 19).

The pRubisco vector has been transformed into Methylomicrobium alcaliphilum cells via biparental mating and confirmed via PCR analysis. Heterologous expression of Rubisco and phosphoribulokinase was confirmed by SDS-PAGE analysis.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. An engineered cell, comprising an exogenously added gene encoding a 3-dehydroshikimate dehydratase (AroZ), a protocatechuic acid decarboxylase (AroY), a catechol 1,2-dioxygenase (CatA), a phospho-2-dehydro-3-deoxyheptonate aldolase (AroG), an anthranilate synthase (TrpE), a phosphoenolpyruvate synthase, or a transketolase; wherein the engineered cell is a methanotroph and is able to convert a C1 substrate to a muconic acid and the cell comprises genes encoding the 3-dehydroshikimate dehydratase (AroZ), the protocatechuic acid decarboxylase (AroY), and the catechol 1,2-dioxygenase (CatA).

2. The engineered cell of claim 1, wherein the 3-dehydroshikimate dehydratase (AroZ), is from *Klebsiella variicola*.

3. The engineered cell of claim 1, wherein the protocatechuic acid decarboxylase (AroY) is from *Enterobacter cloacae*.

4. The engineered cell of claim 1, wherein the catechol 1,2-dioxygenase (CatA) is from *Acinetobacter*.

5. The engineered cell of claim 1, wherein the 3-dehydroshikimate dehydratase (AroZ) is from *Klebsiella variicola*, the protocatechuic acid decarboxylase (AroY) is from *Enterobacter cloacae*, and the catechol 1,2-dioxygenase (CatA) is from *Acinetobacter*.

6. The engineered cell of claim 1, wherein the cell further comprises an exogenously added gene encoding a phosphoketolase.

7. The engineered cell of claim 1, wherein the cell further comprises an exogenously added gene encoding a CbbL, CbbS, CbbQ or CbbP polypeptide.

8. The engineered cell of claim 7, wherein the cell further comprises exogenously added genes encoding CbbL, CbbS, CbbQ and CbbP polypeptides.

9. The engineered cell of claim 1, wherein the cell is from an organism from the genus *Methylococcus*.

10. The engineered cell of claim 9, wherein the cell is *Methylococcus capsulatus*.

11. The engineered cell of claim 1, wherein the C1 substrate is methane, methanol, carbon dioxide, carbon monoxide, syngas, natural gas, or biogas.

12. A method for producing a muconic acid, comprising:
  a) culturing the engineered cell of claim 1 with a C1 substrate; and
  b) recovering the muconic acid from the culture.

* * * * *